US006013499A

United States Patent [19]

[11] Patent Number: 6,013,499
[45] Date of Patent: Jan. 11, 2000

Narumiya et al.

[54] RHO TARGET PROTEIN KINASE P160

[75] Inventors: Shuh Narumiya, Kyoto; Akihiro Iwamatsu, Yokohama, both of Japan

[73] Assignee: Kirin Beer Kabushiki Kaisha, Tokyo, Japan

[ * ] Notice: This patent is subject to a terminal disclaimer.

[21] Appl. No.: 08/685,871

[22] Filed: Jul. 24, 1996

[30] Foreign Application Priority Data

Sep. 14, 1995 [JP] Japan .................................... 7-262553
Jun. 25, 1996 [JP] Japan .................................... 8-184102

[51] Int. Cl.$^7$ .............................. C12N 9/12; C07K 14/00

[52] U.S. Cl. ................. 435/194; 435/252.3; 435/252.33; 435/325; 435/320.1; 536/23.1; 536/23.2; 536/23.5; 530/300; 530/350

[58] Field of Search ................................ 435/194, 252.3, 435/252.33, 320.1, 325; 536/23.1, 23.2, 23.5; 530/300, 350

[56] References Cited

PUBLICATIONS

Manser et al. "A brain serine/threonine protein kinase activated by cdc42 and Rac1" Nature, 367, 40–46, Jan. 6, 1994.

Ishizaki et al. "The small GTP–binding protein Rho binds to and activates a 160 kDa Ser/Thr kinase homologous to myotonic dystrophy kinase" EMBO J., 15, 1885–1893, Apr. 15, 1996.

Matsui et al. "Rho–associated kinase, a novel serine/threonine kinase, as a putative target for the small GTP binding protein Rho" EMBO J. 15, 2208–2216, 1996.

Katz et al. "Differential expression of a novel protein kinase in human B lymphocytes" J. Biol. Chem. 269, 16802–16809, Jun. 1994.

Lim et al. "Regulation of phosphorylation pathways by p21 GTPase, the p21 Ras–related Rho subfamily and its role . . . " Eur. J. Biochem. 242, 171–185, 1996.

Leung et al. "The p160 RhoA–binding kinase ROKalpha is a member of the kinase family and is involve in the reorganization of cytoskeleton" Mol. Cellu. Biol. 16, 5313–5327, Oct. 1996.

*Primary Examiner*—Robert A. Wax
*Assistant Examiner*—Nashaat T. Nashed
*Attorney, Agent, or Firm*—Foley & Lardner

[57] ABSTRACT

The object of the present invention is to provide a target protein for the activated Rho protein. The present invention is a protein having the activated Rho protein binding activity and protein kinase activity, or derivatives thereof. The molecular weight of the protein is about 160 kDa as measured by SDS-PAGE. The protein kinase activity of the protein is enhanced when it binds to the activated Rho protein.

23 Claims, 41 Drawing Sheets

FIG. 1A

```
MSTGDSFETR FEKMDNLLRD PKSEVNSDCL LDGLDALVYD LDFPALRKNK   50
NIDNFLSRYK DTINKIRDLR MKAEDYEVVK VIGRGAFGEV QLVRHKSTRK  100
VYAMKLLSKF EMIKRSDSAF FWEERDIMAF ANSPWVVQLF YAFQDDRYLY  150
MVMEYMPGGD LVNLMSNYDV PEKWARFYTA EVVLALDAIH SMGFIHRDVK  200
PDNMLLDKSG HLKLADFGTC MKMNKEGMVR CDTAVGTPDY ISPEVLKSQG  250
GDGYYGRECD WWSVGVFLYE MLVGDTPFYA DSLVGTYSKI MNHKNSLTFP  300
DDNDISKEAK NLICAFLTDR EVRLGRNGVE EIKRHLFFKN DQWAWETLRD  350
TVAPVVPDLS SDIDTSNFDD LEEDKGEEET FPIPKAFVGN QLPFVGFTYY  400
SNRRYLSSAN PNDNRTSSNA DKSLQESLQK TIYKLEEQLH NEMQLKDEME  450
QKCRTSNIKL DKIMKELDEE GNQRRNLEST VSQIEKEKML LQHRINEYQR  500
KAEQENEKRR NVENEVSTLK DQLEDLKKVS QNSQLANEKL SQLQKQLEEA  550
NDLLRTESDT AVRLRKSHTE MSKSISQLES LNRELQERNR ILENSKSQTD  600
KDYYQLQAIL EAERRDRGHD SEMIGDLQAR ITSLQEEVKH LKHNLEKVEG  650
ERKEAQDMLN HSEKEKNNLE IDLNYKLKSL QQRLEQEVNE HKVTKARLTD  700
```

FIG. 1B

```
KHQSIEEAKS VAMCEMEKKL KEEREAREKA ENRVVQIEKQ CSMLDVDLKQ    750
SQQKLEHLTG NKERMEDEVK NLTLQLEQES NKRLLLQNEL KTQAFEADNL    800
KGLEKQMKQE INTLLEAKRL LEFELAQLTK QYRGNEGQMR ELQDQLEAEQ    850
YFSTLYKTQV KELKEEIEEK NRENLKKIQE LQNEKETLAT QLDLAETKAE    900
SEQLARGLLE EQYFELTQES KKAASRNRQE ITDKDHTVSR LEEANSMLTK    950
DIEILRRENE ELTEKMKKAE EEYKLEKEEE ISNLKAAFEK NINTERTLKT   1000
QAVNKLAEIM NRKDFKIDRK KANTQDLRKK EKENRKLQLE LNQEREKFNQ   1050
MVVKHQKELN DMQAQLVEEC AHRNELQMQL ASKESDIEQL RAKLLDLSDS   1100
TSVASFPSAD ETDGNLPESR IEGWLSVPNR GNIKRYGWKK QYVVVSSKKI   1150
LFYNDEQDKE QSNPSMVLDI DKLFHVRPVT QGDVYRAETE EIPKIFQILY   1200
ANEGECRKDV EMEPVQQAEK TNFQNHKGHE FIPTLYHFPA NCDACAKPLW   1250
HVFKPPPALE CRRCHVKCHR DHLDKKEDLI CPCKVSYDVT SARDMLLLAC   1300
SQDEQKKWVT HLVKKIPKNP PSGFVRASPR TLSTRSTANQ SFRKVVKNTS   1350
GKTS                                                     1354
```

FIG. 2A

```
                 9                18                27                36                45                54
5' TCA CCC GCC CTT TGC TTT CGC CTT TCC TCT TCT CCC TCC CTT GTT GCC CGG AGG

                63                72                81                90                99               108
   AGT CTC CAC CCT GCT TCT CTT TCT CTA CCC GCT CCT GCC CAT CTC GGG ACG GGG

               117               126               135               144               153               162
   ACC CCT CCA TGG CGA CGG CGG CCG GGG CCC GCT AGA CTG AAG CAC CTC GCC GGA

               171               180               189               198               207               216
   GCG ACG AGG CTG GTG GCG ACG GCG CTG TCG GCT GTC GTG AGG GGC TGC CGG GTG

               225               234               243               252               261               270
   GGA TGC GAC TTT GGG CGT CCG AGC GGC TGT GGG TCG CTG TTG CCC CCG GCC CGG

               279               288               297               306               315               324
   GGT CTG GAG AGC GGA GGT CCC CTC AGT GAG GGG AAG ACG GGG GAA CCG GGC GCA

               333               342               351               360               369               378
   CCT GGT GAC CCT GAG GTT CCG GCT CCT CCG CCC CGC GGC TGC GAA CCC ACC GCG
```

FIG. 2B

```
        387         396         405         414         423         432
GAG GAA GTT GGT TGA AAT TGC TTT CCG CTG CTG GTG CTG GTA AGA GGG CAT TGT

        441         450         459         468         477         486
CAC AGC AGC AGC AAC ATG TCG ACT GGG GAC AGT TTT GAG ACT CGA TTT GAA AAA
                    --- --- --- --- --- --- --- --- --- --- --- --- ---
                     M   S   T   G   D   S   F   E   T   R   F   E   K

        495         504         513         522         531         540
ATG GAC AAC CTG CTG CGG GAT CCC AAA TCG GAA GTG AAT TCG GAT TGT TTG CTG
--- --- --- --- --- --- --- --- --- --- --- --- --- --- --- --- --- ---
 M   D   N   L   L   R   D   P   K   S   E   V   N   S   D   C   L   L

        549         558         567         576         585         594
GAT GGA TTG GAT GCT TTG GTA TAT GAT TTG GAT TTT CCT GCC TTA AGA AAA AAC
--- --- --- --- --- --- --- --- --- --- --- --- --- --- --- --- --- ---
 D   G   L   D   A   L   V   Y   D   L   D   F   P   A   L   R   K   N

        603         612         621         630         639         648
AAA AAT ATT GAC AAC TTT TTA AGC AGA TAT AAA GAC ACA ATA AAT AAA ATC AGA
--- --- --- --- --- --- --- --- --- --- --- --- --- --- --- --- --- ---
 K   N   I   D   N   F   L   S   R   Y   K   D   T   I   N   K   I   R
```

FIG. 3A

```
        657         666         675         684         693         702
GAT TTA CGA ATG AAA GCT GAA GAT TAT GAA GTA GTG AAG GTG ATT GGT AGA GGT
--- --- --- --- --- --- --- --- --- --- --- --- --- --- --- --- --- ---
 D   L   R   M   K   A   E   D   Y   E   V   V   K   V   I   G   R   G

        711         720         729         738         747         756
GCA TTT GGA GAA GTT CAA TTG GTA AGG CAT AAA TCC ACC AGG AAG GTA TAT GCT
--- --- --- --- --- --- --- --- --- --- --- --- --- --- --- --- --- ---
 A   F   G   E   V   Q   L   V   R   H   K   S   T   R   K   V   Y   A

        765         774         783         792         801         810
ATG AAG CTT CTC AGC AAA TTT GAA ATG ATA AAG AGA TCT GAT TCT GCT TTT TTC
--- --- --- --- --- --- --- --- --- --- --- --- --- --- --- --- --- ---
 M   K   L   L   S   K   F   E   M   I   K   R   S   D   S   A   F   F

        819         828         837         846         855         864
TGG GAA GAA AGG GAC ATC ATG GCT TTT GCC AAC AGT CCT TGG GTT GTT CAG CTT
--- --- --- --- --- --- --- --- --- --- --- --- --- --- --- --- --- ---
 W   E   E   R   D   I   M   A   F   A   N   S   P   W   V   V   Q   L

        873         882         891         900         909         918
TTT TAT GCA TTC CAA GAT GAT CGT TAT CTC TAC ATG GTG ATG GAA TAC ATG CCT
--- --- --- --- --- --- --- --- --- --- --- --- --- --- --- --- --- ---
 F   Y   A   F   Q   D   D   R   Y   L   Y   M   V   M   E   Y   M   P
```

FIG. 3B

```
        927         936         945         954         963         972
GGT GGA GAT CTT GTA AAC TTA ATG AGC AAC TAT GAT GTG CCT GAA AAA TGG GCA
--- --- --- --- --- --- --- --- --- --- --- --- --- --- --- --- --- ---
 G   G   D   L   V   N   L   M   S   N   Y   D   V   P   E   K   W   A

        981         990         999        1008        1017        1026
CGA TTC TAT ACT GCA GAA GTA GTT CTT GCA TTG GAT GCA ATC CAT TCC ATG GGT
--- --- --- --- --- --- --- --- --- --- --- --- --- --- --- --- --- ---
 R   F   Y   T   A   E   V   V   L   A   L   D   A   I   H   S   M   G

       1035        1044        1053        1062        1071        1080
TTT ATT CAC AGA GAT GTG AAG CCT GAT AAC ATG CTG CTG GAT AAA TCT GGA CAT
--- --- --- --- --- --- --- --- --- --- --- --- --- --- --- --- --- ---
 F   I   H   R   D   V   K   P   D   N   M   L   L   D   K   S   G   H

       1089        1098        1107        1116        1125        1134
TTG AAG TTA GCA GAT TTT GGT ACT TGT ATG AAG ATG AAT AAG GAA GGC ATG GTA
--- --- --- --- --- --- --- --- --- --- --- --- --- --- --- --- --- ---
 L   K   L   A   D   F   G   T   C   M   K   M   N   K   E   G   M   V

       1143        1152        1161        1170        1179        1188
CGA TGT GAT ACA GCG GTT GGA ACA CCT GAT TAT ATT TCC CCT GAA GTA TTA AAA
--- --- --- --- --- --- --- --- --- --- --- --- --- --- --- --- --- ---
 R   C   D   T   A   V   G   T   P   D   Y   I   S   P   E   V   L   K
```

FIG. 4A

```
         1197           1206           1215           1224           1233           1242
TCC CAA GGT GGT GAT GGT TAT TAT GGA AGA GAA TGT GAC TGG TGG TCG GTT GGG
--- --- --- --- --- --- --- --- --- --- --- --- --- --- --- --- --- ---
 S   Q   G   G   D   G   Y   Y   G   R   E   C   D   W   W   S   V   G

         1251           1260           1269           1278           1287           1296
GTA TTT TTA TAC GAA ATG CTT GTA GGT GAT ACA CCT TTT TAT GCA GAT TCT TTG
--- --- --- --- --- --- --- --- --- --- --- --- --- --- --- --- --- ---
 V   F   L   Y   E   M   L   V   G   D   T   P   F   Y   A   D   S   L

         1305           1314           1323           1332           1341           1350
GTT GGA ACT TAC AGT AAA ATT ATG AAC CAT AAA AAT TCA CTT ACC TTT CCT GAT
--- --- --- --- --- --- --- --- --- --- --- --- --- --- --- --- --- ---
 V   G   T   Y   S   K   I   M   N   H   K   N   S   L   T   F   P   D

         1359           1368           1377           1386           1395           1404
GAT AAT GAC ATA TCA AAA GAA GCA AAA AAC CTT ATT TGT GCC TTC CTT ACT GAC
--- --- --- --- --- --- --- --- --- --- --- --- --- --- --- --- --- ---
 D   N   D   I   S   K   E   A   K   N   L   I   C   A   F   L   T   D

         1413           1422           1431           1440           1449           1458
AGG GAA GTG AGG TTA GGG CGA AAT GGT GTA GAA GAA ATC AAA CGA CAT CTC TTC
--- --- --- --- --- --- --- --- --- --- --- --- --- --- --- --- --- ---
 R   E   V   R   L   G   R   N   G   V   E   E   I   K   R   H   L   F
```

FIG. 4B

```
       1467        1476        1485        1494        1503        1512
TTC AAA AAT GAC CAG TGG GCT TGG GAA ACG CTC CGA GAC ACT GTA GCA CCA GTT
--- --- --- --- --- --- --- --- --- --- --- --- --- --- --- --- --- ---
 F   K   N   D   Q   W   A   W   E   T   L   R   D   T   V   A   P   V

       1521        1530        1539        1548        1557        1566
GTA CCC GAT TTA AGT AGT GAC ATT GAT ACT AGT AAT TTT GAT GAC TTG GAA GAA
--- --- --- --- --- --- --- --- --- --- --- --- --- --- --- --- --- ---
 V   P   D   L   S   S   D   I   D   T   S   N   F   D   D   L   E   E

       1575        1584        1593        1602        1611        1620
GAT AAA GGA GAG GAA GAA ACA TTC CCT ATT CCT AAA GCT TTC GTT GGC AAT CAA
--- --- --- --- --- --- --- --- --- --- --- --- --- --- --- --- --- ---
 D   K   G   E   E   E   T   F   P   I   P   K   A   F   V   G   N   Q

       1629        1638        1647        1656        1665        1674
CTA CCT TTT GTA GGA TTT ACA TAT TAT AGC AAT CGT AGA TAC TTA TCT TCA GCA
--- --- --- --- --- --- --- --- --- --- --- --- --- --- --- --- --- ---
 L   P   F   V   G   F   T   Y   Y   S   N   R   R   Y   L   S   S   A

       1683        1692        1701        1710        1719        1728
AAT CCT AAT GAT AAC AGA ACT AGC TCC AAT GCA GAT AAA AGC TTG CAG GAA AGT
--- --- --- --- --- --- --- --- --- --- --- --- --- --- --- --- --- ---
 N   P   N   D   N   R   T   S   S   N   A   D   K   S   L   Q   E   S
```

FIG. 5A

```
        1737        1746        1755        1764        1773        1782
TTG CAA AAA ACA ATC TAT AAG CTG GAA GAA CAG CTG CAT AAT GAA ATG CAG TTA
--- --- --- --- --- --- --- --- --- --- --- --- --- --- --- --- --- ---
 L   Q   K   T   I   Y   K   L   E   E   Q   L   H   N   E   M   Q   L

        1791        1800        1809        1818        1827        1836
AAA GAT GAA ATG GAG CAG AAG TGC AGA ACC TCA AAC ATA AAA CTA GAC AAG ATA
--- --- --- --- --- --- --- --- --- --- --- --- --- --- --- --- --- ---
 K   D   E   M   E   Q   K   C   R   T   S   N   I   K   L   D   K   I

        1845        1854        1863        1872        1881        1890
ATG AAA GAA TTG GAT GAA GAG GGA AAT CAA AGA AGA AAT CTA GAA TCT ACA GTG
--- --- --- --- --- --- --- --- --- --- --- --- --- --- --- --- --- ---
 M   K   E   L   D   E   E   G   N   Q   R   R   N   L   E   S   T   V

        1899        1908        1917        1926        1935        1944
TCT CAG ATT GAG AAG GAG AAA ATG TTG CTA CAG CAT AGA ATT AAT GAG TAC CAA
--- --- --- --- --- --- --- --- --- --- --- --- --- --- --- --- --- ---
 S   Q   I   E   K   E   K   M   L   L   Q   H   R   I   N   E   Y   Q

        1953        1962        1971        1980        1989        1998
AGA AAA GCT GAA CAG GAA AAT GAG AAG AGA AGA AAT GTA GAA AAT GAA GTT TCT
--- --- --- --- --- --- --- --- --- --- --- --- --- --- --- --- --- ---
 R   K   A   E   Q   E   N   E   K   R   R   N   V   E   N   E   V   S
```

FIG. 5B

```
        2007           2016           2025           2034           2043           2052
ACA TTA AAG GAT CAG TTG GAA GAC TTA AAG AAA GTC AGT CAG AAT TCA CAG CTT
--- --- --- --- --- --- --- --- --- --- --- --- --- --- --- --- --- ---
 T   L   K   D   Q   L   E   D   L   K   K   V   S   Q   N   S   Q   L

        2061           2070           2079           2088           2097           2106
GCT AAT GAG AAG CTG TCC CAG TTA CAA AAG CAG CTA GAA GAA GCC AAT GAC TTA
--- --- --- --- --- --- --- --- --- --- --- --- --- --- --- --- --- ---
 A   N   E   K   L   S   Q   L   Q   K   Q   L   E   E   A   N   D   L

        2115           2124           2133           2142           2151           2160
CTT AGG ACA GAA TCG GAC ACA GCT GTA AGA TTG AGG AAG AGT CAC ACA GAG ATG
--- --- --- --- --- --- --- --- --- --- --- --- --- --- --- --- --- ---
 L   R   T   E   S   D   T   A   V   R   L   R   K   S   H   T   E   M

        2169           2178           2187           2196           2205           2214
AGC AAG TCA ATT AGT CAG TTA GAG TCC CTG AAC AGA GAG TTG CAA GAG AGA AAT
--- --- --- --- --- --- --- --- --- --- --- --- --- --- --- --- --- ---
 S   K   S   I   S   Q   L   E   S   L   N   R   E   L   Q   E   R   N

        2223           2232           2241           2250           2259           2268
CGA ATT TTA GAG AAT TCT AAG TCA CAA ACA GAC AAA GAT TAT TAC CAG CTG CAA
--- --- --- --- --- --- --- --- --- --- --- --- --- --- --- --- --- ---
 R   I   L   E   N   S   K   S   Q   T   D   K   D   Y   Y   Q   L   Q
```

FIG. 6A

```
         2277         2286         2295         2304         2313         2322
GCT ATA TTA GAA GCT GAA CGA AGA GAC AGA GGT CAT GAT TCT GAG ATG ATT GGA
--- --- --- --- --- --- --- --- --- --- --- --- --- --- --- --- --- ---
 A   I   L   E   A   E   R   R   D   R   G   H   D   S   E   M   I   G

         2331         2340         2349         2358         2367         2376
GAC CTT CAA GCT CGA ATT ACA TCT TTA CAA GAG GAG GTG AAG CAT CTC AAA CAT
--- --- --- --- --- --- --- --- --- --- --- --- --- --- --- --- --- ---
 D   L   Q   A   R   I   T   S   L   Q   E   E   V   K   H   L   K   H

         2385         2394         2403         2412         2421         2430
AAT CTC GAA AAA GTG GAA GGA GAA AGA AAA GAG GCT CAA GAC ATG CTT AAT CAC
--- --- --- --- --- --- --- --- --- --- --- --- --- --- --- --- --- ---
 N   L   E   K   V   E   G   E   R   K   E   A   Q   D   M   L   N   H

         2439         2448         2457         2466         2475         2484
TCA GAA AAG GAA AAG AAT AAT TTA GAG ATA GAT TTA AAC TAC AAA CTT AAA TCA
--- --- --- --- --- --- --- --- --- --- --- --- --- --- --- --- --- ---
 S   E   K   E   K   N   N   L   E   I   D   L   N   Y   K   L   K   S

         2493         2502         2511         2520         2529         2538
TTA CAA CAA CGG TTA GAA CAA GAG GTA AAT GAA CAC AAA GTA ACC AAA GCT CGT
--- --- --- --- --- --- --- --- --- --- --- --- --- --- --- --- --- ---
 L   Q   Q   R   L   E   Q   E   V   N   E   H   K   V   T   K   A   R
```

FIG. 6B

```
        2547        2556        2565        2574        2583        2592
TTA ACT GAC AAA CAT CAA TCT ATT GAA GAG GCA AAG TCT GTG GCA ATG TGT GAG
--- --- --- --- --- --- --- --- --- --- --- --- --- --- --- --- --- ---
 L   T   D   K   H   Q   S   I   E   E   A   K   S   V   A   M   C   E

        2601        2610        2619        2628        2637        2646
ATG GAA AAA AAG CTG AAA GAA GAA AGA GAA GCT CGA GAG AAG GCT GAA AAT CGG
--- --- --- --- --- --- --- --- --- --- --- --- --- --- --- --- --- ---
 M   E   K   K   L   K   E   E   R   E   A   R   E   K   A   E   N   R

        2655        2664        2673        2682        2691        2700
GTT GTT CAG ATT GAG AAA CAG TGT TCC ATG CTA GAC GTT GAT CTG AAG CAA TCT
--- --- --- --- --- --- --- --- --- --- --- --- --- --- --- --- --- ---
 V   V   Q   I   E   K   Q   C   S   M   L   D   V   D   L   K   Q   S

        2709        2718        2727        2736        2745        2754
CAG CAG AAA CTA GAA CAT TTG ACT GGA AAT AAA GAA AGG ATG GAG GAT GAA GTT
--- --- --- --- --- --- --- --- --- --- --- --- --- --- --- --- --- ---
 Q   Q   K   L   E   H   L   T   G   N   K   E   R   M   E   D   E   V

        2763        2772        2781        2790        2799        2808
AAG AAT CTA ACC CTG CAA CTG GAG CAG GAA TCA AAT AAG CGG CTG TTG TTA CAA
--- --- --- --- --- --- --- --- --- --- --- --- --- --- --- --- --- ---
 K   N   L   T   L   Q   L   E   Q   E   S   N   K   R   L   L   L   Q
```

FIG. 7A

```
                2817                2826                2835                2844                2853                2862
AAT GAA TTG AAG ACT CAA GCA TTT GAG GCA GAC AAT TTA AAA GGT TTA GAA AAG
--- --- --- --- --- --- --- --- --- --- --- --- --- --- --- --- --- ---
 N   E   L   K   T   Q   A   F   E   A   D   N   L   K   G   L   E   K

                2871                2880                2889                2898                2907                2916
CAG ATG AAA CAG GAA ATA AAT ACT TTA TTG GAA GCA AAG AGA TTA TTA GAA TTT
--- --- --- --- --- --- --- --- --- --- --- --- --- --- --- --- --- ---
 Q   M   K   Q   E   I   N   T   L   L   E   A   K   R   L   L   E   F

                2925                2934                2943                2952                2961                2970
GAG TTA GCT CAG CTT ACG AAA CAG TAT AGA GGA AAT GAA GGA CAG ATG CGG GAG
--- --- --- --- --- --- --- --- --- --- --- --- --- --- --- --- --- ---
 E   L   A   Q   L   T   K   Q   Y   R   G   N   E   G   Q   M   R   E

                2979                2988                2997                3006                3015                3024
CTA CAA GAT CAG CTT GAA GCT GAG CAA TAT TTC TCG ACA CTT TAT AAA ACC CAG
--- --- --- --- --- --- --- --- --- --- --- --- --- --- --- --- --- ---
 L   Q   D   Q   L   E   A   E   Q   Y   F   S   T   L   Y   K   T   Q

                3033                3042                3051                3060                3069                3078
GTA AAG GAA CTT AAA GAA GAA ATT GAA GAA AAA AAC AGA GAA AAT TTA AAG AAA
--- --- --- --- --- --- --- --- --- --- --- --- --- --- --- --- --- ---
 V   K   E   L   K   E   E   I   E   E   K   N   R   E   N   L   K   K
```

FIG. 7B

```
          3087        3096        3105        3114        3123        3132
ATA CAG GAA CTA CAA AAT GAA AAA GAA ACT CTT GCT ACT CAG TTG GAT CTA GCA
--- --- --- --- --- --- --- --- --- --- --- --- --- --- --- --- --- ---
 I   Q   E   L   Q   N   E   K   E   T   L   A   T   Q   L   D   L   A

          3141        3150        3159        3168        3177        3186
GAA ACA AAA GCT GAG TCT GAG CAG TTG GCG CGA GGC CTT CTG GAA GAA CAG TAT
--- --- --- --- --- --- --- --- --- --- --- --- --- --- --- --- --- ---
 E   T   K   A   E   S   E   Q   L   A   R   G   L   L   E   E   Q   Y

          3195        3204        3213        3222        3231        3240
TTT GAA TTG ACG CAA GAA AGC AAG AAA GCT GCT TCA AGA AAT AGA CAA GAG ATT
--- --- --- --- --- --- --- --- --- --- --- --- --- --- --- --- --- ---
 F   E   L   T   Q   E   S   K   K   A   A   S   R   N   R   Q   E   I

          3249        3258        3267        3276        3285        3294
ACA GAT AAA GAT CAC ACT GTT AGT CGG CTT GAA GAA GCA AAC AGC ATG CTA ACC
--- --- --- --- --- --- --- --- --- --- --- --- --- --- --- --- --- ---
 T   D   K   D   H   T   V   S   R   L   E   E   A   N   S   M   L   T

          3303        3312        3321        3330        3339        3348
AAA GAT ATT GAA ATA TTA AGA AGA GAG AAT GAA GAG CTA ACA GAG AAA ATG AAG
--- --- --- --- --- --- --- --- --- --- --- --- --- --- --- --- --- ---
 K   D   I   E   I   L   R   R   E   N   E   E   L   T   E   K   M   K
```

FIG. 8A

```
        3357        3366        3375        3384        3393        3402
AAG GCA GAG GAA GAA TAT AAA CTG GAG AAG GAG GAG GAG ATC AGT AAT CTT AAG
--- --- --- --- --- --- --- --- --- --- --- --- --- --- --- --- --- ---
 K   A   E   E   E   Y   K   L   E   K   E   E   E   I   S   N   L   K

        3411        3420        3429        3438        3447        3456
GCT GCC TTT GAA AAG AAT ATC AAC ACT GAA CGA ACC CTT AAA ACA CAG GCT GTT
--- --- --- --- --- --- --- --- --- --- --- --- --- --- --- --- --- ---
 A   A   F   E   K   N   I   N   T   E   R   T   L   K   T   Q   A   V

        3465        3474        3483        3492        3501        3510
AAC AAA TTG GCA GAA ATA ATG AAT CGA AAA GAT TTT AAA ATT GAT AGA AAG AAA
--- --- --- --- --- --- --- --- --- --- --- --- --- --- --- --- --- ---
 N   K   L   A   E   I   M   N   R   K   D   F   K   I   D   R   K   K

        3519        3528        3537        3546        3555        3564
GCT AAT ACA CAA GAT TTG AGA AAG AAA GAA AAG GAA AAT CGA AAG CTG CAA CTG
--- --- --- --- --- --- --- --- --- --- --- --- --- --- --- --- --- ---
 A   N   T   Q   D   L   R   K   K   E   K   E   N   R   K   L   Q   L

        3573        3582        3591        3600        3609        3618
GAA CTC AAC CAA GAA AGA GAG AAA TTC AAC CAG ATG GTA GTG AAA CAT CAG AAG
--- --- --- --- --- --- --- --- --- --- --- --- --- --- --- --- --- ---
 E   L   N   Q   E   R   E   K   F   N   Q   M   V   V   K   H   Q   K
```

FIG. 8B

```
        3627        3636        3645        3654        3663        3672
GAA CTG AAT GAC ATG CAA GCG CAA TTG GTA GAA GAA TGT GCA CAT AGG AAT GAG
--- --- --- --- --- --- --- --- --- --- --- --- --- --- --- --- --- ---
 E   L   N   D   M   Q   A   Q   L   V   E   E   C   A   H   R   N   E

        3681        3690        3699        3708        3717        3726
CTT CAG ATG CAG TTG GCC AGC AAA GAG AGT GAT ATT GAG CAA TTG CGT GCT AAA
--- --- --- --- --- --- --- --- --- --- --- --- --- --- --- --- --- ---
 L   Q   M   Q   L   A   S   K   E   S   D   I   E   Q   L   R   A   K

        3735        3744        3753        3762        3771        3780
CTT TTG GAC CTC TCG GAT TCT ACA AGT GTT GCT AGT TTT CCT AGT GCT GAT GAA
--- --- --- --- --- --- --- --- --- --- --- --- --- --- --- --- --- ---
 L   L   D   L   S   D   S   T   S   V   A   S   F   P   S   A   D   E

        3789        3798        3807        3816        3825        3834
ACT GAT GGT AAC CTC CCA GAG TCA AGA ATT GAA GGT TGG CTT TCA GTA CCA AAT
--- --- --- --- --- --- --- --- --- --- --- --- --- --- --- --- --- ---
 T   D   G   N   L   P   E   S   R   I   E   G   W   L   S   V   P   N

        3843        3852        3861        3870        3879        3888
AGA GGA AAT ATC AAA CGA TAT GGC TGG AAG AAA CAG TAT GTT GTG GTA AGC AGC
--- --- --- --- --- --- --- --- --- --- --- --- --- --- --- --- --- ---
 R   G   N   I   K   R   Y   G   W   K   K   Q   Y   V   V   V   S   S
```

FIG. 9A

```
        3897        3906        3915        3924        3933        3942
AAA AAA ATT TTG TTC TAT AAT GAC GAA CAA GAT AAG GAG CAA TCC AAT CCA TCT
--- --- --- --- --- --- --- --- --- --- --- --- --- --- --- --- --- ---
 K   K   I   L   F   Y   N   D   E   Q   D   K   E   Q   S   N   P   S

        3951        3960        3969        3978        3987        3996
ATG GTA TTG GAC ATA GAT AAA CTG TTT CAC GTT AGA CCT GTA ACC CAA GGA GAT
--- --- --- --- --- --- --- --- --- --- --- --- --- --- --- --- --- ---
 M   V   L   D   I   D   K   L   F   H   V   R   P   V   T   Q   G   D

        4005        4014        4023        4032        4041        4050
GTG TAT AGA GCT GAA ACT GAA GAA ATT CCT AAA ATA TTC CAG ATA CTA TAT GCA
--- --- --- --- --- --- --- --- --- --- --- --- --- --- --- --- --- ---
 V   Y   R   A   E   T   E   E   I   P   K   I   F   Q   I   L   Y   A

        4059        4068        4077        4086        4095        4104
AAT GAA GGT GAA TGT AGA AAA GAT GTA GAG ATG GAA CCA GTA CAA CAA GCT GAA
--- --- --- --- --- --- --- --- --- --- --- --- --- --- --- --- --- ---
 N   E   G   E   C   R   K   D   V   E   M   E   P   V   Q   Q   A   E

        4113        4122        4131        4140        4149        4158
AAA ACT AAT TTC CAA AAT CAC AAA GGC CAT GAG TTT ATT CCT ACA CTC TAC CAC
--- --- --- --- --- --- --- --- --- --- --- --- --- --- --- --- --- ---
 K   T   N   F   Q   N   H   K   G   H   E   F   I   P   T   L   Y   H
```

FIG. 9B

```
       4167         4176         4185          4194          4203          4212
TTT CCT GCC AAT TGT GAT GCC TGT GCC AAA CCT CTC TGG CAT GTT TTT AAG CCA
--- --- --- --- --- --- --- --- --- --- --- --- --- --- --- --- --- ---
 F   P   A   N   C   D   A   C   A   K   P   L   W   H   V   F   K   P

       4221         4230         4239          4248          4257          4266
CCC CCT GCC CTA GAG TGT CGA AGA TGC CAT GTT AAG TGC CAC AGA GAT CAC TTA
--- --- --- --- --- --- --- --- --- --- --- --- --- --- --- --- --- ---
 P   P   A   L   E   C   R   R   C   H   V   K   C   H   R   D   H   L

       4275         4284         4293          4302          4311          4320
GAT AAG AAA GAG GAC TTA ATT TGT CCA TGT AAA GTA AGT TAT GAT GTA ACA TCA
--- --- --- --- --- --- --- --- --- --- --- --- --- --- --- --- --- ---
 D   K   K   E   D   L   I   C   P   C   K   V   S   Y   D   V   T   S

       4329         4338         4347          4356          4365          4374
GCA AGA GAT ATG CTG CTG TTA GCA TGT TCT CAG GAT GAA CAA AAA AAA TGG GTA
--- --- --- --- --- --- --- --- --- --- --- --- --- --- --- --- --- ---
 A   R   D   M   L   L   L   A   C   S   Q   D   E   Q   K   K   W   V

       4383         4392         4401          4410          4419          4428
ACT CAT TTA GTA AAG AAA ATC CCT AAG AAT CCA CCA TCT GGT TTT GTT CGT GCT
--- --- --- --- --- --- --- --- --- --- --- --- --- --- --- --- --- ---
 T   H   L   V   K   K   I   P   K   N   P   P   S   G   F   V   R   A
```

FIG. 10

```
        4437         4446         4455         4464         4473         4482
TCC CCT CGA ACG CTT TCT ACA AGA TCC ACT GCA AAT CAG TCT TTC CGG AAA GTG
--- --- --- --- --- --- --- --- --- --- --- --- --- --- --- --- --- ---
 S   P   R   T   L   S   T   R   S   T   A   N   Q   S   F   R   K   V

        4491         4500         4509         4518         4527         4536
GTC AAA AAT ACA TCT GGA AAA ACT AGT TAA CCA TGT GAC TGA GTG CCC TGT GGA
--- --- --- --- --- --- --- --- --- ---
 V   K   N   T   S   G   K   T   S   *

        4545         4554         4563         4572         4581         4590
ATC GTG TGG GAT GCT ACC TGA TAA ACC AGG CTT CTT TAA CCA TGC AGA AGC AGA

        4599         4608         4617         4626         4635         4644
CAG GCT GTT TCT TTG ACA CAA ATA TCA CAG GCT TCA GGG TTA AGA TTG CTG TTT

        4653         4662         4671         4680         4689         4698
TTC TGT CCT TGC TTT GGC ACA ACA CAC TGA GGG TTT TTT TTA TTG CGG GTT TGC

        4707         4716         4725         4734
CTA CAG GTA GAT TAG ATT AAT TAT TAC TAT GTA ATG CAA GT 3'
```

```
p160  MSTGDSFETRFEKMDNLLRDPKSEVNSDCLLDGLDALVYDLDFPALRKNK   50
MDPK  MSA----EVRLRRLQCLVLDP-GFLGLEPLLDLLLGVHQELGASELAQDK   45

p160  NIDNFLSRYKDTINKIRDLRMKAEDMEVVKVIGRGAFGEVQLVRHKSTRK  100
MDPK  YVADFLQWAEPIVVRLKEVRLQRDDEEILKVIGRGAFSEVAVVKMKCTGQ   95

p160  VYAMKLLSKFEMIKRSDSAFFWEERDIMAFANSPWVVQLFYAFQDDPYLY  150
MDPK  VYAMKIMNKWDMIKRGEVSCFFEERDVLVNGDRPWITQLHFAFQDENYLY  145

p160  MVMEYMPGGDLVNLMSNYD--VPEKWARFYTAEVVLALDAIHSMGFIHRD  198
MDPK  LVMEYYVGGDLLTLLSKFGERIPAEMARFYLAEIVMAIDSVHRLGYVHRD  195

p160  VKPDNMLLDKSGHLRLADFGTCMKMNKEGMVRCDTAVGTPDYISPEVLKS  248
MDPK  IKPDNILLDRCGHIRLADFGSCLKLRADGTVRSLVAVGTPDYLSPEILQA  245

p160  CGGD---GYYGPECDWWSVGVFLYEMLVGDTPFYADSLVGTYSKIMNHKN  295
MDPK  VGGGPGTGSYGRECDWWALGVFPYEMFYGCTPFYADSTAETYGKIVHYKE  295

p160  SLTFPDDND-ISMEAKNLICAFLTDPEMRLGRNGVEEIKPHLFFKNDQWA  344
MDPK  HLSLPLVDEGVPEEARDFIQRLLCPPEIRLGRGGAGDFRTHPFFFG--LD  343

p160  WETLRDIVMPVVPCLSSDIDTSNFDDLEEDKGEEETFP-IPK-AFVGNCL  392
MDPK  WDGLRDSVPPFTPCFEGATDTCNFDLVEDGLTAMETLSDIREGAPLGVHL  393

p160  PFVGFTYYSNRRYLSSANPNDNRTSSNA                        420
MDPK  PFVGYS-YSCMALRDSEVPGPTPMELEA                        420
```

FIG. 25

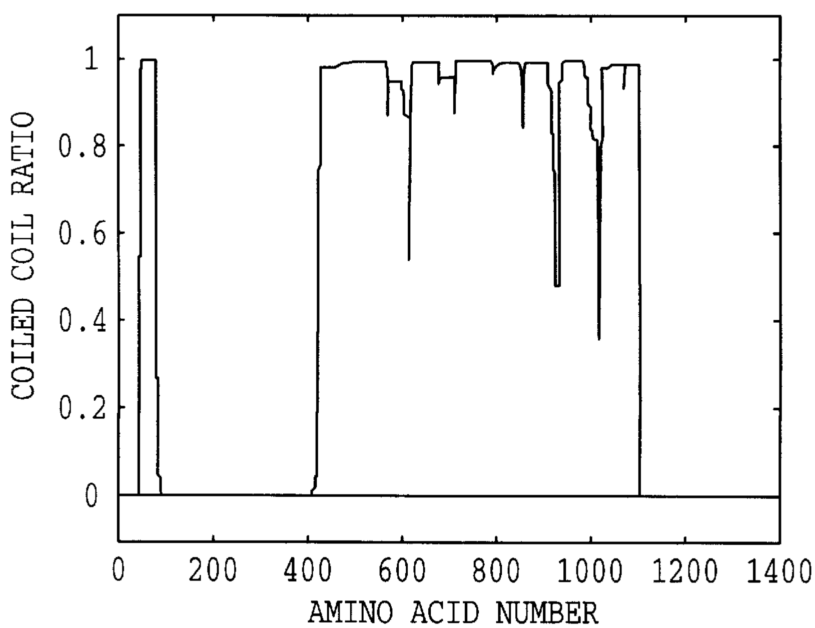

FIG. 26

```
p160      1113  DGILPESRIE GWLSVPNRGN IKRYGWKKCY VVVSS--KKI  1150
Ras GAP    475  DAFYKNIVKK GYLLKKGKG- ---KRWKNLY FILEGSDAQL   510
Vav        397  LANYGRPKID GELKITSVE- --RRSKTDRY AFLLD--KAL   431

p160      1151  LFYNDEQDKE QSNPSMVLDI DKLFHVRPVT QGDVYRAETE  1190
Ras GAP    511  IYFESE--KR ATKPKGLIDL SVCSVYVVHD SLFGR-----   543
Vav        432  LICKRR--GD SYDLKASVNL HSFQVRDDSS GERDN----K   466

p160      1191  EIPKIFQILY ANEGECRKDV   < 70 >   CPCKVSYDVT  1290
Ras GAP    544  --PNCFQIVV QHFS------ ---------- ---------E   556
Vav        467  KWSHMFLLIE DQGA------ ---------- ----------   489

p160      1291  SARDMLLLAC SQDEQKKWVT HLVKKIPKN.             1319
Ras GAP    557  EHYIFYFAGE TPEQAEDWMK GLQAFCNLR.              585
Vav        490  --QGYELFFK TRELKKKWME QFEMAISNI.              516
```

FIG. 27

```
p160        1229  HEFIPTLYHFPANCDACAKPLWHVPFPPPALECRRCHVKCHRDHLDKKEDLIC  1281
PKC DELTA    109  HEFTATFFGCPTPCSVCKEFVWGLNF--QGYRCRCCNAAIHKKCIDKIIG-RC   158
```

FIG. 28

```
920          934         946                         974                           1005      1015
|             |      #    | #      #      #           |                              |         |
SKKAASRNRQEITDKDHTVSRLEEANSMLTKDIEILRRENEELTEKMKKAEEEYKLEKEEEISNLKAAFEKNINTERTLKTQAVNKLAEIMNRKDF
*    *   *    *      * *       *        *                            *     *   *        **  **
M    A   A    M      A A       A        A                            A     Q   M        AA  LM
```

FIG. 37

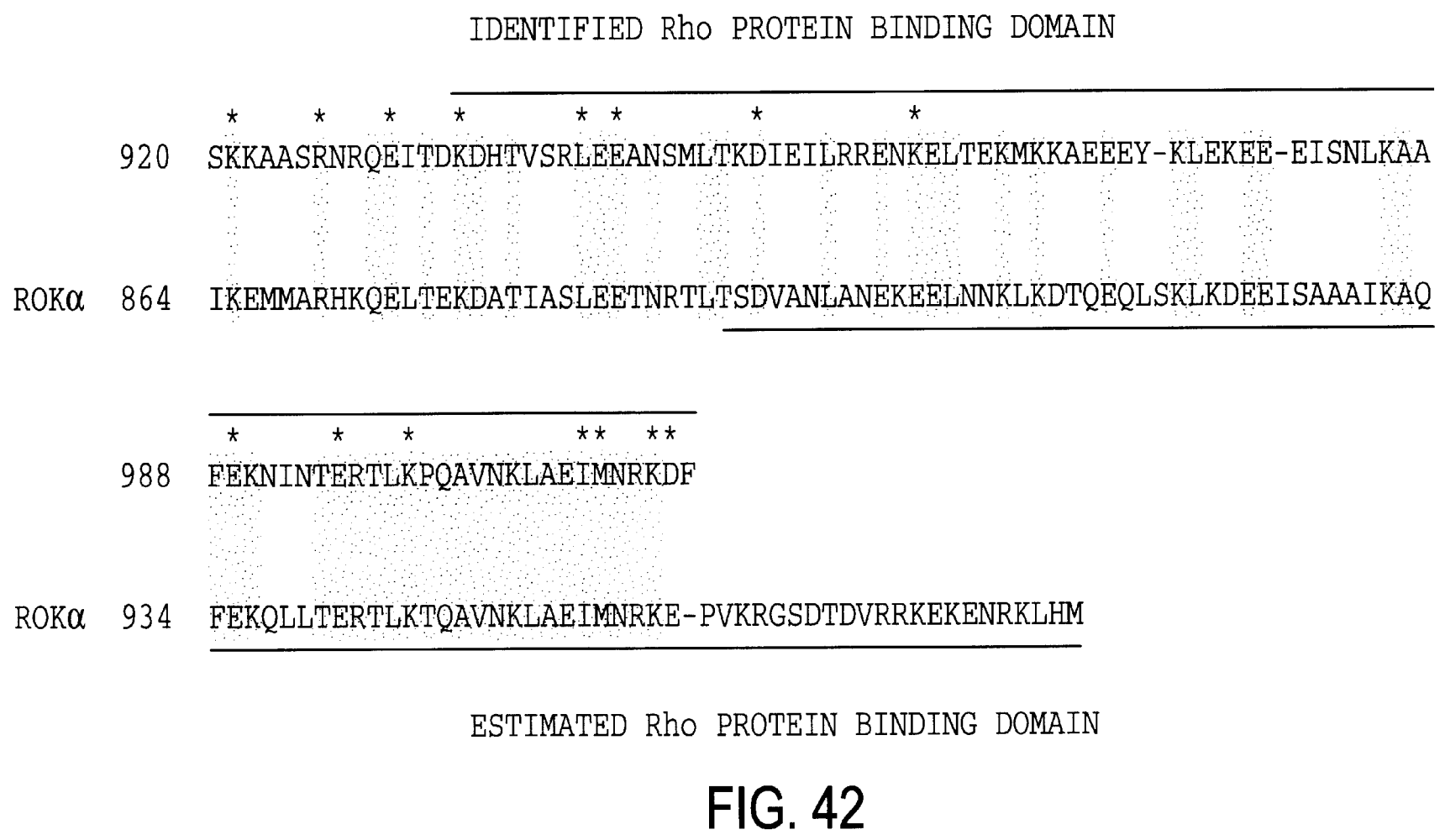

IDENTIFIED Rho PROTEIN BINDING DOMAIN

```
       920  SKKAASRNRQEITDKDHTVSRLEEANSMLTKDIEILRRENKELTEKMKKAEEEY-KLEKEE-EISNLKAA
ROKα   864  IKEMMARHKQELTEKDATIASLEETNRTLTSDVANLANEKEELNNKLKDTQEQLSKLKDEEISAAAIKAQ

       988  FEKNINTERTLKPQAVNKLAEIMNRKDF
ROKα   934  FEKQLLTERTLKTQAVNKLAEIMNRKE-PVKRGSDTDVRRKEKENRKLHM
```

ESTIMATED Rho PROTEIN BINDING DOMAIN

FIG. 42

RHO TARGET PROTEIN KINASE P160

FIELD OF THE INVENTION

The present invention relates to a novel protein having activated Rho protein binding activity.

BACKGROUND OF THE INVENTION

A group of low-molecular-weight GTP-binding proteins (G-proteins) with molecular weights of 20,000–30,000 with no subunit structures is observed in organisms. To date, over fifty or more members have been found as the super family of the low-molecular-weight G-proteins in a variety of organisms, from yeast to mammals. The low-molecular-weight G-proteins are divided into four families of Ras, Rho, Rab and the others based on homologies of amino acid sequences. It has been revealed that the small G-proteins control a variety of cellular functions. For example, the Ras protein is considered to control cell proliferation and differentiation, and the Rho protein is considered to control cell morphological change, adhesion and motility.

The Rho protein, having GDP/GTP-binding activity and intrinsic GTPase activity, is believed to be involved in cytoskeletal responses to extracellular signals such as lysophosphatidic acid (LPA) and certain growth factors. When the inactive GDP-binding Rho is stimulated, it is transformed to the active GTP-binding Rho protein (hereinafter referred to as "the activated Rho protein") by GDP/GTP exchange proteins such as Smg GDS, Dbl or Ost. The activated Rho protein then acts on target proteins to form stress fibers and focal contacts, thus inducing the cell adhesion and motility (Experimental Medicine, Vol. 12, No. 8, 97–102 (1994); Takai, Y. et al., Trends Biochem. Sci., 20, 227–231 (1995)). On the other hand, the intrinsic GTPase activity of the Rho protein transforms the activated Rho protein to the GDP-binding Rho protein. This intrinsic GTPase activity is enhanced by what is called GTPase-activating proteins (GAP) (Lamarche, N. & Hall, A. et al., TIG, 10, 436–440 (1994)).

The Rho family proteins, including RhoA, RhoB, RhoC, Rac1, Rac2 and Cdc42, share more than 50% sequence identity with each other. The Rho family proteins are believed to be involved in inducing the formation of stress fibers and focal contacts in response to extracellular signals such as lysophosphatidic acid (LPA) and growth factors (A. J. Ridley & A. Hall, Cell, 70, 389–399 (1992); A. J. Ridley & A. Hall, EMBO J., 1353, 2600–2610 (1994)). The subfamily Rho is also considered to be implicated in physiological functions associated with cytoskeletal rearrangements, such as cell morphological change (H. F. Parterson et al., J. Cell Biol., 111, 1001–1007 (1990)), cell adhesion (Morii, N. et al., J. Biol. Chem., 267, 20921–20926 (1992); T. Tominaga et al., J. Cell Biol., 120, 1529–1537 (1993); Nusrat, A. et al., Proc. Natl. Acad. Sci. USA, 92, 10629–10633 (1995)*; Landanna, C. et al., Science, 271, 981–983 (1996)*, cell motility (K. Takaishi et al., Oncogene, 9, 273–279 (1994), and cytokinesis (K. Kishi et al., J. Cell Biol., 120, 1187–1195 (1993); I. Mabuchi et al., Zygote, 1, 325–331 (1993)). (An asterisk hereinafter indicates a publication issued after the first filed application which provides the right of the priority of the present application.) In addition, it has been suggested that the Rho is involved in the regulation of smooth muscle contraction (K. Hirata et al., J. Biol. Chem., 267, 8719–8722 (1992); M. Noda et al., FEBS Lett., 367, 246–250 (1995); M. Gong et al., Proc. Natl. Acad. Sci. USA, 93, 1340–1345 (1996)*), and the expression of phosphatidylinositol 3-kinase (PI3 kinase) (J. Zhang et al., J. Biol. Chem., 268, 22251–22254 (1993)), phosphatidylinositol 4-phosphate 5-kinase (PI 4,5-kinase) (L. D. Chong et al., Cell, 79, 507–513 (1994)) and c-fos (C. S. Hill et al., Cell, 81, 1159–1170 (1995)).

Recently, it has also be found that Ras-dependent tumorigenesis is suppressed when the Rho protein of which the amino acid sequence has been partly substituted is introduced to cells, revealing that the Rho protein plays an important role in Ras-induced transformation, that is, tumorigenesis (G. C. Prendergast et al., Oncogene, 10, 2289–2296 (1995); Khosravi-Far, R. et al., Mol. Cell. Biol., 15, 6443–6453 (1995)*; R. Qiu et al., Proc. Natl. Acad. Sci. USA, 92, 11781–11785 (1995)*; Lebowitz, P. et al., Mol. Cell, Biol., 15, 6613–6622 (1995)*).

It has also been demonstrated that mutation of GDP/GTP-exchange proteins which act on the Rho protein results in cell transformation (Collard, J., Int. J. Oncol., 8, 131–138 (1996)*; Hart, M. et al., J. Biol. Chem., 269, 62–65 (1994); Horii, Y. et al., EMBO J., 13, 4776–4786 (1994)).

In addition, the Rho protein has been elucidated to be involved in cancer cell invasion, that is, metastasis (Yoshioka, K. et al., FEBS Lett., 372, 25–28 (1995)). The cancer cell invasion is closely dependent on changes in cancer cell activity to form cell adhesion. In this context, the Rho protein is also known to be involved in the formation of cell adhesion (see above Morii, N. et al. (1992); Tominaga, T. et al. (1993); Nusrat, A. et al. (1995); Landanna C. et al. (1996)*).

It has also been revealed that the Rho protein enhances not only cell proliferation, motility and aggregation, but also the contraction of smooth muscles. Recent studies have demonstrated that the Rho protein is involved in the contraction of smooth muscles (K. Hirata et al., J. Biol. Chem., 267, 8719–8722 (1992); Noda, M. et al., FEBS Lett., 367, 246–250 (1995)). Therefore, it can reasonably be assumed that the activated Rho protein-binding proteins are also involved in the contraction of smooth muscles.

These findings indicate that the Rho protein controls a variety of signal transduction pathways for cell morphological change, adhesion, motility, cytokinesis, tumorigenesis, metastasis, vascular smooth muscle contraction, etc. The Rho protein acts on a number of target molecules to control signal transduction pathways.

It is only recently (after the first filed application which provides the right of the priority of the present application) that a several proteins have been reported as candidates of Rho-targets in mammals: protein kinase N (PKN) (Watanabe, G. et al., Science, 271, 645–648 (1996)*; Amano, M. et al., Science, 271, 648–650 (1996)*), rhophilin (Watanabe, G. et al., Science, 271, 645–648 (1996)*, citron (Madaule, P. et al., FEBS Lett., 377, 243–248 (1995)*), ROKα (Leung, T. et al., J. Biol. Chem., 270, 29051–29054 (1995)*), Rho-binding kinase (Matsui, T. et al., EMBO J., 15, 2208–2216 (1996)*) and rhotekin (Reid, T. et al., J. Biol. Chem., 271, 13556–13560 (1996)*). All these proteins bind to GTP-binding RhoA protein, except that citron binds also to GTP-binding Racl.

Among these proteins, PKN has an enzymatic region which closely resembles the protein kinase region of protein kinase C and exhibits serine/threonine kinase activity (Mukai, H. & Ono, Y., Biochem. Biopys. Res. Commun., 199, 897–904 (1994); Mukai, H. et al., Biochem. Biopys. Res. Commun., 204, 348–356 (1994)). On the other hand, ROKα and Rho-binding kinase (Matsui, T. et al. (1996)*, ibid.) also have amino acid sequences resembling a serine/threonine kinase region (Leung, T. et al. (1995)*, ibid.).

In addition to those reported in mammals, protein kinase C1 (PKC1) in yeast (Saccharomyces cerevisiae) has recently been identified as a target protein of the Rho1 protein, corresponding to RhoA in mammals (Nonaka, H. et al., EMBO J., 14, 5931–5938 (1995)*). Only recently, 1,3-β-glucan synthesizing enzyme has been identified as a target protein of the Rholp protein in yeast (Saccharomyces cerevisiae) (Drgonova, J. et al., Science, 272, 277–279 (1996)*; Qadota, H. et al., Science, 272, 279–281 (1996)*).

However, mechanisms of intercellular signal transduction involving the activated Rho protein, particularly those of tumorigenesis and smooth muscle contraction, are still unknown.

SUMMARY OF THE INVENTION

The inventors have isolated a protein having activated Rho A binding activity from human blood platelets. Also, the inventors have identified the Rho-binding region and protein kinase region of the protein. The present invention is based on these findings.

An object of the present invention is thus to provide a protein having the activated Rho protein binding activity and/or protein kinase activity.

Another object of the present invention is to provide a nucleic acid sequence encoding the protein, a vector comprising the base sequence, a host cell transformed by the vector, a process for producing the protein, and a method for screening a material inhibiting binding between the activated Rho protein and its target proteins.

The present invention thus is a protein having the activated Rho protein binding activity and protein kinase activity.

BRIEF DESCRIPTION OF THE DRAWINGS

FIG. 1 shows the deduced amino acid sequence of p160 (SEQ ID NO:2). Thick and thin underlines indicate AP-23 peptide and other partial amino acid sequences, respectively. Asterisks indicate leucine residues in a leucine zipper-like sequence.

FIG. 2 shows the nucleic acid sequence encoding p160 and the corresponding amino acid sequence (SEQ ID NOS:1 and 2). FIGS. 2–10 illustrate a set of the nucleic acid sequence and amino acid sequence.

FIG. 3 is a continuation of FIG. 2, showing the nucleic acid sequence encoding p160 and the corresponding amino acid sequence.

FIG. 4 is a continuation of FIG. 3, showing the nucleic acid sequence encoding p160 and the corresponding amino acid sequence.

FIG. 5 is a continuation of FIG. 4, showing the nucleic acid sequence encoding p160 and the corresponding amino acid sequence.

FIG. 6 is a continuation of FIG. 5, showing the nucleic acid sequence encoding p160 and the corresponding amino acid sequence.

FIG. 7 is a continuation of FIG. 6, showing the nucleic acid sequence encoding p160 and the corresponding amino acid sequence.

FIG. 8 is a continuation of FIG. 7, showing the nucleic acid sequence encoding p160 and the corresponding amino acid sequence.

FIG. 9 is a continuation of FIG. 8, showing the nucleic acid sequence encoding p160 and the corresponding amino acid sequence.

FIG. 10 is a continuation of FIG. 9, showing the nucleic acid sequence encoding p160 and the corresponding amino acid sequence.

FIG. 25 shows alignment of the amino acid sequences of p160 to myotonic dystrophy kinase (MD-PK) (SEQ ID NOS:58 and 59, respectively).

FIG. 26 shows an analytical result of coiled-coil region of p160.

FIG. 27 shows alignment of the amino acid sequences of p160 to PH region (SEQ ID NOS:60–62, respectively).

FIG. 28 shows alignment of the amino acid sequences of p160 to cystein-rich region (SEQ ID NOS:63 and 64, respectively).

FIG. 37 shows positions of point mutations in M2-10 (906–1024) as asterisks. Other truncation mutants (M2-2 to M2-9) are shown above the sequence (SEQ ID NO:65). Leucine zippers are indicated by #.

FIG. 42 shows comparison of the putative RhoA-binding domains of p160 and ROKα (SEQ ID NOS:65 and 66, respectively). The Rho-binding domain identified in p160 and that proposed in ROKα are indicated by thick lines. Conserved amino acids are indicated by shaded areas. An asterisk indicates positions of point mutation. The sequence of ROKα is from Leung, T. et al., J. Biol. Chem., 270, 29051–29054 (1995).

DETAILED DESCRIPTION OF THE INVENTION

Definition

Figure 11:
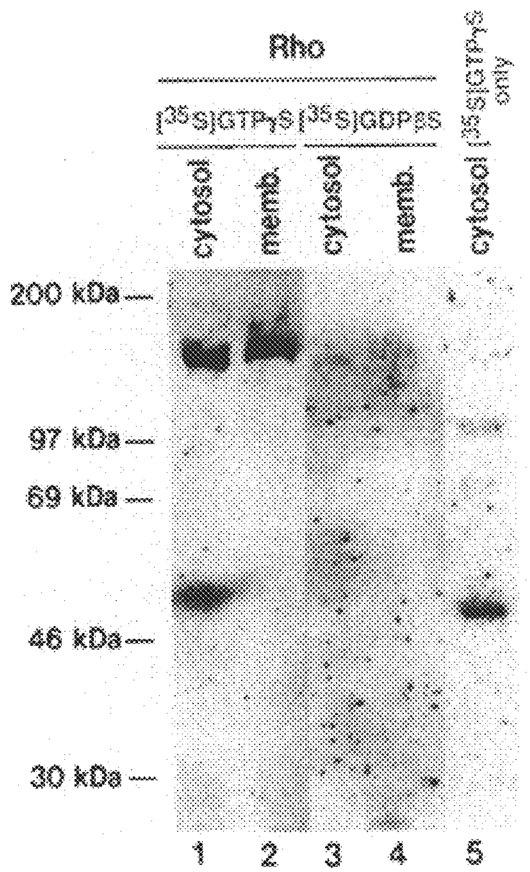
FIG. 11 is an electrophoretic photograph showing the identification of the activated Rho protein binding protein in human blood platelets by the ligand overlay assay. Lanes 1 and 2: $[^{35}S]$GTPγS-Rho. Lanes 3 and 4: $[^{35}S]$ GDPβS-Rho. Lane 5: $[^{35}S]$GTPγS.

The term "amino acid" herein refers to the meaning including either of optical isomers, i.e., an L-isomer and a D-isomer. Thus, the term "peptide" herein refers to the meaning including not only peptides constituted by L-amino acids solely but also peptides comprising D-amino acids partially or totally.

Furthermore, the term "amino acid" herein refers to the meaning including not only twenty α-amino acids which constitute natural proteins but also other α-amino acids as well as β-, γ- and δ-amino acids, non-natural amino acids, and the like. Thus, amino acids with which peptides are substituted or amino acids inserted into peptides as shown below are not restricted to twenty α-amino acids which constitute natural proteins but may be other α-amino acids as well as β-, γ- and δ-amino acids, non-natural amino acids, and the like. Such β-, γ- and δ-amino acids include β-alanine, γ-aminobutyric acid or ornithine. In addition, the amino acids other than those constituting natural proteins or the non-natural amino acids include 3,4-dihydroxyphenylalanine, phenylglycine, cyclohexylglycine, 1,2,3,4-tetrahydroisoquinolin-3-carboxylic acid or nipecotinic acid.

The term "protein according to the present invention" refers to the meaning including derivatives of the proteins.

The term "base sequence" herein refers to RNA sequences as well as DNA sequences.

Parenthesized figures that follow symbols such as KD, M1, M2, M3 and C herein indicate a region of the amino acid sequence of SEQ ID NO: 2. For example, KD (2-333) refers to the amino acid sequence 2-333 in SEQ ID NO: 2.

A position of mutation in a mutant protein is indicated by referring to the amino acid residue before mutation (one letter), the position of the amino acid to be substituted, and the amino acid residue after mutation (one letter). For example, "K921M (906-926)" means the amino acid sequence 906-926 in SEQ ID NO: 2, in which the amino acid residue 921, K (Lys: lysine), is substituted by M (Met: methionine).

Protein

The protein of the present invention is a protein having the activated Rho protein binding activity and protein kinase activity or derivatives thereof. The Rho protein includes the RhoA protein, the RhoB protein, the RhoC protein and RhoG protein.

In the present invention, the term "protein having the activated Rho protein binding activity" means a protein which is evaluated by one skilled in the art to bind to the activated Rho protein, e.g., proteins which are evaluated to bind to the activated Rho protein when examined under the same condition as in Example 1 and Examples 4–10.

In this specification, the Rho protein includes Rho proteins which has been modified -in such a manner that binding between the Rho protein and the protein according to the present invention is not substantially damaged. The modified proteins include an RhoA mutant (RhoA$^{Val14}$), in which the amino acid 14 is substituted by valine.

In the present invention, the term "protein having the protein kinase activity" means a protein which is evaluated by one skilled in the art to have protein kinase activity, e.g., proteins which are evaluated to have protein kinase activity when examined under the same condition as in Example 2.

The protein according to the present invention is characterized by the enhancement of its protein kinase activity as it binds to the activated Rho protein. The term "protein kinase activity" refer to the meaning including serine/threonine kinase activity.

The protein according to the present invention is not specifically restricted to any sources but it may be derived from mammals including human being, or any other sources.

The molecular weight of the protein according to the present invention is about 160 kD as measured by SDS-PAGE.

The protein according to the present invention can be obtained, for example, by the method described in Example 1 (2).

The term "derivatives of proteins" herein includes proteins in which an amino group at an amino terminal (N-terminal) or all or a part of amino groups of side chains of amino acids, and/or a carboxyl group at a carboxyl terminal (C-terminal) or all or a part of carboxyl groups of side chains of amino acids, and/or functional groups other than the amino groups and carboxyl groups of the side chains of the amino acids such as hydrogen, a thiol group or an amido group have been modified by appropriate other substituents. The modification by the appropriate other substituents is carried out in order to, for example, protect functional groups in the protein, improve safety and tissue-translocation of the protein or enhance the protein activity.

The derivatives of the proteins include:

(1) proteins in which one or more hydrogen atoms of the amino group at the amino terminal (N-terminal) or a part or all of the amino groups of the side chains of the amino acids are replaced by substituted or unsubstituted alkyl groups (which may be straight chain or branched chain or cyclic chain) such as a methyl group, an ethyl group, a propyl group, an isopropyl group, an isobutyl group, a butyl group, a t-butyl group, a cyclopropyl group, a cyclohexyl group or a benzyl group, substituted or unsubstituted acyl groups such as a formyl group, an acetyl group, a caproyl group, a cyclohexylcarbonyl group, a benzoyl group, a phthaloyl group, a tosyl group, a nicotinoyl group or a piperidincarbonyl group, urethane-type protective groups such as a p-nitrobenzyloxycarbonyl group, a p-methoxybenzyloxycarbonyl group, a p-biphenylisopropyl-oxycarbonyl group or a t-butoxycarbonyl group, or urea-type substituents such as a methylaminocarbonyl group, a phenylcarbonyl group or a cyclohexylaminocarbonyl group;

(2) proteins in which the carboxyl groups at the carboxyl terminal (C-terminal) or a part or all of the side chains of the amino acids are esterified (for example, the hydrogen atom(s) are replaced by methyl, ethyl, isopropyl, cyclohexyl, phenyl, benzyl, t-butyl or 4-picolyl), or amidated (for example, unsubstituted amides or C1–C6 alkylamide such as an methylamide, an ethylamide or an isopropylamide are formed); or (3) proteins in which a part or all of the functional groups other than the amino groups and the carboxyl groups of the side chains of the amino acids such as hydrogen, a thiol group or an amino group are replaced by the substituents described in (1) or a trityl group.

Examples of the protein according to the present invention include proteins consisting of the amino acid sequence of SEQ ID NO: 2 (hereinafter referred to as "p160") and derivatives thereof. The amino acid sequence of SEQ ID NO: 2 was determined based on the cDNA sequence, i.e., the DNA sequence obtained from the cDNA library from human megakaryocytic leukemia cell (Hirata, M. et al., Nature, 349, 617–620 (1991); Ogura, M. et al., Blood, 66, 1384–1392 (1985)). The cDNA library can be prepared according to a previously described method (Kakizuka, M. et al., Nature, 349, 617–620 (1991)). The cDNA sequence can also be obtained using the oligonucleotide corresponding to the peptide AP-23 shown in FIG. 1 as a probe.

Other examples of the protein according to the present invention include proteins consisting of the amino acid sequence of SEQ ID NO: 2 and having the activated Rho protein binding activity and protein kinase activity wherein one or more amino acid sequences are added or inserted in the amino acid sequence of SEQ ID NO: 2 and/or one or more amino acids in the amino acid sequence of SEQ ID NO: 2 are substituted and/or deleted. The terms "addition", "insertion", "substitution" and "deletion" refer to those that do not damage the activated Rho protein binding activity and protein kinase activity of the protein consisting of the amino acid sequence of SEQ ID NO: 2.

Examples of such substitutions include: K921M, R926A, E930A, E943A, D951A, E960A, E989A, E995A, K999M, R1012L and K1013M.

Examples of the protein having the activated Rho protein binding activity and protein kinase activity which contain one of the above substitutions include K921M (1-1354) and R926A (1-1354).

Examples of the protein having the activated Rho protein binding activity and protein kinase activity which contain two or more of the above substitutions include K921M·R926A (1-1354).

Examples of such deletions include deletions of all or part of the amino acid sequence of SEQ ID NO: 2 except the amino acid sequence 72-343 (protein kinase region) and the amino acid sequence 920-1015 (Rho-binding region); more specifically, the deletion of the amino acid sequence 1016-1354 or a part thereof (e.g., 1022-1354 or 1025-1354), the amino acid sequence 344-933 or a part thereof (e.g., 344-726, 344-846, 344-905 or 344-919), or the amino acid sequence 1-71 or a part thereof.

According to another aspect of the present invention, we provide a protein having the amino acid sequence 72-343 (protein kinase region) and amino acid sequence 920-1015 (Rho-binding region) in SEQ ID NO: 2.

According to the present invention, we also provide a protein having the activated Rho protein binding activity and not having the protein kinase activity, or derivatives thereof.

Examples of the above protein include proteins consisting of the amino acid sequence of SEQ ID NO: 2 and having the activated Rho protein binding activity and not having protein kinase activity wherein one or more amino acid sequences are added or inserted in the amino acid sequence of SEQ ID NO: 2 and/or one or more amino acids in the amino acid sequence of SEQ ID NO: 2 are substituted and/or deleted. The terms "addition", "insertion", "substitution" and "deletion" refer to those that do not damage the activated Rho protein binding activity and damage the protein kinase activity of the protein consisting of the amino acid sequence of SEQ ID NO: 1.

Examples of such deletions include deletions of all or part of the amino acid sequence 72-343 (protein kinase region) in SEQ ID NO: 2 or all or part of a region necessary for the protein kinase activity.

Also, a protein or derivatives thereof consisting of the amino acid sequence of SEQ ID NO: 2 (having an addition, insertion, substitution and/or deletion) having the activated Rho protein binding activity and not having protein kinase activity may contain, in addition to the above addition, insertion, substitution and/or deletions, other additions, insertions, substitutions and/or deletions that do not damage the Rho protein binding activity of the protein.

Examples of such deletions include deletions of all or part of the amino acid sequence of SEQ ID NO: 2 except the amino acid sequence 934-1015 (Rho-binding region); more specifically, the deletion of the amino acid sequence 1015-1354 or a part thereof (e.g., 1021-1354 or 1024-1354), the amino acid sequence 344-933 or a part thereof (e.g., 344-726, 344-846, 344-905 or 344-919), or the amino acid sequence 1-71 or any part of it.

Also, examples of such substitutions include K921M, R926A, E930A, E943A, D951A, E960A, E989A, E995A, K999M, R1012L and K1013M.

Examples of proteins having the activated Rho protein binding activity and not having protein kinase activity which contain both the substitution and deletion as described above include K921M (906-1094), R926A (906-1094), and K921M·R926A (906-1094).

According to another aspect of the present invention, we also provide a protein comprising the amino acid sequence 934-1015 in SEQ ID NO: 2 at least (e.g., a protein consisting of the amino acid sequence 727-1021, 847-1024, 906-1024, 920-1024, 906-1015, 920-1015 or 906-1094 in SEQ ID NO: 2) or derivatives thereof. The protein has the activated Rho protein binding activity and does not have protein kinase activity.

According to the present invention, we provide a protein having the protein kinase activity and not having the activated Rho protein binding activity, or derivatives thereof. The term "protein kinase activity" refers to the meaning including serine/threonine kinase activity.

Examples of the above protein include proteins consisting of the amino acid sequence of SEQ ID NO: 2 having the protein kinase activity and not having the activated Rho protein binding activity wherein one or more amino acid sequences are added or inserted in the amino acid sequence of SEQ ID NO: 2 and/or one or more amino acids in the amino acid sequence of SEQ ID NO: 2 are substituted and/or deleted. The terms "addition", "insertion", "substitution" and "deletion" refer to those that does not damage the protein kinase activity and damage the activated Rho protein binding activity of the protein consisting of the amino acid sequence of SEQ ID NO: 2.

Examples of such deletions include deletions of all or part of the amino acid sequence 934-945 or 1005-iO15 in SEQ ID NO: 2 or all or part of a region having the activated Rho protein binding activity.

Also, examples of the above substitution include K934M, L941A, E1008A and I1009A.

Also, a protein or derivatives thereof consisting of the amino acid sequence of SEQ ID NO: 2 (containing an addition, insertion, substitution and/or deletion) having protein kinase activity and not having the activated Rho protein binding activity may contain, in addition to the above addition, insertion, substitution and/or deletion, other additions, insertions, substitutions and/or deletions that do not damage the protein kinase activity of the protein.

Examples of such deletions include deletions of all or part of the amino acid sequence of SEQ ID NO: 2 except for the amino acid sequence 72-343 (protein kinase region); more specifically, the deletion of the amino acid sequence 1-71 or a part thereof or the amino acid sequence 344-1354 or a part thereof.

According to another aspect of the present invention, we provide a protein comprising, at least, the amino acid sequence 72-343 of SEQ ID NO: 2 or derivatives thereof. The protein has protein kinase activity and does not have the activated Rho protein binding activity. Examples of such proteins include I1009A (1-1354).

Leung, T. et al., J. Biol. Chem., 270, 29051–29054 (1995)*, which was published after the first application which provides the right of the priority of the present application, reports an Rho protein binding protein, i.e., one of the isozyme of p160 (ROKα), cloned from a rat brain cDNA library. The study implies that the Rho binding fragment of ROKα covers the amino acid sequence 893-982 of ROKα, which corresponds to the amino acid sequence 949-1039 in SEQ ID NO: 2.

The comparison of the amino acid sequences of these two isozymes are shown in FIG. 42. According to FIG. 42, the Rho protein binding region of p160 (i.e., a modified protein of the present invention) differs from the Rho protein binding region of ROKα reported in the above reference.

According to the present invention, we provide a protein consisting of a part of the amino acid sequence of SEQ ID NO: 2 and containing any one of a leucine zipper-like sequence, a coiled-coil region, a pleckstrin-homology region, and a zinc finger region, or derivatives thereof.

The protein according to the present invention is a protein having the activated Rho protein binding activity and protein kinase activity, or a protein modified by damaging either or both of these functions. The Rho protein is closely involved in cell functions such as cell morphology, cell motility, cell adhesion, and cytokinesis as well as in tumorigenesis and metastasis (see Takai, Y. et al.; G. C. Prendergast et al.; Khosravi-Far, R. et al.; R. Qiu et al.; Lebowitz, P. et al.; Yoshioka, K. et al., ibid.). Therefore, the protein according to the present invention is considered to be useful in elucidating the mechanisms of tumorigenesis and metastasis.

Also, Rho is known to be involved in smooth muscle contraction (see K. Hirata et al.; M. Noda et al., ibid.). Therefore, the protein according to the present invention is considered to be useful in elucidating the mechanisms of various cardiovascular diseases such as hypertension and vasospasm.

Nucleic Acid Sequence

According to the present invention, we provide a base sequence encoding protein according to the present invention. The typical sequence of this nucleic acid sequence has a part or all of the DNA sequence of SEQ ID NO: 1.

As mentioned above, the DNA sequence of SEQ ID NO: 1 was obtained from a cDNA library derived from human megakaryocytic leukemia cell. This DNA sequence corresponds to the open reading frame of p160.

This DNA sequence and the franking sequences are shown in FIGS. 2–10 (SEQ ID NOS:1 and 2). The open reading frame in this sequence starts at ATG (448-450) and ends at TAA (4510-4512).

When the amino acid sequence is given, the nucleic acid sequence encoding the amino acid sequence is easily determined, and a variety of base sequences encoding the amino acid sequence described in SEQ ID NO: 2 can be selected. The sequence encoding the protein according to the present invention thus means, in addition to a part or all of the DNA sequence described in SEQ ID NO: 1, another sequence encoding the same amino acid sequence and containing a DNA sequence of a degenerate codon(s), and also includes RNA sequences corresponding to the DNA sequences.

The nucleic acid sequence according to the present invention may be naturally occurred or obtained by synthesis. It may also be synthesized with a part of a sequence derived from the naturally occurring one. DNAs may typically be obtained by screening a chromosome library or a cDNA library in accordance with a conventional manner in the field of genetic engineering, for example, by screening a chromosome library or a cDNA library with an appropriate DNA probe obtained based on information of the partial amino acid sequence. The nucleic acid sequence according to the present invention can be obtained by preparing a cDNA library from human megakaryocytic leukemia cell MEG-01 (Ogura, M. et al., Blood, 66, 1384–1392 (1985)) according to the method described in Kakizuka, M. et al., Nature, 349, 617–620 (1991), and then by screening the library using the oligonucleotides corresponding to the peptide AP-23 shown in FIG. 1 as a probe.

The nucleic acid sequences from nature are not specifically restricted to any sources; but may be derived from mammals, including human, or other sources.

Examples of nucleic acid sequences encoding the protein according to the present invention include the sequence of SEQ ID NO: 1 and a part of the DNA sequence of SEQ ID NO: 1 (e.g., DNA sequence 214-1029, 2179-3063, 2539-3072, 2716-3072, 2539-3045, 2716-3045 or 2800-3045 in SEQ ID NO: 1).

Vector and Transformed Host Cell

According to the present invention, we provide a vector comprising the aforementioned nucleic acid sequence in such a manner that the vector can be replicable and express the protein encoded by the base sequence in a host cell. In addition, according to the present invention, we provide a host cell transformed by the vector. There is no other restriction to the host-vector system. It may express proteins fused with other proteins. Examples of the fusion protein expression system include those expressing MBP (maltose binding protein), GST (glutathione-S-transferase), HA (hemagglutinin), myc, Fas and the like.

Examples of the vector include plasmid vectors such as expression vectors for prokaryotic cells, yeast, insect cells or animal cells, virus vectors such as retrovirus vectors, adenovirus vectors, adeno-associated virus vectors, herpesvirus vectors, Sendai virus vectors or HIV vectors, and liposome vectors such as cationic liposome vectors.

The vector according to the present invention may contain, in addition to the base sequence according to the present invention, other sequences for controlling the expression and a gene marker for selecting host cells. In addition, the vector may contain the base sequence according to the present invention in a repeated form (e.g. tandem). The base sequences may also be introduced in a vector according to the conventional manner, and microorganisms or animal cultured cells may be transformed by the vector based on the method conventionally used in the field.

The vector according to the present invention may be constructed based on the procedure and manner which have been conventionally used in the field of genetic engineering.

Furthermore, examples of the host cell include Escherichia coli, yeast, insect cells, animal cells such as COS cells, lymphocytes, fibroblasts, CHO cells, blood system cells, tumor cells, and the like.

The transformed host cell is cultured in an appropriate medium, and the protein according to the present invention may be obtained from the cultured product. Thus, according to another embodiment of the present invention, we provide a process for preparing the protein according to the present invention. The culture of the transformed host cell and culture condition may be essentially the same as those for the cell to be used. In addition, the protein according to the present invention may be recovered from the culture medium and purified according to the conventional manner.

The present invention can be applied to the gene therapy of malignant tumors (e.g., leukemia cells, carcinoma cells in digestive tract, lung carcinoma cells, pancreas carcinoma cells, ovary carcinoma cells, uterus carcinoma cells, melanoma cells, brain tumor cells, etc.) by introducing a vector having the base sequence according to the present invention into cancer cells of an organism including human using an appropriate method to express the protein according to the present invention, i.e., by transforming the cancer cells of cancer patients.

Also, when the protein according to the present invention having the activated Rho protein binding activity and not having protein kinase activity is expressed in an organism including human, the protein binds to the activated Rho protein and, then, inhibits the binding of endogenous p160 to the activated Rho protein to intercept the signal transduction from the activated Rho protein to endogenous p160, thereby suppressing tumorigenesis or metastasis in which the Rho protein is involved.

As for vectors for gene therapy, see Fumimaro Takahisa, Experimental Medicine (extra edition), Vol. 12, No. 15 "Forefront of Gene therapy" (1994).

Use and Pharmaceutical Composition

As mentioned above, a protein having the activated Rho protein binding activity and not having protein kinase activity has a function to intercept the signal transduction from the activated Rho protein to endogenous p160 by binding to the activated Rho protein (by inhibiting the binding of endogenous p160 to the activated Rho protein). In the meantime, as mentioned above, the Rho protein is known to be closely involved in tumorigenesis or metastasis. According to the present invention, p160 receives signals from Rho. Therefore, p160 is also considered to be closely involved in tumorigenesis and metastasis. Thus, a protein having the activated Rho protein binding activity and not having protein kinase activity should be useful in suppressing tumorigenesis or metastasis.

Therefore, a protein having the activated Rho protein binding activity and not having protein kinase activity can be used as a suppressing agent of tumorigenesis or metastasis in which Rho is in involved, i.e., which depends on the signal transduction via the Rho protein (hereinafter referred to as a "tumorigenesis suppressing agent").

Examples of such tumorigenesis and metastasis include tumor formations in which Rho, other low-molecular-weight G-proteins (e.g., Ras, Rac, Cdc42, Ral, etc.), low-molecular-weight G-protein GDP/GTP-exchange proteins (e.g., Dbl, Ost, etc.), lysophosphatidic acid (LPA), receptor-type tyrosine kinase (e.g., PDGF receptor, EGF receptor, etc.), transcription regulating proteins (e.g., myc, p53, etc.), or various human tumor viruses are involved.

The tumorigenesis suppressing agent according to the present invention may be administered orally or parenterally (e.g. intramuscular injection, intravenous injection, subcutaneous administration, rectal administration, transdermal administration, nasal administration, and the like), preferably orally. The pharmaceutical agent may be administered to human beings and animals other than human being in a variety of dosage forms suited for oral or parenteral administration.

The tumorigenesis suppressing agents may be prepared in either of preparation forms including oral agents such as tablets, capsules, granules, powders, pills, grains, and troches, injections such as an intravenous injection and an intramuscular injection, rectal agents, fatty suppositories, and water-soluble suppositories depending on their intended uses. These preparations may be prepared according to methods well known in the art with conventional excipients, fillers, binding agents, wetting agents, disintegrants, surfacactants, lubricants, dispersants, buffering agents, preservatives, dissolution aids, antiseptics, flavors, analgesic agents and stabilizing agents. Examples of the non-toxic additives which can be used include lactose, fructose, glucose, starch, gelatin, magnesium carbonate, synthetic magnesium silicate, talc, magnesium stearate, methylcellulose, carboxymethylcellulose or a salt thereof, acacia, polyethylene glycol, syrup, vaseline, glycerine, ethanol, propylene glycol, citric acid, sodium chloride, sodium sulfite, sodium phosphate, and the like.

The content of the protein according to the present invention in a pharmaceutical agent varies depending on its dosage forms. The pharmaceutical generally contains about 0.1–about 50% by weight, preferably about 1–about 20% by weight, of the protein.

The dose of the protein for treatment of the tumorigenesis and metastasis may appropriately be determined in consideration of its uses and the age, sex and condition of a patient, and is desirably in the range of about 0.1–about 500 mg, preferably about 0.5–about 50 mg, per day for an adult, which may be administered once or divided into several portions a day.

The present invention provides a method for suppressing tumorigenesis or metastasis comprising introducing a protein having the activated Rho protein binding activity and not having protein kinase activity into cells in which tumors are formed or to which tumors may transfer. The effective dosage, the method and form of administration refer to those described for the tumorigenesis suppressing agents.

A base sequence encoding a protein having the activated Rho protein binding activity and not having protein kinase activity may be used to suppress tumorigenesis or metastasis, by transforming the target cells using the vector having the base sequence. In other words, the base sequence can be used as a gene therapic agent for suppressing tumorigenesis or metastasis.

Screening Method

The present invention provides a method for screening a material which inhibits the binding between the activated Rho protein and the protein according to the present invention having the activated Rho protein binding activity, comprising:

(1) placing a material to be screened in a screening system containing the activated Rho protein and the protein according to the present invention having the activated Rho protein binding activity; and (2) measuring the degree of inhibition of the binding between the activated Rho protein and the protein according to the present invention having the activated Rho protein binding activity.

Examples of the method for "measuring degree of inhibition of binding" include a method to measure the binding between the protein according to the present invention and recombinant GTPγS·GST-RhoA in a cell-free system by using glutathione Sepharose beads, a method to measure the binding between the protein according to the present invention and the Rho protein in a cell system (animal cells) by using immunoprecipitation and immunoblotting or by the two hybrid system (M. Kawabata, Experimental Medicine (in Japanese), 13, 2111–2120 (1995); A. B. Vojetk et al., Cell, 74, 205–214 (1993)). For example, the degree of the binding inhibition can be measured as described in example 1 (1) and (3) and examples 4–10. In this specification, the term "measuring degree of inhibition of binding" includes measuring the presence or absence of the binding.

The screening system may be either a cell system or a cell-free system. Examples of the cell system include yeast cells, COS cells, *E. coli*, insect cells, nematode cells, lymphocytes, fibroblasts, CHO cells, blood cells, and tumor cells.

The material to be screened includes, but is not limited to, for example, peptides, analogues of peptides, microorganism culture, and organic compounds.

The present invention also provides a method for screening a material inhibiting the protein kinase activity of the protein according to the present invention or derivatives thereof having protein kinase activity, comprising:

(1) placing a material to be screened in a screening system containing the protein according to the present invention having the protein kinase activity or derivatives thereof; and (2) measuring the degree of inhibition of the protein kinase activity of the protein according to the present invention having protein kinase activity or derivatives thereof.

The present invention also provides a method for screening a material which inhibits the protein kinase activity of the protein according to the present invention or derivatives thereof having the activated Rho protein binding activity and protein kinase activity or the enhancement of the activity, comprising:

(1) placing a material to be screened in a screening system containing the activated Rho protein and the protein according to the present invention having the activated Rho protein binding activity and protein kinase activity or derivatives thereof; and (2) measuring the degree of inhibition of the protein kinase activity of the protein according to the present invention having the activated Rho protein binding activity and protein kinase activity or derivatives thereof or the degree of inhibition of the enhancement of the activity.

Examples of the method for measuring "degree of inhibition of the protein kinase activity" or "degree of inhibition of the enhancement of the protein kinase activity" of the protein according to the present invention include methods to measure the degree of the autophosphorylation activity or activity to phosphorylate any other substrates, or the degree of the enhancement of the activities in the presence of the activated Rho protein. For example, the degree of inhibition of the enhancement of the protein kinase activity can be measured as described in examples 2 and 5. In this specification, measuring "degree of inhibition of the protein kinase activity" or "degree of inhibition of the enhancement of the protein kinase activity" includes measuring the presence or absence of the inhibition of the protein kinase activity or the presence or absence of the inhibition of the enhancement of the protein kinase activity.

The degree of inhibition of the protein kinase activity or the degree of inhibition of the enhancement of the protein kinase activity can be measured by using for example, histone as a substrate.

The screening system and the material to be screened may be determined as in the aforementioned screening method.

As mentioned above, the activated Rho protein is known to be closely involved in tumorigenesis, metastasis, and smooth muscle contraction. According to the present invention, p160 receives signals from the activated Rho protein. Therefore, p160 is also considered to be closely involved in tumorigenesis, metastasis, and smooth muscle contraction. Thus, the above screening methods may also be used as a method for screening tumorigenesis or metastasis suppressors or smooth muscle contraction suppressor.

EXAMPLE

The present invention is illustrated by following examples in detail but not restricted thereto.

Example 1

Identification and Purification of The Activated Rho Protein-Binding Protein (1) Identification of Rho-binding protein by ligand overlay assay Cell homogenate (100 μg protein each) or purified proteins were subjected to SDS-PAGE on 8% gels, and the separated proteins were transferred to nitrocellulose membranes (Schleicher & Schuell). The proteins on the membranes were denatured and renatured as previously described (Manser, E. et al., J. Biol. Chem., 267, 16025–16028 (1992); Manser, E. et al., Nature, 367, 40–46 (1994)), except that the renaturation was performed overnight at 4° C. in Dulbecco's phosphate buffered saline (PBS) containing 0.1% bovine serum albumin, 0.5 mM $MgCl_2$, 50 μM $ZnCl_2$, 0.1% Triton X-100 and 5 mM dithiothreitol.

A recombinant GST-RhoA protein (a recombinant protein in which RhoA and glutathione-S-transferase (GST) are fused) was prepared according to the method described in Morii, N. et al., J. Biol. Chem., 268, 27160–27163 (1993). The recombinant GST-RhoA was loaded with $[^{35}S]$GTPγS or $[^{35}S]$GDPβS (Dupont-New England Nuclear) by incubating 40 μM of recombinant RhoA with 100 μM of each nucleoside (1000 Ci/mmol) in 25 mM Tris-HCl, pH 7.5, containing 1 mM $MgCl_2$, 2 mM EDTA, 100 mM NaCl, 0.05% Tween 20 and 5 mM dithiothreitol at 30° C. for 30 min. The radioactivity bound to the recombinant RhoA was determined by filter assay as previously described (Morii, N. et al., J. Biol. Chem., 263, 12420–12426 (1988)). The radionucleoside-bound recombinant RhoA protein was then added to the renatured proteins at 5 nM, and the incubation was performed as previously described (Manser, E. et al., Nature, 367, 40–46 (1994)). The membrane was subsequently washed, dried and exposed to X-ray film for autoradiography. The result is shown in FIG. 11.

(2) Purification of Rho-binding protein

Human blood platelets were collected from the buffy coat fraction as described previously (Morii, N., J. Biol. Chem., 267, 20921–20926 (1992)). All of the subsequent procedures were performed at 4° C. Washed platelets from 100 units of blood were homogenized in a Potter-Elvehjem homogenizer in 100 ml of buffer A (10 mM Tris-HCl, pH 7.4, containing 1 mM dithiothreitol, 1 mM EDTA, 1 mM EGTA, 1 mM benzamidine hydrochloride, 1 μg/ml leupeptin, 1 μg/ml pepstatin A and 100 μM PMSF), and then centrifuged at 100,000×g for 60 min. The supernatant containing 970 mg of protein was applied to a DEAE-Sepharose CL-6B column (Pharmacia Biotech; bed volume, 70 ml) equilibrated with buffer A. The elution was performed with a linear gradient of 0–0.5 M NaCl in buffer A (total volume, 1200 ml). The activated Rho protein binding protein with a molecular weight of about 160 kD (hereinafter referred to as "p160") was recovered as a broad peak at 0.25 M NaCl.

Figure 12:
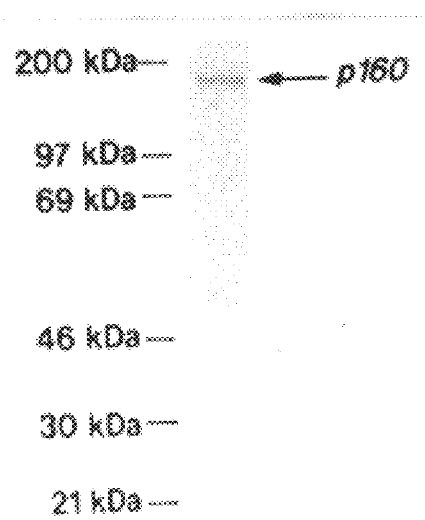
FIG. 12 is an electrophoretic photograph showing a result of p160 purification.

The Rho-binding fractions, containing 170 mg protein, were pooled and applied to a Red A Sepharose column (Amicon; bed volume, 7 ml) equilibrated with buffer A. The column was washed successively with 150 ml of buffer A containing 1 M NaCl, and then with 50 ml of buffer A containing 1.5 M NaCl. The elution was performed with 50 ml of the buffer A containing 1.5 M NaCl and 50% ethylene glycol. The recovered fraction (17.5 mg of protein) was dialyzed for 48 h against two changes of 1 l each of buffer A. The dialyzates were applied to 2 ml of a Macro-Prep ceramic Hydroxyapatite (grain size: 40 μm) column (Bio-Rad) equilibrated with buffer A, and the elution was performed with a linear gradient of 10–300 mM potassium phosphate, pH 7.0 (total volume, 90 ml). The Rho-binding fraction (0.75 mg of protein) was then applied to a Mono Q HR 5/5 column (Pharmacia Biotech), and the proteins were eluted with a linear gradient of 150–500 mM NaCl in a total volume of 35 ml. p160 was eluted in a broad peak at 350 mM NaCl, and this was designated as the final preparation. The result of purification is shown in FIG. 12.

Figure 13:
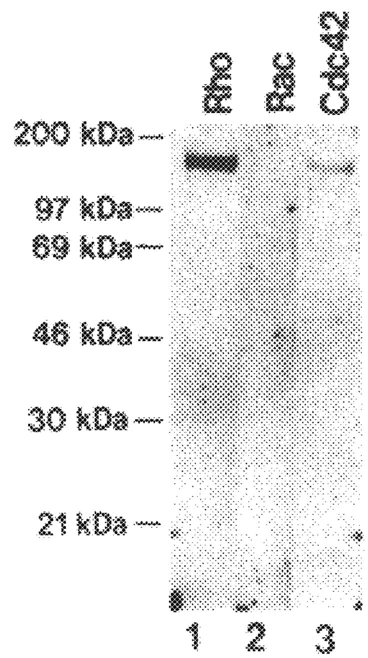
FIG. 13 is an electrophoretic photograph showing binding between p160 and the Rho subfamily proteins.

This preparation was applied to overlay assay with the RhoA protein, which had been loaded with $[^{35}S]$GTPγS according to the procedure mentioned above. The recombinant human RhoA protein, Rac1 protein and Cdc42Hs protein (fused with glutathione-S-transferase) used here were produced in *E. coli* according to a conventional method, then purified as described in Morii, N. et al., J. Biol. Chem., 268, 27160–27163 (1993). The result is shown in FIG. 13.

(3) Affinity precipitation using GST-RhoA

A hydroxyapatite fraction containing about 0.2 pmol of p160 was dialyzed against the overlay buffer containing 20 μM GTPγS or GDP. To this fraction was added recombinant GST-RhoA loaded with (i.e., containing) either 20 pM GTPγS or GDP, and the total volume was adjusted to 200 μl. Incubation was carried out at 4° C. for 60 min with gentle shaking.

Figure 14:
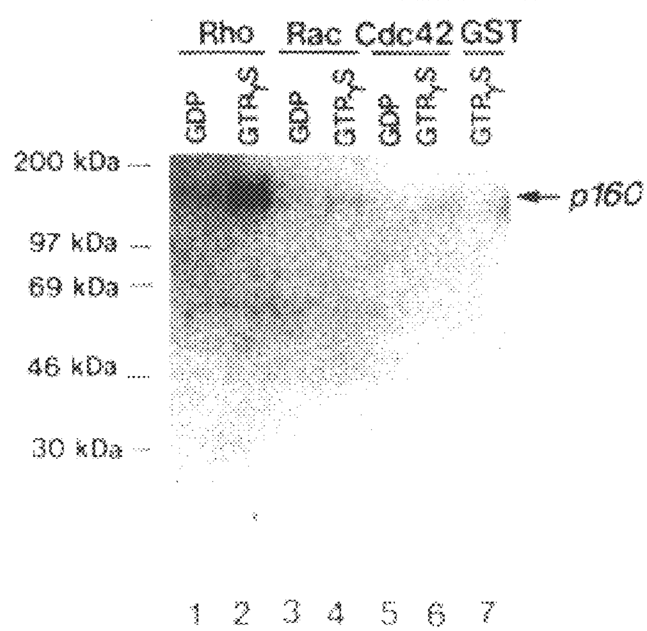
FIG. 14 is an electrophoretic photograph showing a result of an affinity precipitation experiment using GST-RhoA, GST-Rac, GST-Cdc42 and GST.

A 30 μl aliquot of GSH-Sepharose pre-equilibrated with the overlay buffer containing each nucleoside was then added, and the incubation continued for another 30 min at 4° C. The mixtures were centrifuged at 1000×g for 5 min The pellets were then washed twice with a washing buffer (25 mM MES-NaOH, pH 6.5, 150 mM NaCl, 5 mM $MgCl_2$, 0.05% Triton X-100, and 20 μM GTPγS or GDP). The Sepharose beads were then suspended in an equal volume of 2×Laemmli sample buffer. The suspensions were boiled and the extracts were subjected to the overlay assay as described above with GST-RhoA, GST-Rac, GST-Cdc42 and GST, which had been loaded with $[^{35}S]$GTPγS or GDP. The result is shown in FIG. 14.

Example 2

Figure 15:
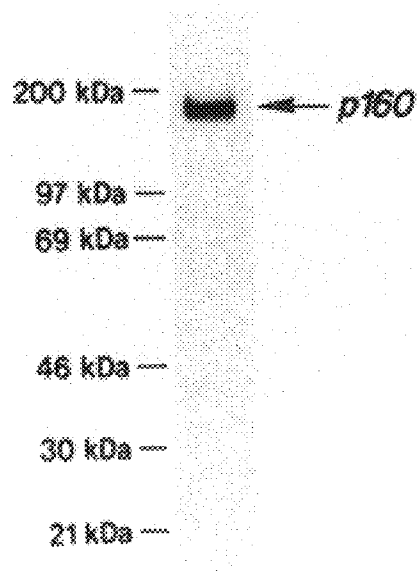
FIG. 15 is an electrophoretic photograph showing autophosphorylation of p160.

Protein Kinase Activity Analysis (1) Autophosphorylation of p160 and phosphoamino acid analysis The Mono Q fraction of p160 (8 ng of protein) was incubated with 4 μM $[\gamma\text{-}^{32}P]$ATP (Dupont-New England Nuclear; 25 Ci/mmol) at 30° C. for 30 min in 50 mM HEPES-NaOH, pH 7.3, 50 mM NaCl, 10 mM $MgCl_2$, 5 mM $MnCl_2$, 0.03% Briji 35 and 2 mM dithiothreitol. After the incubation, the solution was mixed with an equal volume of 2×Laemmli sample buffer, boiled for 5 min and then applied to SDS-PAGE. The gel was stained with Commassie Blue, dried and subjected to autoradiography. The result is shown in FIG. 15.

Figure 16:
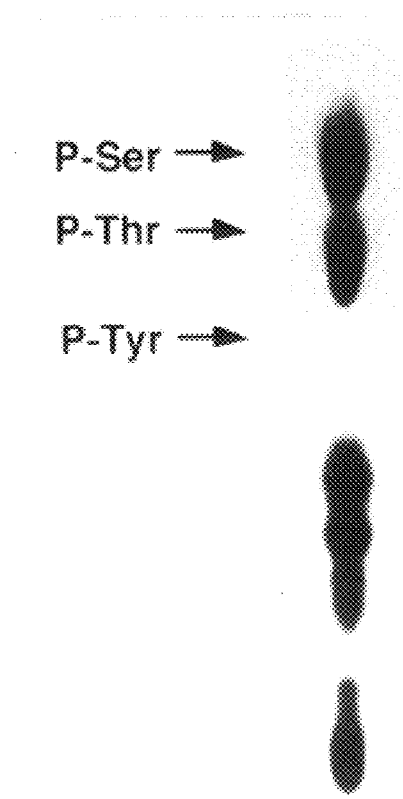
FIG. 16 is an electrophoretic photograph showing a result of phosphoamino acid analysis. P-Ser, P-Thr and P-Tyr indicate the positions of phosphoserine, phosphothreonine, and phosphotyrosine, respectively.

For the phosphoamino acid analysis, the radiolabeled protein was transferred to a PVDF membrane. The radioactive band was then excised and subjected to phosphoamino acid analysis as previously described (Kumagai, N. et al., FEBS Lett., 366, 11–16 (1995)). The result is shown in FIG. 16.

(2) Phosphorylation reactions

Figure 17:
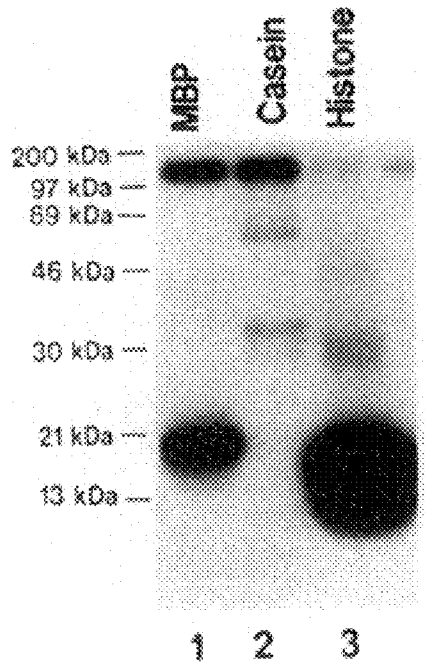
FIG. 17 is an electrophoretic photograph showing phosphorylation of MBP and histone by p160.

The Mono Q fraction of p160 (17.5 ng of protein) was incubated with 40 $\mu$M [$\gamma$-$^{32}$P]ATP (3.3 Ci/mmol) and with 3 $\mu$g of either histone (HF2A, Worthington), dephosphorylated casein (Sigma) or MBP (Gibco) in the presence of 0.4 $\mu$M GDP- or GTP$\gamma$S-loaded GST-RhoA (see example 1) at 30° C. in a total volume of 31 $\mu$l. A 7 $\mu$l aliquot was taken at 0, 5, 10 and 20 min, mixed with an equal volume of 2×Laemmli sample buffer, and applied to SDS-PAGE. The gel was stained with Commassie Blue, dried and subjected to autoradiography. The result obtained after 20 min is shown in FIG. 17.

Figure 18:
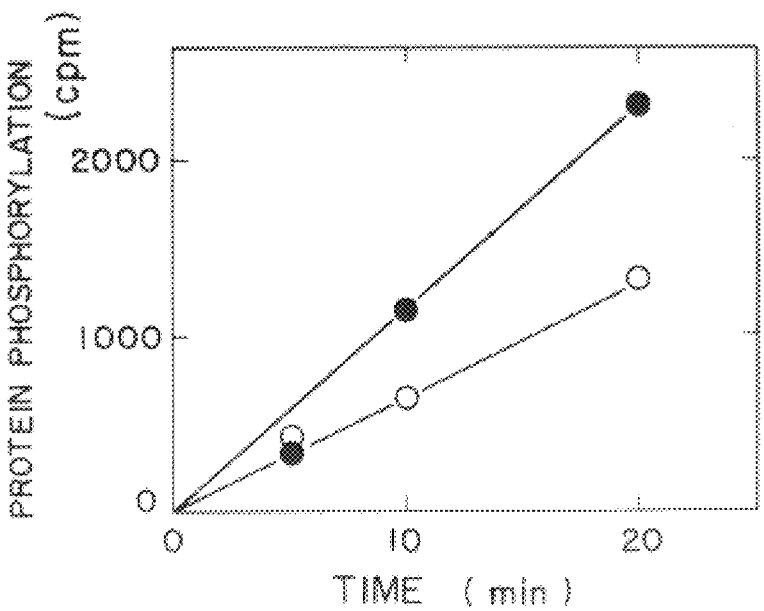
FIG. 18 quantitatively shows activation of the histone phosphorylating activity of p160 by GTPγS-binding Rho protein. A solid circle indicates GTPγS-binding GST-Rho protein, and a blank circle indicates GDP-binding GST-Rho protein.

Then, the radioactive band of histone was excised for determination of radioactivity by Cherenkov's method. The result is shown in FIG. 18. Phosphorylation of histone in the presence of GTP-binding Rho was apparently enhanced more than that in the presence of GDP-binding Rho.

Example 3

Amino Acid Sequence of p160 and Its Encoding DNA Sequence (1) Peptide sequencing The Mono Q fraction containing 30 pmol of p160 was subjected to SDS-PAGE and then transferred to a PVDF membrane. The proteins were stained with Ponceau S, and the p160 band was excised. The immobilized p160 was digested with Achromobacter lysyl endopeptidase or endoproteinase Asp-N, and the peptides released were separated and sequenced as previously described (Iwamatsu, A., Electrophoresis, 13, 142–147 (1992); Maekawa, M. et al., Mol. Cell. Biol., 14, 6879–6885 (1994)).

(2) cDNA cloning

Poly(A)+ RNA was prepared from cultured MEG-01S human megakaryocytic leukemia cells MEG-01 (Hirata, M. et al., Nature, 349, 617–620 (1991); Ogura, M. et al., Blood, 66, 1384–1392 (1985)) and the λgt-10 and λZAP-II cDNA libraries were constructed as previously described (Kakizuka, A. et al., A Practical Approach (Oxford: IRL Press) pp. 223–232). The λgt-10 library was first screened with a 20 mer degenerate oligonucleotide probe corresponding to the 7 mer partial amino acid sequence AP-23. One positive clone containing 2.6 kbp insert (clone P2) was isolated from $3\times10^5$ plaques. This clone contained a nucleotide sequence corresponding to the probe and encoded two other peptide sequences derived from p160 in-frame.

Figure 19:
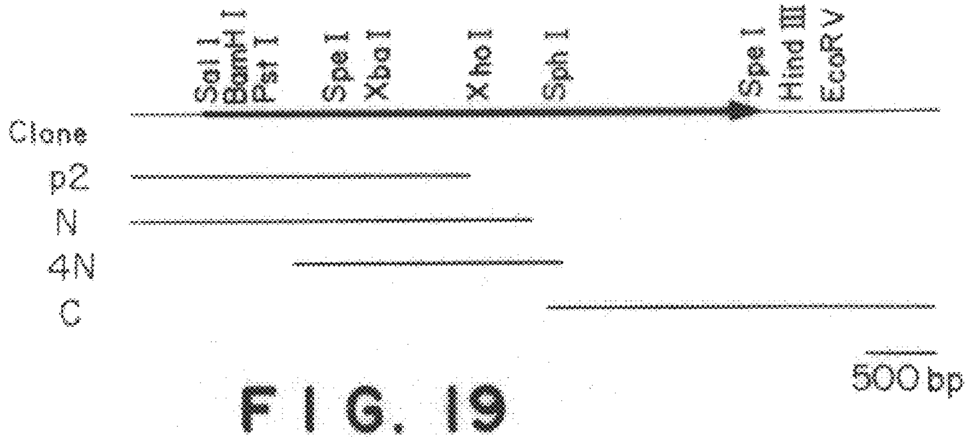
FIG. 19 is a schematic representation of the isolated p160 clones. A thick arrow indicates the open reading frame.

Using the 450 bp 5'-part of this cDNA as a probe, the λZAP-II cDNA library was then screened, and one clone, clone N, was isolated. This clone contained a cDNA which overlapped P2 and extended 450 bp into the 3'-end. Using this 3'-extended part as a probe, clone 4N was obtained from the λgt-10 library, which had a 3'-extension of 350 bp. Clone C was then isolated using this 3'-extension as a probe from the same library, and extended the 3'-end by another 2.5 kbp. The relative positions of the clones are shown in FIG. 19.

(3) Sequencing

Nucleotide sequence was determined on both strands using the dideoxy chain termination method. The predicted amino acid sequence and DNA sequence are shown in FIGS. 1–10.

Figure 21:
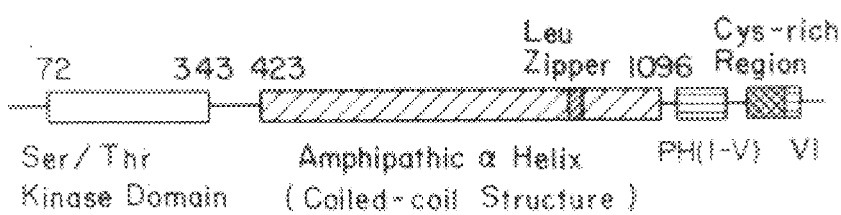
FIG. 21 is schematic representation of the structure of p160.

Sequence comparisons were made using BLAST (Altschul, S. F. et al., J. Mol. Biol., 215, 403–410 (1990)) against a non-redundant PDP+SwissProt+Spupdate+PIR+GenPept+GPupdate database. The coiled-coil structure probability was analyzed by the algorithm developed by Lupas et al. (Lupas, A. et al., Science, 252, 1162–1164 (1991)). As a result, the structure of p160 was predicted as shown in FIG. 21.

It was demonstrated that p160 contained a sequence peculiar to proteins in the protein kinase A family (S. K. Hanks et al., Science, 241, 42–52 (1988)), one of the serine/threonine kinase families, which consisted of the 272 amino acids at the N-terminal (corresponding to the amino acid sequence 72-343 in FIG. 1). A sequence of 420 amino acids at the N-terminal (corresponding to the amino acid sequence 1-420 in FIG. 1) containing the kinase region had 44% identity to the amino acid sequence of myotonic dystrophy kinase (MD-PK) (J. D. Brook et al., Cell, 68, 799–808 (1992); M. S. Mahadevan et al., Hum. Mol. Genet., 2, 299–344 (1993)), as shown in FIG. 25. Also, a sequence of 600 amino acid following the kinase region (corresponding to the amino acid sequence 423-1096 in FIG. 1) contained partial sequences that had homology to various coiled-coil proteins, including myosin heavy chain, as shown in FIG. 26. The C-terminal of p160 had a sequence similar to a pleckstrin-homology (PH) domain (A. Musaccio et al., Trends Biochem. Sci., 18, 343–348 (1993)) as shown in FIG. 27, and a sequence similar to a cysteine-rich zinc finger domain as found in protein kinase C (A. F. Questetal, J. Biol. Chem., 269, 2961–70 (1994); J. Zhang et al., J. Biol. Chem., 269, 18727–18730 (1994)) as shown in FIG. 28. Also, as shown in FIG. 1, p160 had a leucine zipper-like sequence.

(4) Northern blot analysis

Figure 22:
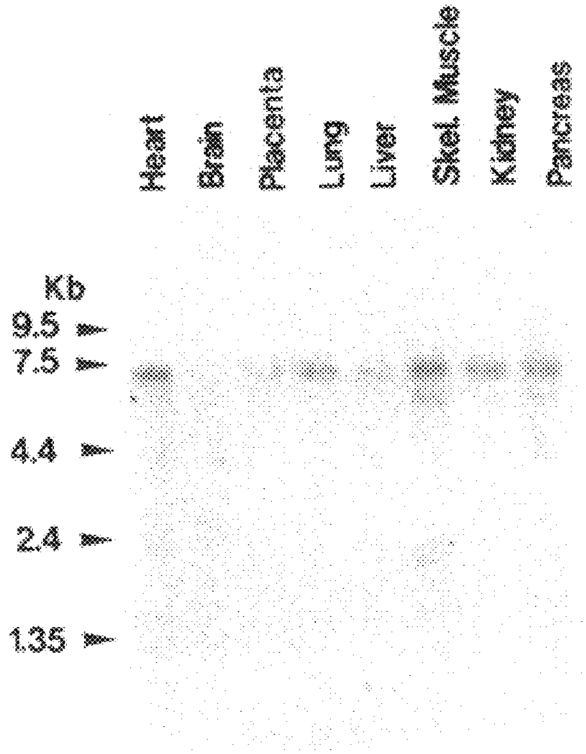
FIG. 22 is an electrophoretic photograph showing the Northern blot analysis of p160 expression in various human tissues.

Northern blot analysis was performed on Human Multiple Tissue Blots I (CLONTECH) with a $^{32}$P-labeled 5'-fragment of NotI/BamHI digests of P2 as a probe. Hybridization was carried out in 5×SSPE containing 50 mM sodium phosphate, pH 6.5, 50% formamide, 5×Denhardt's, 0.1% SDS and 0.2 mg/ml yeast tRNA at 42° C. for 16 h. The filter was washed three times in 2×SSC-0.1% SDS at 42° C. for 15 min, and then exposed to an X-ray film for 4 days. The result is shown in FIG. 22

Example 4

Construction of Expression and Transfection Vectors

The full size cDNA used for expression was constructed as follows. A plasmid DNA pBluescript SK$^+$ (Stratagene) carrying the clone 4N cDNA was digested with SphI and SacI, and then ligated with a SphI-SpeI fragment of clone C and a SpeI-SmaI-EcoRV-SacI linker to produce plasmid 4N-C. PCR was then performed with clone N cDNA as a template with the forward primer, 5'-GGGGAGCTCAAGGTACCTCGAGTGGGGACAGTTTTGAG-3' (SEQ ID NO:3) and with the reverse primer 5'-CGCCTGCAGGCTTTCATTCGTAAATCTCTG-3' (SEQ ID NO:9). The PCR fragment was subcloned into pBluescript SK$^+$ (Stratagene) and sequenced. The plasmid carrying this product was digested with BamHI and EcoRV, and then ligated with an XbaI-EcoRV fragment from plasmid 4N-C and a BamHI-XbaI fragment from clone N. An Asp718-EcoRV fragment was excised from the resultant plasmid and then inserted into a pCMX vector carrying a myc epitope sequence (Dyck, J. A. et al., Cell, 76, 333–343) (pCMX-myc-p160).

Figure 20:
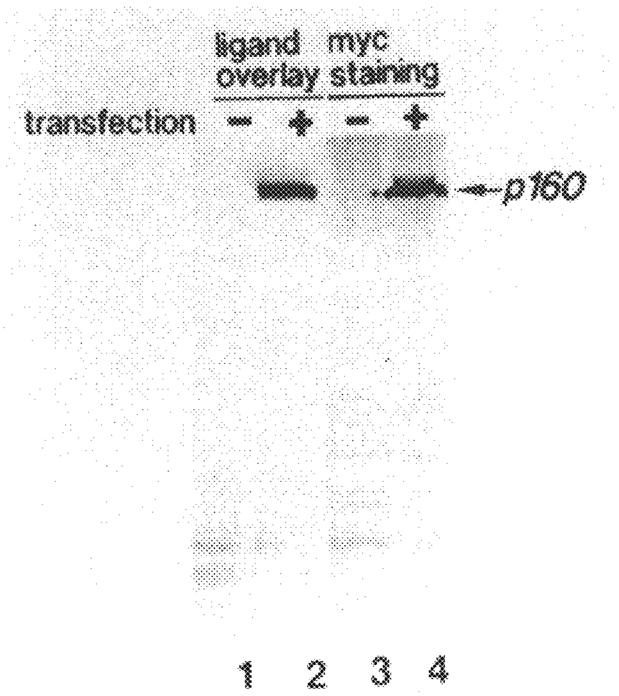
FIG. 20 is an electrophoretic photograph showing Rho binding to the expressed proteins. Lanes 1 and 3: mock-transfected cells. Lanes 2 and 4: transfected cells.

COS-7 cells (ATCC CRL 1651) were plated at $10^5$ cells per 3.5 cm dish and cultured overnight, and then transfected with 1.5 $\mu$g of the pCMX vector with lipofectamine. The cells were incubated in Opti-MEM for 6 h, and then cultured in DMEM containing 10% fetal calf serum for 18 h. The medium was removed and the cells were washed twice with PBS, and lysed in 100 μl of 2×Laemmli sample buffer. Thirty μl aliquots of the lysates were subjected to SDS-PAGE, and the separated proteins were transferred to a PVDF membrane or a nitrocellulose membrane. Immunoblotting using a 9E10 anti-myc epitope antibody and the ligand overlay analysis were carried out as described. The result is shown in FIG. 20.

Example 5

Cotransfection of p160 cDNA with $RhoA^{Va114}$ and Wild Type RhoA cDNA

COS-7 cells were plated at a density of $1.2\times10^5$ cells per 6 cm dish. After culturing for 1 day, the medium was removed, and the cells were transfected with 2.25 μg of pCMX-myc-p160 or pCMX-myc, together with 0.75 μg of either pEF-BOS-HA (Hemophilus influenza hemagglutinin)-tagged-$Val^{14}$-RhoA, pEF-BOS-HA-RhoA or vector alone, using lipofectamine in 2 ml of Opti-MEM. At 6 h, 3 ml of Opti-MEM was added and the cells were cultured for another 30 h. The cells were washed once with ice-cold PBS and lysed with a lysis buffer (20 mM Tris-HCl, pH 7.5, 1 mM EDTA, 1 mM EGTA, 5 mM $MgCl_2$, 25 mM NaF, 10 mM β-glycerophosphate, 5 mM sodium pyrophosphate, 0.2 mM PMSF, 2 mM dithiothreitol, 0.2 mM sodium vanadate, 0.05% Triton X-100 and 0.1 μM calyculin A) on ice for 20 min. The lysates were centrifuged at 10,000×g for 10 min, and the supernatant was collected.

Figure 23:
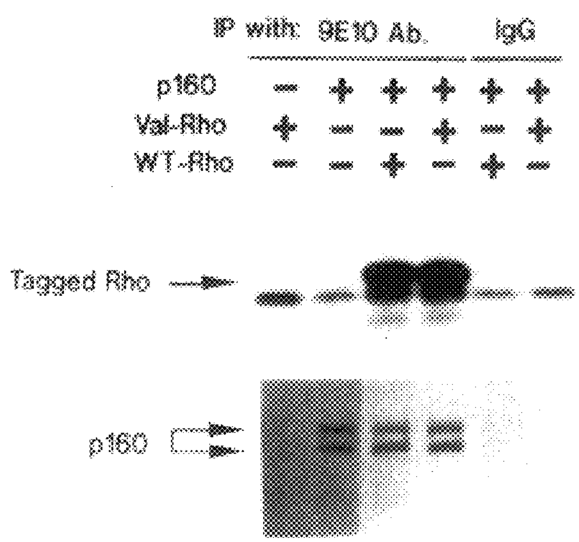
FIG. 23 is an electrophoretic photograph showing coprecipitation of p160 and the Rho protein from COS cells. Upper panel: ADP-ribosylation. Lower panel: immunoblotting with an anti-myc antibody. A single arrow indicates the HA-tagged Rho, and double arrows indicate myc-tagged p160.

Either a 9E10 antibody or control IgG coupled to protein G-Sepharose was then added to the supernatant, and the mixture was shaken at 4° C. for 3 h. The suspension was centrifuged at 1000×g for 5 min, and the resultant pellets were washed three times with 0.5 ml of the lysis buffer. For the ADP-ribosylation reaction, the pellets were resuspended in 500 μl of the ADP-ribosylation buffer without dithiothreitol (Morii, N. et al., J. Biol. Chem., 263 12420–12426 (1988)). One hundred μl aliquots were then taken and used for immunoblotting with anti-myc antibody after precipitation. The result is shown in the lower panel of FIG. 23.

The remaining 400 μl of suspension was centrifuged, and the pellet was resuspended in 34 μl of ADP-ribosylation buffer. [$^{32}$P]NAD (Dupont-New England Nuclear; $10^6$ c.p.m./pmol) was added to a concentration of 1 μM, and the reaction was allowed to proceed with 400 ng of botulinum C3 exoenzyme at 30° C. for 12 h. The analysis of the ADP-ribosylation reaction was performed as previously described (Morii, N. et al., J. Biol. Chem., 263, 12420–12426 (1988)). The result is shown in the upper panel of FIG. 23.

Figure 24:
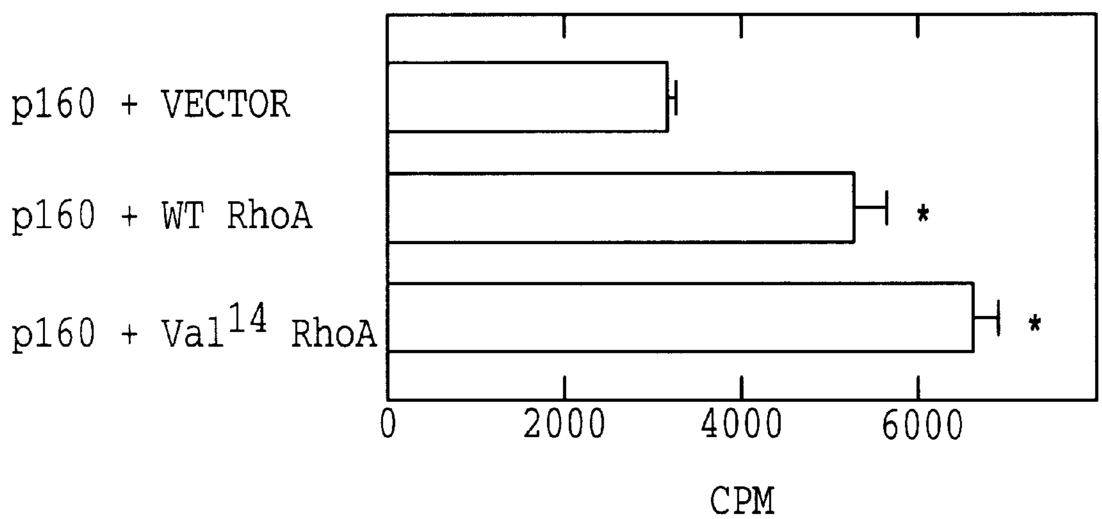
FIG. 24 shows the activation of p160 kinase activity in vivo.

For the kinase assay, the pellets were washed once with 20 mM Tris-HCl, pH 7.5, containing 5 mM $MgCl_2$ and 0.1 μM calyculin A, and were then resuspended to the phosphorylation buffer. The phosphorylation reaction was carried out as described above with histone as the substrate. The result is shown in FIG. 24.

Example 6

Identification of Rho-Binding Region in p160

Figure 29:
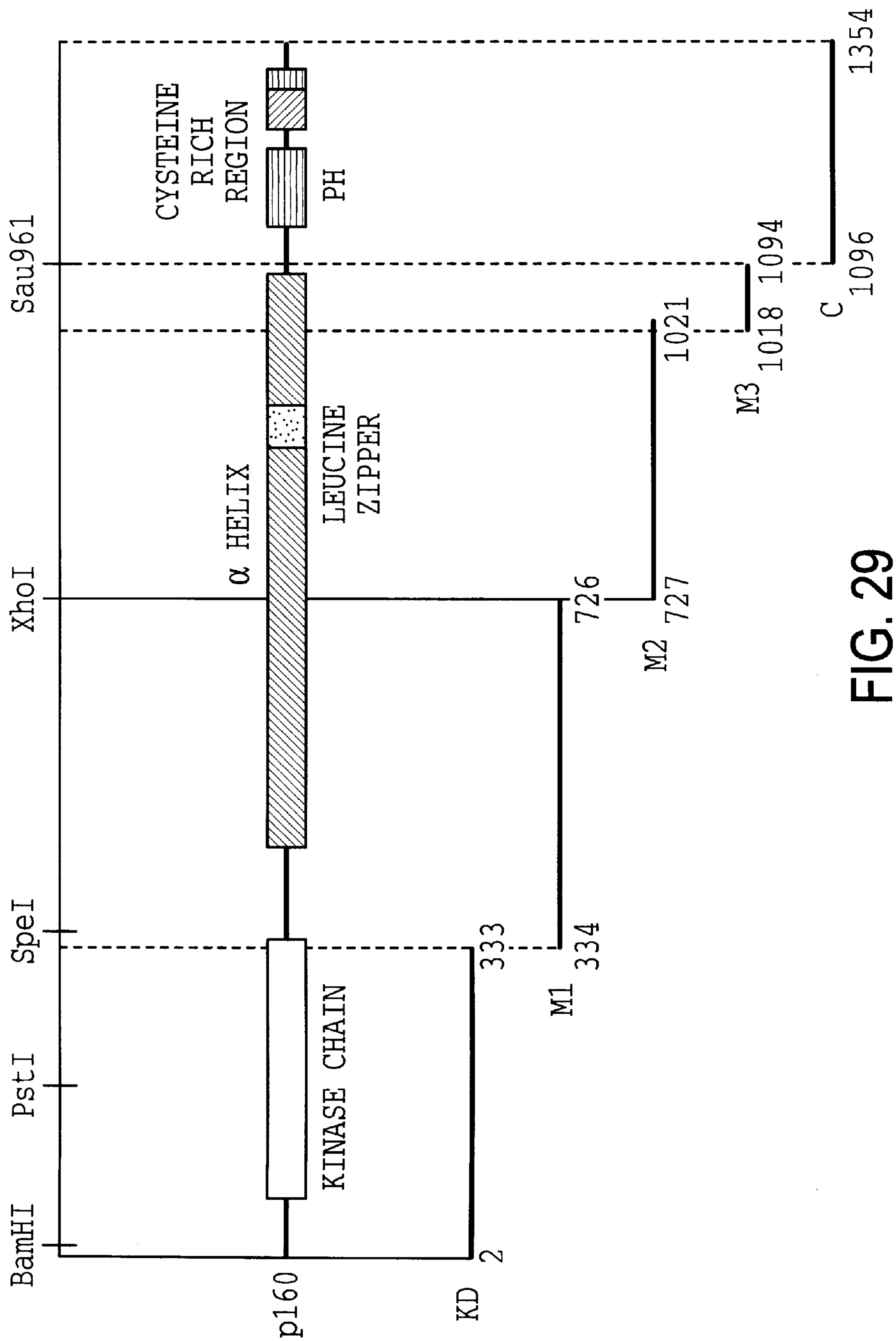
FIG. 29 is a schematic representation of truncation mutants of p160. Five mutants (KD, M1, M2, M3 and C) are indicated by thick lines. Numbers below each line indicate amino acid residues at the amino and carboxyl terminals of each fragment. The functional and structural regions of p160 are also schematically shown in the middle. The upper line indicates the positions of restriction enzyme sites in p160 cDNA used in construction of these mutants.

As described in example 1, 2, 4 and 5, GTP-binding RhoA binds specifically to p160 and activates it. In order to identify the Rho-binding domain of p160, p160 was divided into five fragments as shown in FIG. 29, which were expressed as His-tagged proteins and purified by using Ni-NTA resin. The detailed procedure is as follows:

p160 was divided into 5 fragments, KD (2-333), M1 (334-726), M2 (727-1021), M3 (1018-1094) and C (1096-1354) as shown in FIG. 29, and each expressed as a $His_6$-tagged bacterial protein. To introduce these fragments into *E. coli*, the cloning region (GGG ATC CGT CGA CCT GCA GCC AAG CTT (SEQ ID NO:67)) of plasmid vector pQE-11 (Quiagen) was replaced by GGG ATC CCC GGG TAC CGA GCT CAA TTG CGG CCG CTA GAT AGA TAG AAG CGA GCT CGA ATT (SEQ ID NO:68) and restriction sites for BamHI, SmaI, Asp718, SacI, and NotI were created.

To insert the KD fragment (2-333) in-frame at SacI site of pQE-11 which had been modified as described above (hereinafter referred to as "modified pQE-11"), a cDNA fragment corresponding to the amino acid sequence 2-73 in SEQ ID NO: 2 was amplified by PCR using synthetic primers of 5'-GG GGA GCT CAA GGT ACC TCG ACT GGG GAC AGT TTT GAG-3' (SEQ ID NO:5) and 5'-CG CCT GCA GGC TTT CAT TCG TAA ATC TCT G-3' (SEQ ID NO:6). The DNA templates for all of PCRs described here were derived from pCMX-myc-p160 (see example 4). PCR was performed by incubation first at 95° C. for 1 min followed by 15 cycles of [1 min at 95° C., 1 min at 53° C., 1 min at 72° C.] followed by 72° C. for 2 min. This fragment was digested with SacI and PstI and ligated into the SacI and PstI sites of $pSK^+$ (Stratagene).

This plasmid was digested with BamHI and PstI and the BamHI-PstI fragment of original p160 clone N cDNA (see example 3) was inserted at these sites ($pSK^+$-NT1). Fragment NT2 which corresponds to the amino acid sequence 74-333 in SEQ ID NO: 2 was also made by PCR using the synthetic oligonucleotide primers 5'-GGG ATC CCC GGT ACC GAA GAT TAT GAA GTA GTG AAG G-3' (SEQ ID NO:7) and 5'-TC AGC TAA TTA GAG CTC TTT GAT TTC TTC TAC ACC ATT TC-3' (SEQ ID NO:8). PCR was done by incubating first at 95° C. for 1 min followed by 15 cycles of [1 min at 95° C., 1 min at 55° C., 1 min at 72° C.] and finally at 72° C. for 2 min. The product was then blunted and ligated into the EcoRV site of $pSK^+$ (Stratagene) ($pSK^+$-NT2). To combine NT1 and NT2, the PstI-PstI fragment of $pSK^+$-NT2 was ligated into the PstI site of $pSK^+$-NT1, resulting in an insert spanning the amino acid sequence 2-333 in SEQ ID NO: 1 ($pSK^+$-KD). The SacI-NotI fragment of $pSK^+$-KD was ligated into modified pQE-11 to generate a plasmid expressing His (×6) -KD.

To make the M1 fragment, a cDNA fragment corresponding to the amino acid sequence 334-395 in SEQ ID NO: 2 was first amplified by PCR using primers of 5'-GG GGA GCT CGA CAT CTC TTC TTC AAA AAT G-3' (SEQ ID NO:9) and 5'-CC TAC AAA AGG TAG TTG A-3' (SEQ ID NO:10) (incubation at 95° C. for 1 min, followed by 15 cycles of 1 min at 95° C., 1 min at 53° C. and 1 min at 72° C., and finally at 72° C. for 2 min). The product was blunted and digested with SacI. pSK+ (Stratagene) was digested with Asp718, and a 14-mer oligonucleotide was inserted to create NotI site. The PCR product was then ligated into the SacI and EcoRV sites of the modified $pSK^+$. This plasmid was then digested with SpeI and XhoI and the SpeI-XhoI fragment of original p160 clone 4N cDNA (see embodiment 3 (2)) was inserted at these sites ($pSK^+$-M1). The SacI-NotI fragment of $pSK^+$-M1 (334-726) was then ligated into modified pQE-11.

The M2 fragment (727-1021) was prepared by digesting $pSK^+$ (Stratagene) carrying the original clone 4N cDNA encoding the amino acid sequence 273-1021 in SEQ ID NO: 2 (see example 3 (2)) with XhoI to delete N-terminal and self-ligate. This plasmid was digested with Asp718 and SacI and ligated into the Asp718 and SacI sites of modified pQE-11.

The M3 fragment (1018-1094) was generated by PCR using primers of 5'-C GGG ATC CCC GAT AGA AAG AAA GCT AAT ACA CA-3' (SEQ ID NO:11) and 5'-TAA CCC GGG AAG TTT AGC ACG CAA TTG CTC-3' (SEQ ID NO:12) at 95° C. for 3 min, followed by 15 cycles of 1 min at 95° C., 1 min at 59° C. and 1 min at 72° C. and finally at 72° C. for 2 min. The product was blunted and digested with BamHI and inserted into the BamHI and EcoRV sites of $pSK^+$ (Stratagene) ($pSK^+$-M3). The BamHI-Asp718 fragment of $pSK^+$-M3 (1018-1094) was ligated into modified pQE-11.

To generate the plasmid expressing $His_6$-C (1096-1354), the Sau96I-HincII fragment of the original p160 clone C cDNA (see example 3 (2)) was blunted and ligated into the SmaI site of modified pQE-11.

*E. coli* was transformed with pQE plasmids described above and grown. Isopropylβ-D-thiogalactoside was added to the culture at $A_{600}$ of 0.8 and the culture was continued for another 20 h at 30° C. Cells were lysed with 8 M urea containing 0.1 M sodium phosphate and 10 mM Tris-HCl, pH 8.0. Following 1 h incubation at 25° C., the lysates were centrifuged for 10 min at 12,000×g. The supernatants were incubated at 25° C. for 1 h with Ni-NTA resin (Qiagen). The resin was washed with 8 M urea, 0.1 M sodium phosphate, and 0.01 M Tris-HCl, pH 6.3, and boiled in Laemmli sample buffer for 5 min. The recombinant human RhoA protein was expressed as glutathione-S-transferase fusion protein and purified as previously described (Morii, N. et al, J. Biol. Chem., 268, 27160–27163 (1993)).

Figure 32:
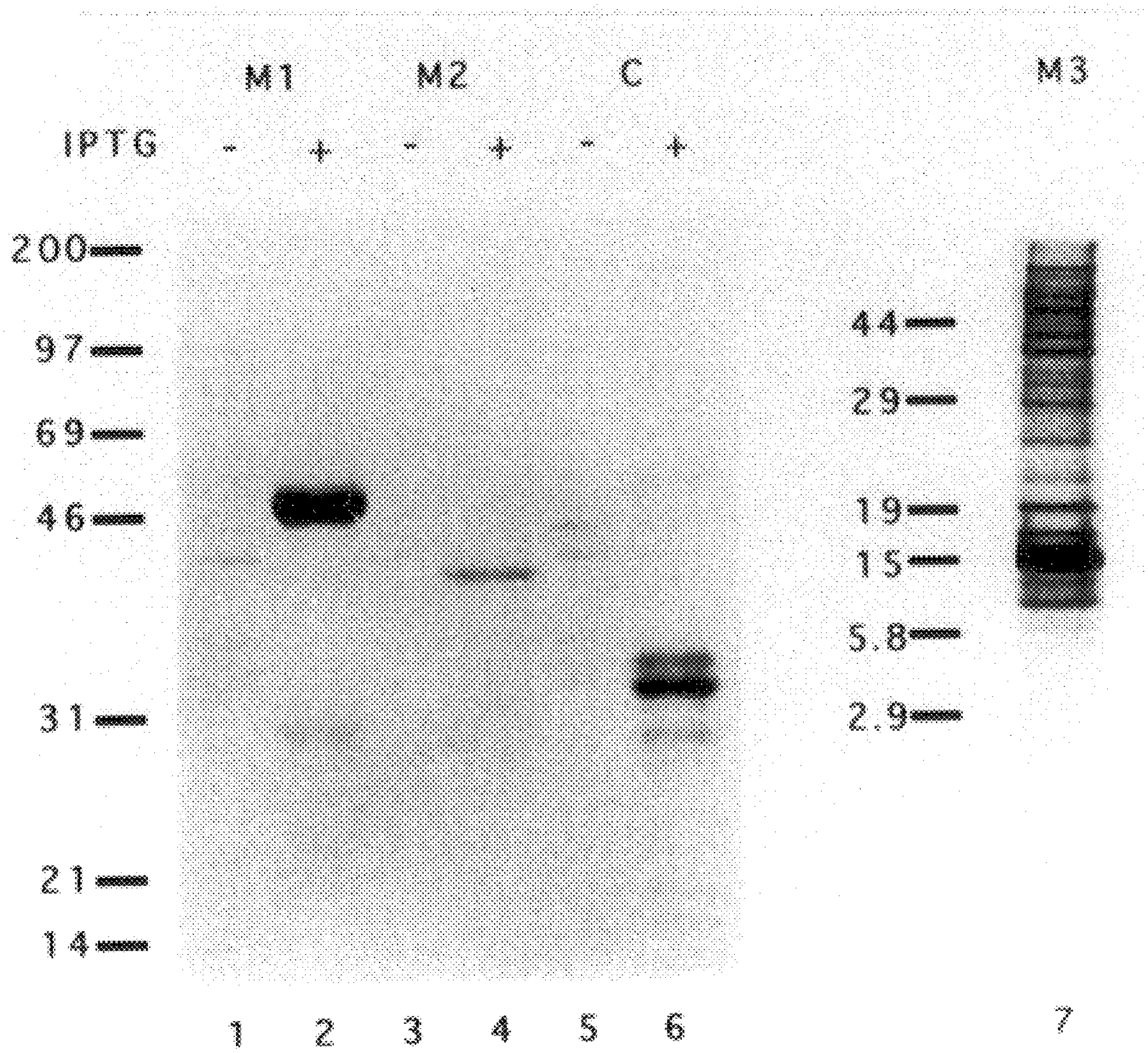
FIG. 32 is an electrophoretic photograph showing a result of purification of truncation mutants of p160. The truncation mutants M1, M2, M3 and C were expressed with (lanes 2, 4, 6 and 7) or without (lanes 1, 3 and 5) IPTG. The purified proteins were subjected to 10% (for M1, M2 and C) or 15% (for M3) SDS-PAGE. Positions of molecular weight marker proteins are shown on the left in kilodaltons.

The purity of the preparation used in the assay was analyzed by SDS-PAGE. As shown in FIG. 32, each protein preparation exhibited a single band at the expected size, showing an increase in protein by IPTG induction. The KD fragment was not expressed, probably because the KD protein functioned as a structurally active mutant.

Then, the expressed proteins were analyzed by the ligand overlay assay, with $[^{35}S]$GTPγS-loaded GST-RhoA used as a probe.

His-tagged proteins extracted in Laemmli buffer were applied to 8, 10 or 15% SDS-PAGE and separated proteins were transferred to a nitrocellulose membrane (Schleicher & Schuell). Proteins on the membrane were denatured and renatured as described previously (see example 1; Manser, E. et al., J. Biol. Chem., 267, 16025–16028 (1992)). The renatured membrane was then incubated with 10 or 20 nM $[^{35}S]$GTPγS-loaded each Rho protein in an overlay buffer as described (see example 1; Manser, E. et al., J. Biol. Chem., 267, 16025–16028 (1992)). The membrane was washed, dried and exposed to an X-ray film.

Figure 33:
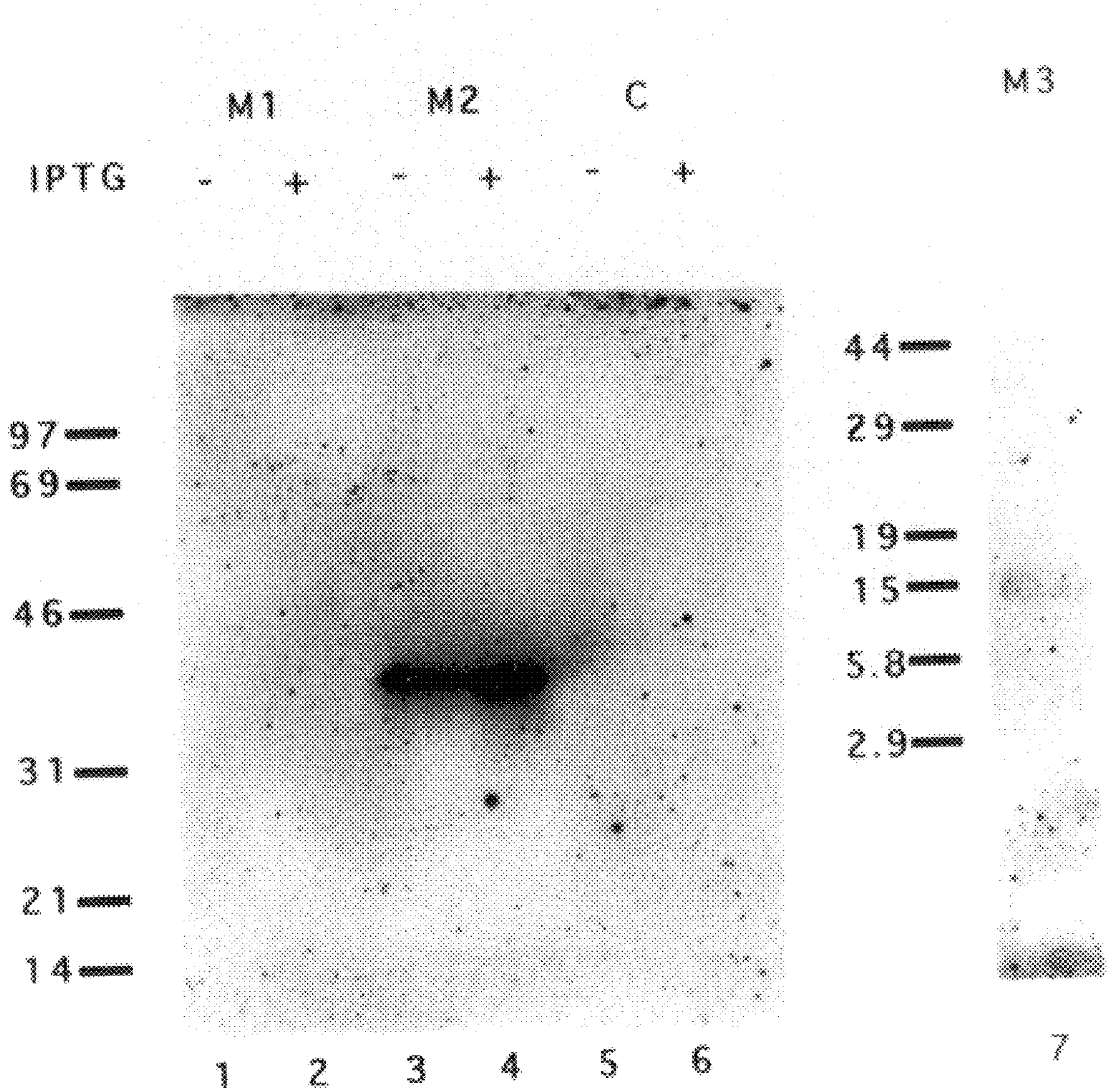
FIG. 33 is an electrophoretic photograph showing a result of ligand overlay assay for the truncation mutants of p160. The mutants M1, M2, M3 and C were expressed with (lanes 2, 4, 6 and 7) or without (lanes 1, 3 and 5) IPTG. The purified proteins were subjected to 10% (for M1, M2 and C) or 15% (for M3) SDS-PAGE. An amount of the proteins is 1/10 of that in FIG. 32. Positions of molecular weight marker proteins are shown on the left in kilodaltons.

The result is shown in FIG. 33. Radioactive bands were observed on the filter at the same positions as the M2 fragment stained with amido black in lanes 3 and 4 only. These results indicated that the M2 fragment (727-1021) contained GTP-RhoA-binding domain.

Example 7

Identification of Rho-Binding Region in M2 Fragment

Figure 30:
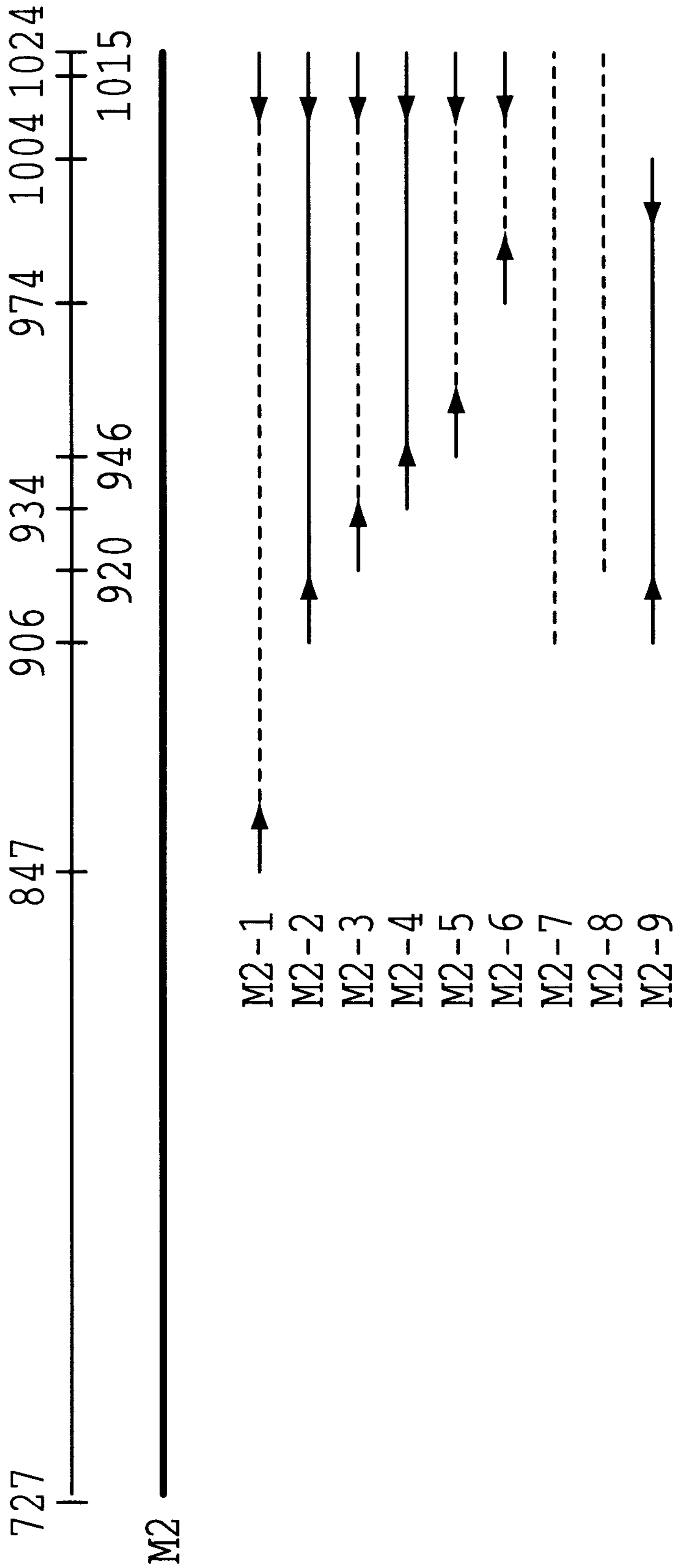
FIG. 30 shows truncation mutants of M2 fragment. Lengths of nine mutants (M2-1 to M2-9) and parts of M2 covered by each mutant are shown. Numbers in the upper line indicate the amino and carboxyl terminal residues of M2 and the truncation mutants, as the amino acid number of p160. Arrows indicate the primer positions used in PCR amplification of the respective mutant except M2-7 and M2-8. Mutants M2-7 and M2-8 were excised from the original p160 cDNA. Primer sequences used are shown in Table 1.
Figure 34:
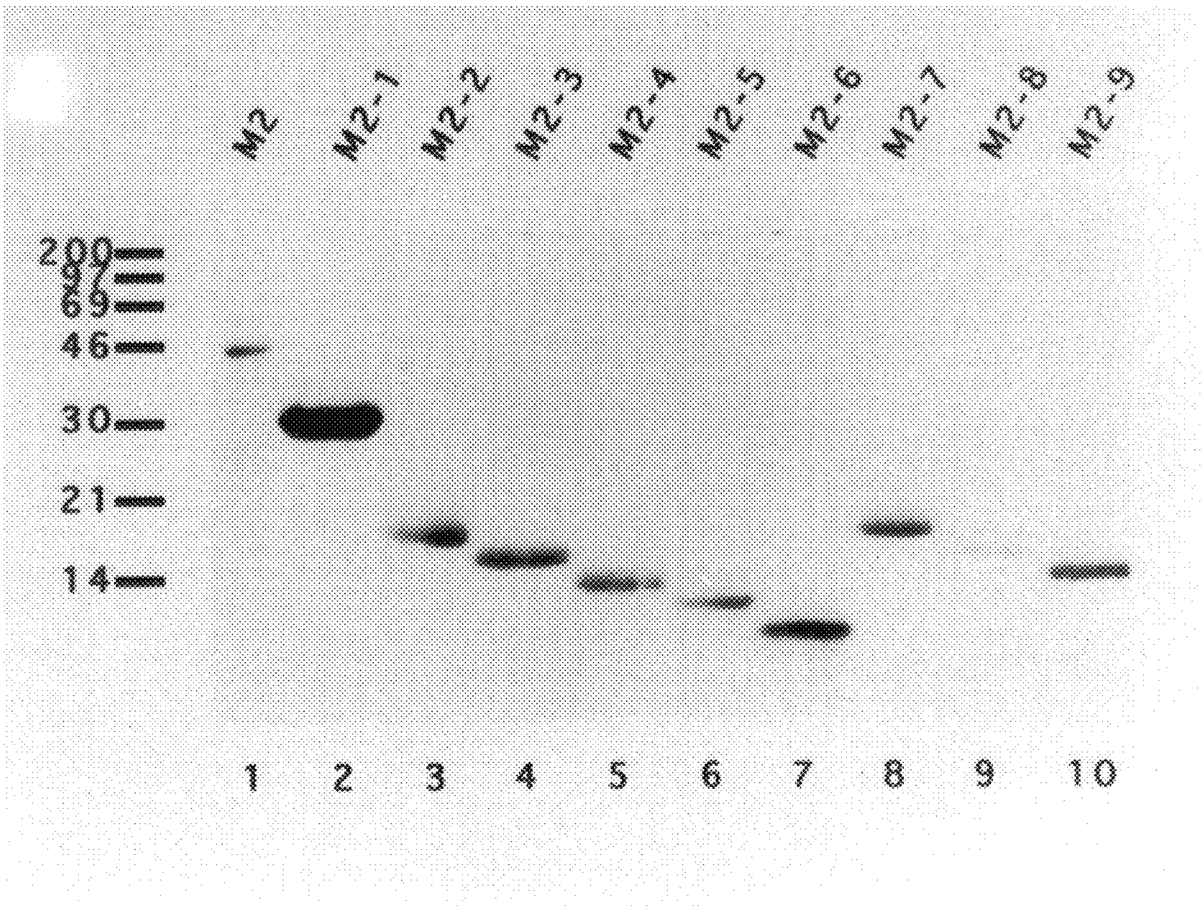
FIG. 34 is an electrophoretic photograph showing a result of purification of the truncation mutant M2. Positions of molecular weight marker proteins are shown on the left in kilodaltons.

In order to identify the region on the M2 fragment critical to RhoA-binding activity, the N-terminal of the M2 fragment was deleted (M2-1 to M2-6 in FIG. 30). The resulting truncation mutants were expressed as His-tagged proteins, which were then purified (FIG. 34, lanes 1–7). The detailed procedure is as follows.

A variety of truncation mutants of the M2 fragment were made using PCR, and each expressed as a His-tagged bacterial protein as shown in FIG. 30. The fragments M2-1 (847-1024), M2-2 (906-1024), M2-3 (920-1024), M2-4 (934-1024), M2-5 (946-1024), and M2-6 (974-1024) were amplified using primer pairs as shown in Table 1. For M2-1 and M2-2, PCR was done at 95° C. for 3 min followed by 15 cycles of [1 min at 95° C., 1 min at 59° C., 2 min at 72° C.] followed by 72° C. for 2 min. For M2-3, M2-4, M2-5 and M2-6, PCR was done at 95° C. for 3 min followed by 15 cycles of [1 min at 95° C., 1 min at 55° C., 1 min at 72° C.] followed by 72° C. for 2 min. The DNA templates for all of PCRs described here were pCMX-myc-p160 (see example 4).

The products were then blunted, digested with BamHI and inserted into the BamHI and EroRV sites of $pSK^-$ (Stratagene). BamHI-Asp718 fragments of each plasmid were ligated into the BamHI and Asp718 sites of modified pQE-11, and expressed. To generate the plasmids expressing $His_6$-M2-7 (906-1015) and -M2-8 (920-1015), the BamHI-DraI fragments of $pSK^-$-M2-2 (906-1024) and -M2-3 (920-1024) were ligated into the BamHI site and blunted NotI site of modified pQE-11, respectively. M2-9 (906-1004) cDNA was amplified by PCR using No. 7 primer pair (Table 1).

TABLE 1

Primers used in PCR for amplification of truncation mutants of M2.

| No. | Fragment | A.A.[a] | SEQ ID NO: | Sequence of 5' primer[b] |
|---|---|---|---|---|
| 1 | M2-1 | 847-1024 | 13 | CC GGG ATC CCC GAA GCT GAG CAA TAT TTC TCG |
| 2 | M2-2 | 906-1024 | 15 | C GGG ATC CCC GGG TAC CGA GGC CTT CTG GAA GAA C |
| 3 | M2-3 | 920-1024 | 16 | C GGG ATC CCC AAG AAA GCT GCT TCA AGA AAT AG |
| 4 | M2-4 | 934-1024 | 17 | C GGG ATC CCC AAA GAT CGC ACT GTT AGT CGG |
| 5 | M2-5 | 946-1024 | 18 | G GGG ATC CCC AGC ATG CTA ACC AAA GAT ATT G |
| 6 | M2-6 | 974-1024 | 19 | G GGG ATC CCC AAA CTG GAG AAG GAG GAG G |
| 7 | M2-9 | 906-1015 | 20 | C GGG ATC CCC GGG TAC CGA GGC CTT CTG GAA GAA C |
| **No.** | **Fragment** | **A.A.[a]** | **SEQ ID NO:** | **Sequence of 3' primer[b]** |
| 1 | M2-1 | 847-1024 | 14 | TA ACC CGG GTG TGT ATT AGC TTT CTT TCT ATC |

TABLE 1-continued

Primers used in PCR for amplification of truncation mutants of M2.

| | | | | |
|---|---|---|---|---|
| 2 | M2-2 | 906-1024 | 14 | TA ACC CGG GTG TGT ATT AGC TTT CTT TCT ATC |
| 3 | M2-3 | 920-1024 | 14 | TA ACC CGG GTG TGT ATT AGC TTT CTT TCT ATC |
| 4 | M2-4 | 934-1024 | 14 | TA ACC CGG GTG TGT ATT AGC TTT CTT TCT ATC |
| 5 | M2-5 | 946-1024 | 14 | TA ACC CGG GTG TGT ATT AGC TTT CTT TCT ATC |
| 6 | M2-6 | 974-1024 | 14 | TA ACC CGG GTG TGT ATT AGC TTT CTT TCT ATC |
| 7 | M2-9 | 906-1015 | 21 | GC GAA TTC GCG GCC GCT GTT AAC AGC CTG TGT TTT AAG |

[a]A region of p160 covered by each fragment peptide is shown by the amino- and carboxyl terminal amino acid numbers.
[b]All the sequences shown are from 5' to 3' direction. Nucleotides corresponding to p160 sequence are underlined.

PCR was done using 95° C. for 3 min followed by 15 cycles of [1 min at 95° C., 1 min at 59° C., 2 min at 72° C.] followed by 72° C. for 2 min. The product was digested with BamHI and NotI and ligated into the BamHI and NotI sites of modified pQE-11.

The expression, purification, and ligand overlay assay of the M2 fragments fused with *E. coli* His were performed as described in example 6.

Figure 35:
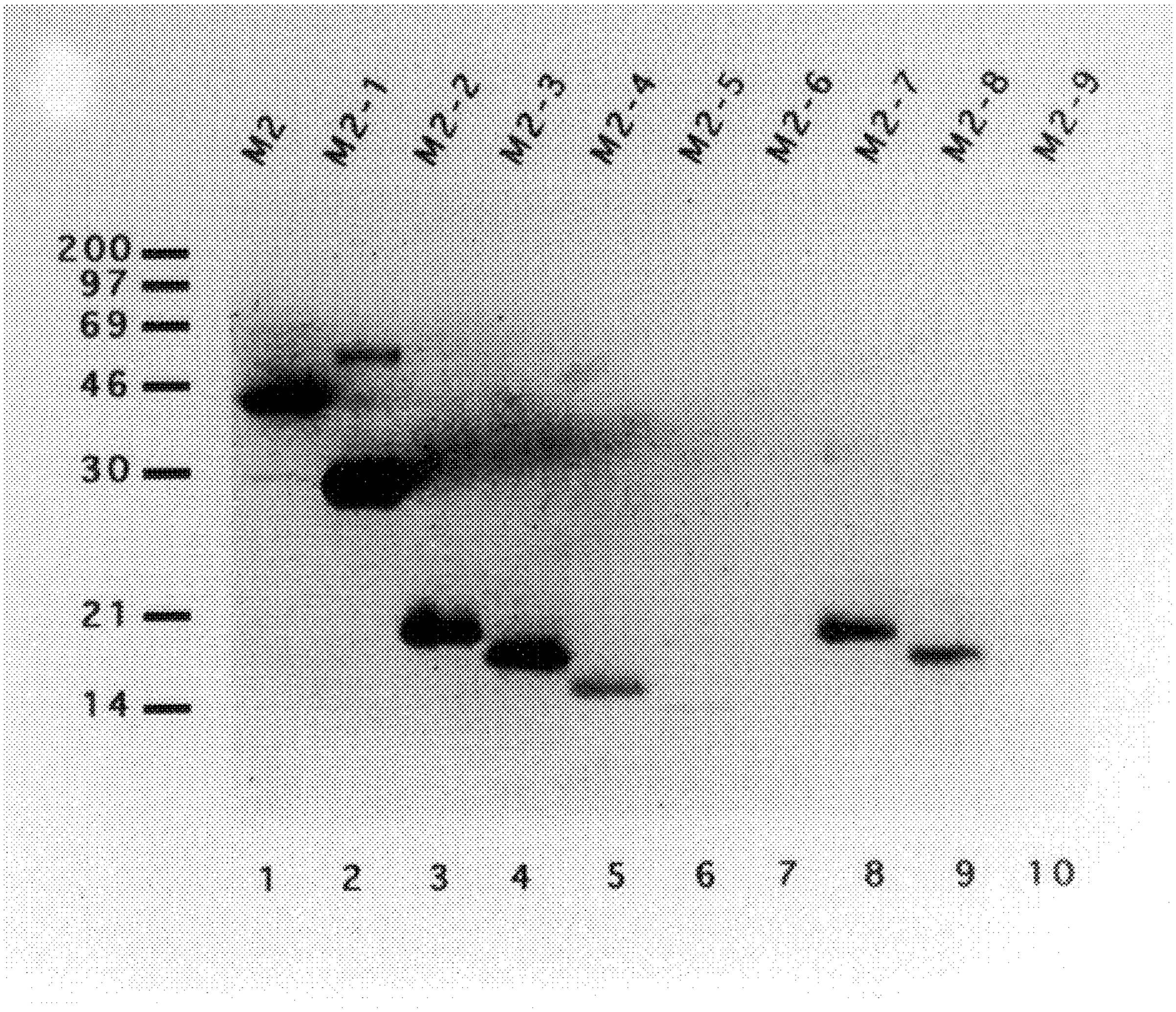
FIG. 35 is an electrophoretic photograph showing a result of ligand overlay assay for the truncation mutant M2. Positions of molecular weight marker proteins are shown on the left in kilodaltons.

The result is shown in FIG. 35. Strong binding signals were found with the first three mutants: M2-1 (847-1024), M2-2 (906-1024) and M2-3 (920-1024). The signal become weak with M2-4 (934-1024) and hardly visible with M2-5 (946-1024), and disappeared with M2-6 (974-1024).

Then, after deleting the C-terminals of M2-2 and M2-3, His-tagged proteins were prepared for M2-7 (906-1015), M2-8 (920-1015) and M2-9 (906-1004) in the same manner, and analyzed by the ligand overlay assay.

The result is shown in FIG. 35 (lanes 8–10). Deletion of 9 amino acids hardly affected [$^{35}$S]GTPγS-RhoA binding with M2-7 (906-1015) (lane 8) and M2-8 (920-1015) (lane 9), while no signal was found with M2-9 (906-1004) (lane 10).

Example 8

Identification of Rho-Binding Region by Yeast Two Hybrid System

Figure 36:
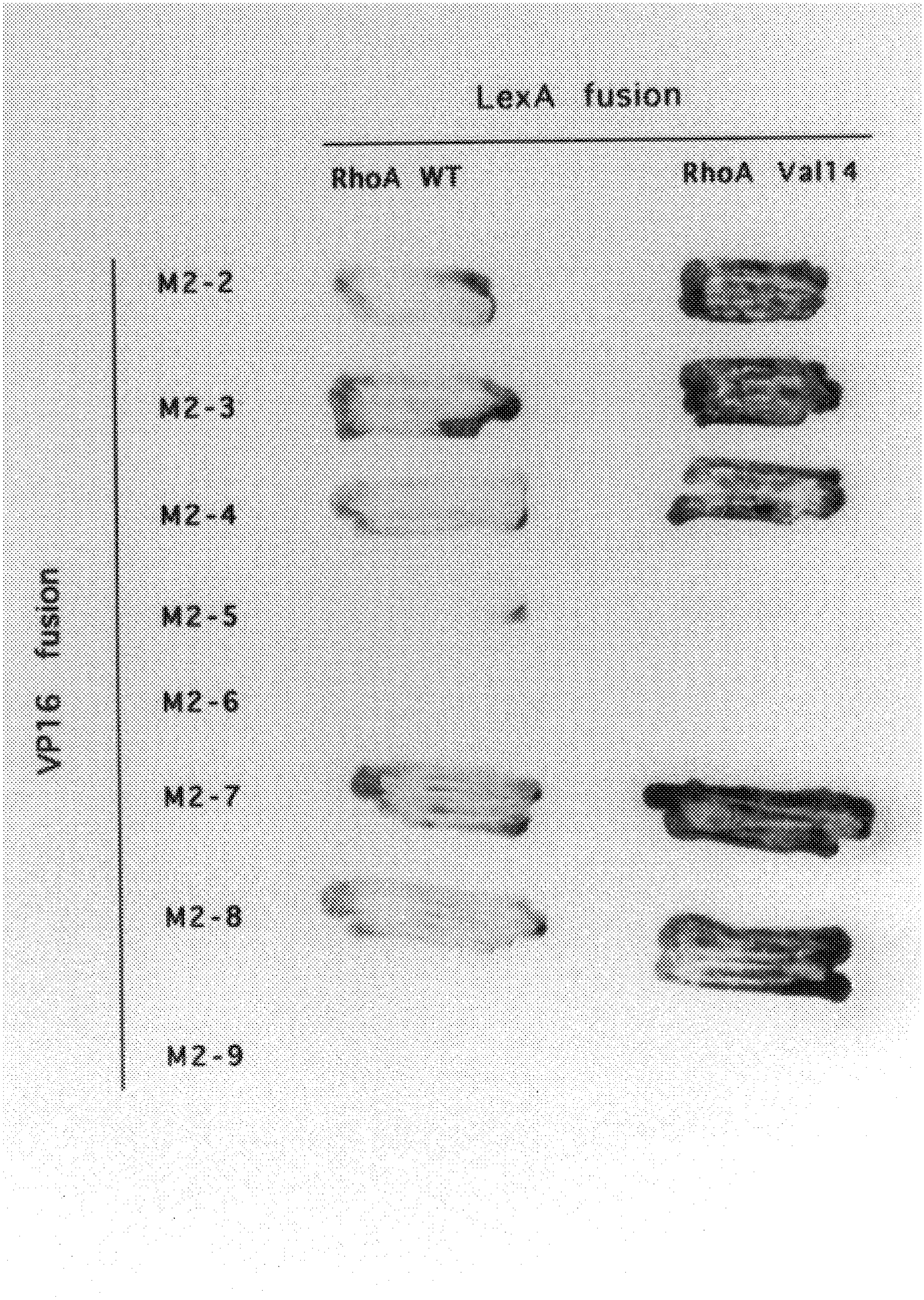
FIG. 36 is an photograph showing a result of two hybrid assay for the binding of the truncation mutant M2 to the Rho protein. Yeast L40 cells which express each truncation mutant protein fused to M2-VP16 transcription activating domain were mated to AMR70 cells which express RhoA or $RhoA^{Val14}$ fused to Lex A DNA-binding region.

In order to confirm the result of the ligand overlay assay, the yeast two hybrid assay was implemented on the truncation mutants of M2 (see example 7) as shown in FIG. 36. The mutants fused to the VP16-activation domain were expressed in yeast AMR70, which was mated with yeast L40 expressing RhoA or RhoA$^{Val14}$ fused to LexA DNA-binding domain. Binding was measured by β-galactosidase activity. The detailed procedure is as follows.

For the yeast two hybrid system, the BamHI-NotI fragments of each pQE plasmid DNA for M2-2 to M2-9 were inserted into pVP-16 (Vojtek, A. et al., Cell, 74, 205–214 (1993)). pBTM116 (Vojtek, A. et al., Cell, 74, 205–214 (1993)) was modified as described in Madaule, P. et al., FEBS Lett., 377, 243–248 (1995)*. The BamHI-EcoRI fragments of pGEX-RhoA and RhoA$^{Val14}$ were inserted into the BamHI and EcoRI sites of modified pBTM116 according to the method described above (Madaule, P. et al. (1995)*). The BamHI-BamHI fragment of pGEX-RhoB and -RhoC were inserted into the BamHI site of modified pBTM116 according to the method described above (Madaule, P. et al. (1995)*). Diploids obtained by mating AMR70 strains expressing the Rho-binding regions of various truncated mutants of p160 with L40 strain transformed with each BTM construct were assayed for β-galactosidase activity.

The result is shown in FIG. 36. M2-2, M2-3, M2-4, M2-7 and M2-8 were stained remarkably. Binding was stronger in RhoA$^{Val14}$ than in wild RhoA. The signal was faint in M2-5 and no signal was found with M2-6 and M2-9. Thus, the results obtained by the two hybrid system agreed to those of the ligand overlay assay (see example 7).

Example 9

Analysis of Rho-Binding Regions by Site-Specific M2 Mutants

The results of the overlay assay and the two hybrid system described in examples 7 and 8 implied that several regions of M2 assume key functions in binding to GTP-Rho. First, the disappearance of binding in M2-9 and significant reduction in M2-5 showed that two regions, i.e., the amino acid sequence 934-945 and 1005-1015 in SEQ ID NO: 2, play an essential role in recognize the Rho protein. Second, the reduction of binding in M2-4 indicated a possibility that the region 920-933 has a supportive role. However, the function of the intervening sequence (946-1004) remained unclear.

Figure 38:
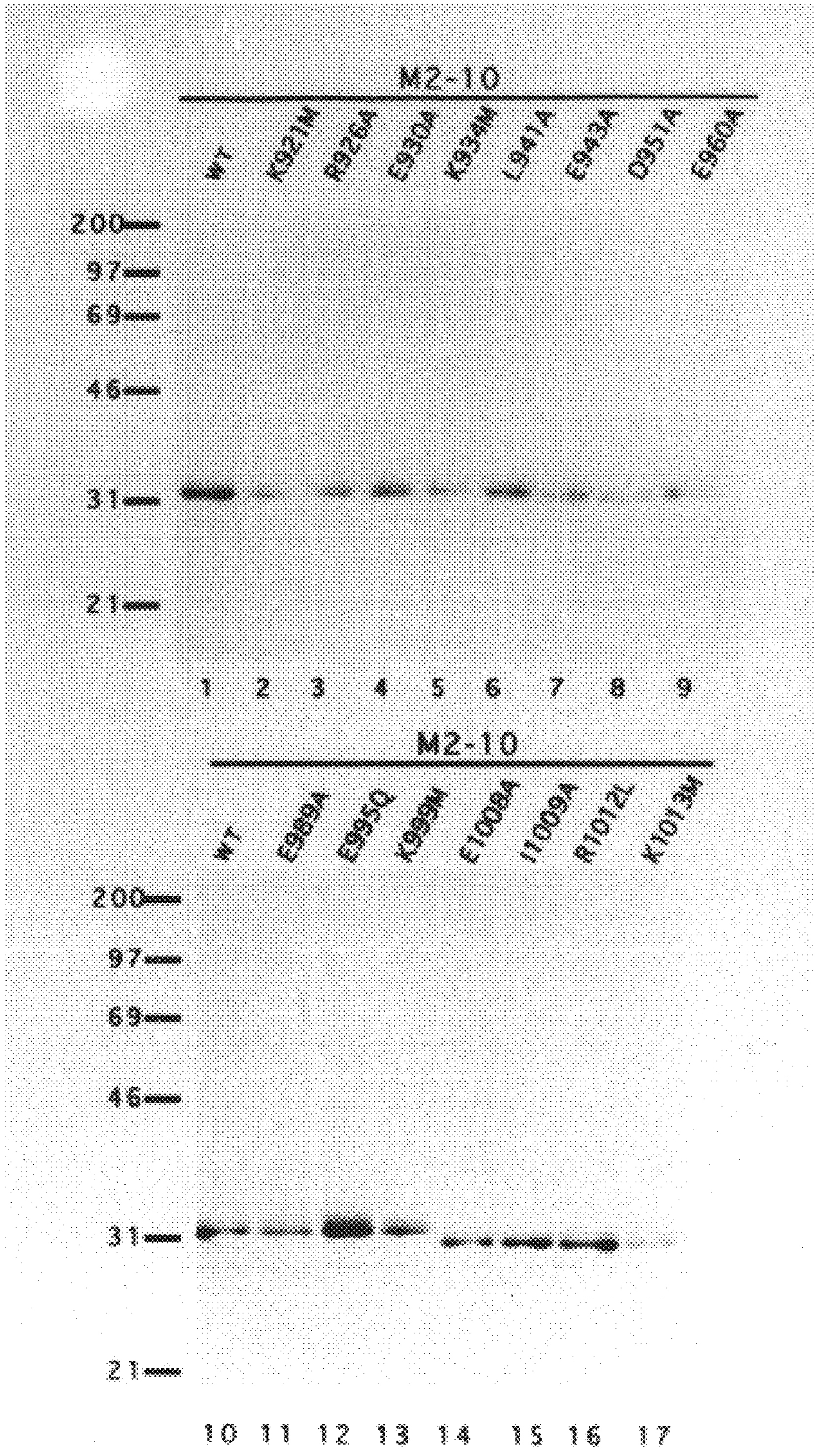
FIG. 38 is an electrophoretic photograph for M2-10 with point mutation (see example 9). Positions of molecular weight marker proteins are shown on the left in kilodaltons.

For further examination, the following experiment was conducted. In order to identify the amino acid residues necessary for binding to RhoA, several point mutations were introduced in M2-8 as shown in FIG. 37, and analyzed for their effect on GTP-Rho binding. The mutants were prepared by using the amino acid residues (mostly, hydrophilic amino acid residues) conserved by p160 and its homologue, ROKα (ROCK-II) (Leung, T. et al., J. Biol. Chem., 270, 29051–29054 (1995)*). These mutants were expressed as His-fusion proteins according to the method described in example 6 and purified. Almost the same amount of purified proteins was applied to SDS-PAGE used for the ligand overlay assay following SDS-PAGE as shown in FIG. 38. The detailed procedure is as follows.

Figure 31:
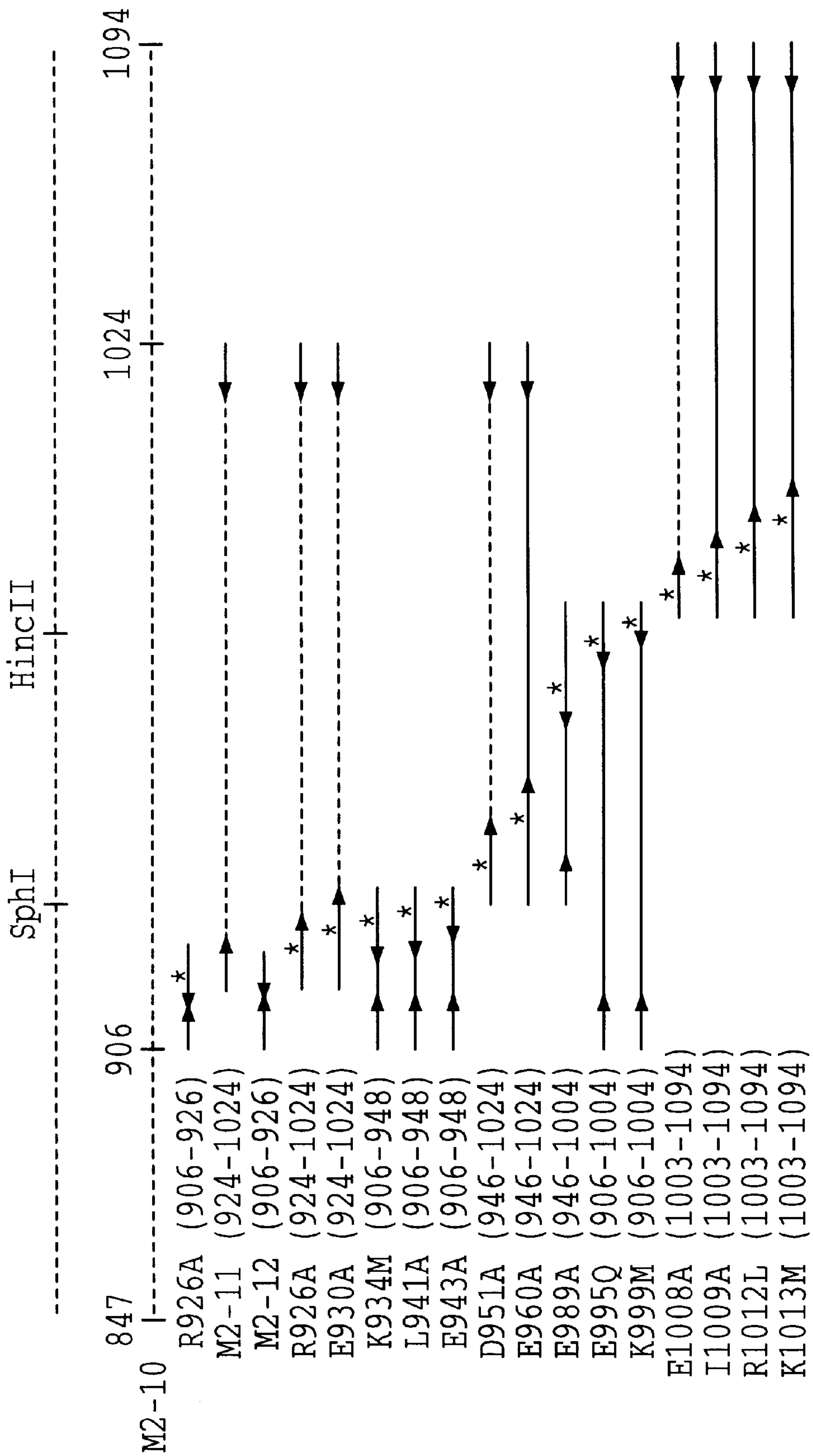
FIG. 31 shows PCR products used in construction of M2-10 mutants. Primers used in PCR are shown by arrows. Asterisks indicate positions of point mutation introduced by PCR. Restriction enzyme sites used are shown on the upper line. Amino acid positions in M2-10 corresponding to the PCR fragments are indicated in the middle line. The primer sequences used in PCR are shown in Table 2.

A total of 15 different point mutations were introduced into a cDNA corresponding to the amino acid sequence 906-1094 by replacing the wild-type sequence with those with each mutation as shown in FIG. 31. The wild-type fragment (906-1094) was first made by PCR using a primer pair (No. 8, Table 2 SEQ ID NOS:22 and 23).

TABLE 3

Primers used in constructions of M2- with point mutations.

| No. | Fragment | SEQ ID NO: | Sequence of 5' primer[a] |
|---|---|---|---|
| 8 | M2-10 | 22 | C GGG ATC CCC GAA GCT GAG CAA TAT TTC TCG |
| 9 | K921M | 24 | C GGG ATC CCC GGG TAC CGA GGC CTT CTG GAA GAA C |
| | M2-11 | 26 | CC CGG ATC CCT GCT AGC AGA AAT AGA CAA GAG ATT A |
| 11 | M2-12 | 28 | C GGG ATC CCC GGG TAC CGA GGC CTT CTG GAA GAA C |
| 12 | R926A | 30 | CC CGG ATC CCT GCT AGC GCA AAT AGA CAA GAG ATT ACA |
| 13 | E930A | 32 | CC CGG ATC CCT GCT AGC AGA AAT AGA CAA GCT AAT ACA GAT AAA GAT CAC A |
| 14 | K934M | 34 | C GGG ATC CCC GGG TAC CGA GGC CTT CTG GAA GAA C |
| 15 | L941A | 36 | C GGG ATC CCC GGG TAC CGA GGC CTT CTG GAA GAA C |
| 16 | E493A | 38 | C GGG ATC CCC GGG TAC CGA GGC CTT CTG GAA GAA C |
| 17 | D951A | 40 | C AGC ATG CTA ACC AAG GCC ATT GAA ATA TTA AGA AGA G GAT AAA GAT CAC A |
| 18 | E960A | 42 | C AGC ATG CTA ACC AAA GAT ATT GAG ATA TTA AGA AGA GAG AAT GCA GAG CTA ACA GAG AAA AT |
| 19 | E989A | 44 | G GGG ATC CCC AGC ATG CTA ACC AAA GAT ATT G |
| 20 | E995Q | 46 | C GGG ATC CCC GGG TAC CGA GGC CTT CTG GAA GAA C |
| 21 | K999M | 48 | C GGG ATC CCC GGG TAC CGA GGC CTT CTG GAA GAA C |
| 22 | E 08A | 50 | CT GTT AAC AAG CTT GCA GCA ATA ATG AAT CGA AAA GAT |
| 23 | I 09A | 52 | CT GTT AAC AAA TTG GCA GAG GCC ATG AAT CGA AAA GAT TTT AAA |
| 24 | R 12L | 54 | CT GTT AAC AAA TTG GCA GAA ATC ATG AAT CTA AAA GAT TTT AAA ATT GAT AG |
| 25 | K 13M | 56 | CT GTT AAC AAA TTG GCA GAA ATA ATG AAC CGG ATG GAT TTT AAA ATT GAT AGA AAG |

| No. | Fragment | SEQ ID NO: | Sequence of 3' primer[a] |
|---|---|---|---|
| 8 | M2- | 23 | TAA CCC GGG AAG TTT AGC ACG CAA TTG CTC |
| 9 | K921M | 25 | TCT GCT AGC AGC TTT CAT GCT TTC TTG CGT CAA T |
| | M2-11 | 27 | TA ACC CGG GTG TGT ATT AGC TTT CTT TCT ATC |
| 11 | M2-12 | 29 | TCT GCT AGC AGC TTT CTT GCT TT |
| 12 | R926A | 31 | TA ACC CGG GTG TGT ATT AGC TTT CTT TCT ATC |
| 13 | E930A | 33 | TA ACC CGG GTG TGT ATT AGC TTT CTT TCT ATC |
| 14 | K934M | 35 | T TAG CAT GAT GTT TGC TTC TTC AAG TCG ACT AAC AGT AAC AGT GTG ATC CA T ATC TGT AAT CTC TTG TCT |
| 15 | L941A | 37 | T TAG CAT GAT GTT TGC TTC TAC GGC CCG ACT AAC AGT GTG A |
| 16 | E493A | 39 | T TAG CAT GAT GTT TGC GGC CTC AAG CCG ACT AAC AG |
| 17 | D951A | 41 | TA ACC CGG GTG TGT ATT AGC TTT CTT TCT ATC |
| 18 | E960A | 45 | TA ACC CGG GTG TGT ATT AGC TTT CTT TCT ATC |
| 19 | E989A | 45 | TT GTT AAC AGC CTG TGT TTT AAG GGT ACG TTC AGT GTT GAT ATT CTT TGC AAA GGC AGC CTT AAG |
| 20 | E995Q | 47 | CT GTT AAC AGC CTG TTT AAG GGT ACG CTG AGT GTT GAT ATT CTT TTC |
| 21 | K999M | 49 | CT GTT AAC GGC CTG TGT CAT AAG GGT TCG TTC AGT GTT G |
| 22 | E 08A | 51 | TAA CCC GGG AAG TTT AGC ACG CAA TTG CTC |
| 23 | I 09A | 53 | TAA CCC GGG AAG TTT AGC ACG CAA TTG CTC |

TABLE 3-continued

| Primers used in constructions of M2- with point mutations. | | |
|---|---|---|
| 24 | R 12L | 55 TAA CCC GGG AAG TTT AGC ACG CAA TTG CTC |
| 25 | K 13M | 57 TAA CCC GGG AAG TTT AGC ACG CAA TTG CTC |

[a]All the sequences listed here are from 5' to 3' direction. Nucleotides corresponding to p160 sequence are underlined.

PCRs described in this paragraph were done using 95° C. for 2 min followed by 15 cycles of [1 min at 95° C., 1 min at 45° C., 1 min at 72° C.] followed by 72° C. for 2 min. The product was blunted, digested with BamHI and inserted into the BamHI and EcoRV sites of $pSK^-$ (Stratagene) ($pSK^-$-M2-10). The Asp718 fragment of $pSK^-$M2-10 (906-1094) was ligated into modified pQE-11.

To generate the first three mutants, cDNAs for K921M (906-926), M2-11 (924-1024), M2-12 (906-926), R926A (924-1024) and E930A (924-1024) were made by PCR using the primers shown in Table 2 (SEQ ID NOS:22–57, respectively). The products were then blunted, digested with BamHI and inserted into the BamHI and HincII sites of $pSK^+$ (Stratagene) ($pSK^+$-K921M (906-926), -M2-11 (924-1024), -M2-12 (906-926), -R926A (924-1024), -E930A (924-1024), respectively). To combine K921M (906-926) and -M2-11 (924-1024), the NheI-XhoI fragment of $pSK^+$-M2-11 (924-1024) was ligated into the NheI and XhoI sites of $pSK^+$-K921M (906-926). Similarly, the NheI-XhoI fragments of $pSK^+$-R926A (924-1024) and $pSK^+$-E930A (924-1024) were ligated into the NheI and XhoI sites of $pSK^+$-M2-12 (906-926). BamHI-HincII fragments of these $pSK^+$ (Stratagene) DNA were ligated into the BamHI and HincII sites of pQE-M2-10 (906-1094).

K934M, L941A and E943A mutations were introduced into cDNA corresponding to the amino acid sequence 906-948 in SEQ ID NO: 2 by PCR using primer pairs, No. 14, No. 15 and No. 16 (SEQ ID NOS:34 and 35, 36 and 37, 38 and 39), respectively. The BamHI-SphI fragments of the PCR products were then ligated into the BamHI and SphI sites of pQE-M2-10. D951A, E960A and E989A mutations were similarly made by PCR as shown in FIG. 31 using primer pairs No. 17, No. 18 and No. 19 (SEQ ID NOS:40 and 41, 42 and 43, 44 and 45), respectively. The SphI-HincII fragments of these products were then ligated into the SphI and HincII sites of pQE-M2-10. Two other mutations, E995Q and K999M, were similarly made by PCR as shown in FIG. 31 using primer pairs No. 20 and No. 21 (SEQ ID NOS:46 and 47, 48 and 49), respectively. The BamHI-HincII fragments of the PCR products were ligated into the BamHI and HincII sites of pQE-M2-10.

Sequences with four other mutations, E1008A (1003-1094), I1009A (1003-1094), R1012L (1003-1094) and K1013M (1003-1094), were amplified by PCR using primer pairs of No. 22, No. 23, No. 24 and No. 25 (SEQ ID NOS:50 and 51, 52 and 53, 54 and 55, 56 and 57), respectively. The products were blunted, digested with HincII and inserted into the HincII site of $pSK^+$ (Stratagene) ($pSK^+$-E1008A (1003-1094), -11009A (1003-1094), -R1012L (1003-1094) and -K1013M (1003-1094), respectively). The HincII-NotI fragments of these $pSK^+$ (Stratagene) plasmids were then ligated into the HincII and NotI sites of pQE-M2-10.

Figure 39:
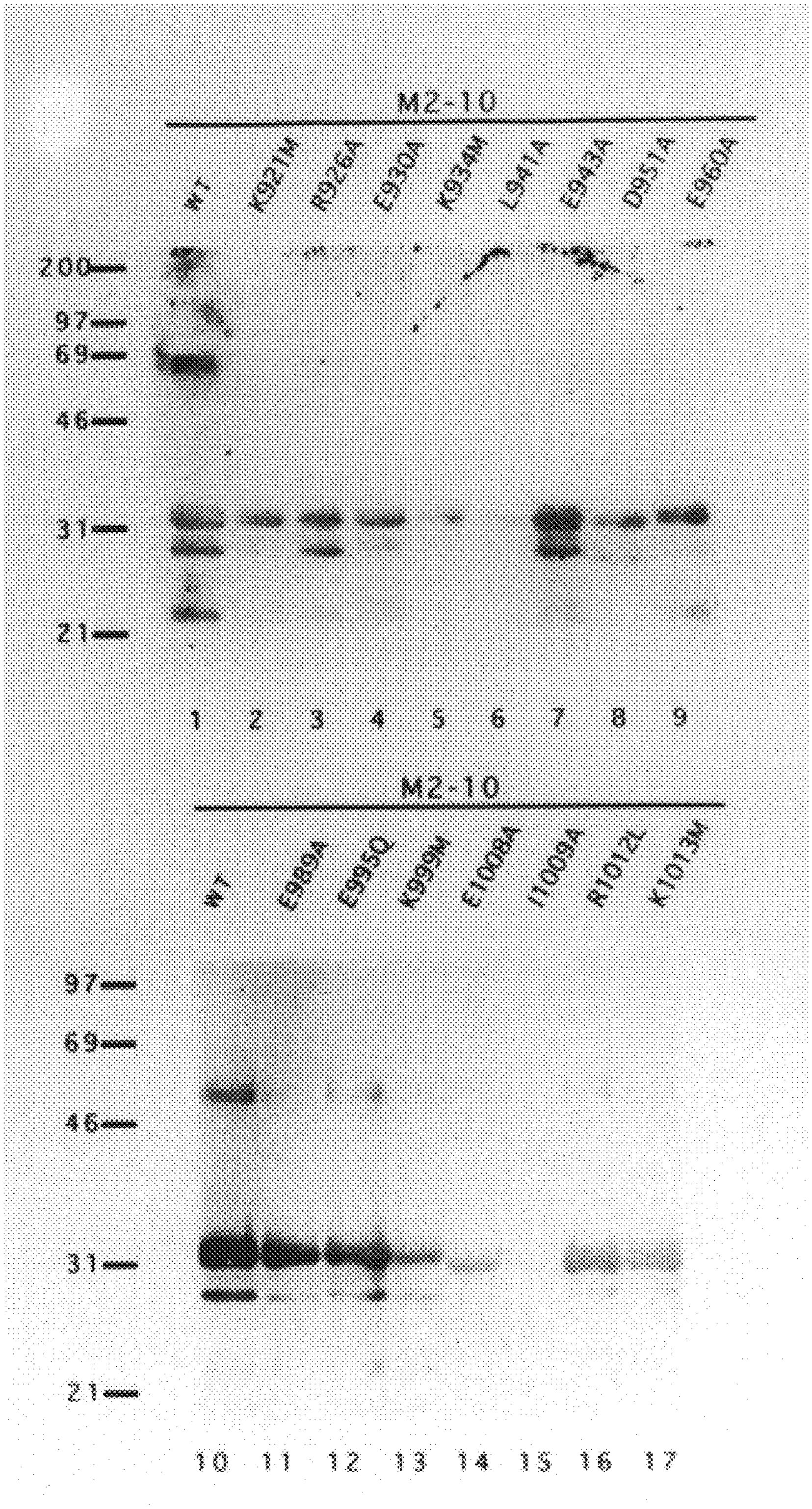
FIG. 39 is an electrophoretic photograph showing a result of ligand overlay assay of M2-10 with point mutation (see example 9). Positions of molecular weight marker proteins are shown on the left in kilodaltons.

The result is shown in FIG. 39. The strong signals observed with the wild type peptide (M2-10 (906-1094)) was significantly decreased by the K934M and L941A mutants located in the amino acid sequence 934-945 in SEQ ID NO: 2 as well as in the E1008A mutant, and disappeared with I1009A. The remaining bands appeared to be degradation products. The result agreed to the above hypothesis that the amino acid sequence 934-945 and 1004-1015 in SEQ ID NO: 2 are essential for RhoA-binding.

Example 10

Cytobiological Analysis of Rho-Binding Activity of Site-Specific Mutants of p160

Because the inventors failed to express KD fragments as recombinant proteins, the possibility cannot be denied that the KD region, in addition to the M2 region, has the Rho protein binding activity. Therefore, further investigation was conducted to see whether the M2 region is the only Rho protein binding domain in p160. First, wild type p160 and mutant p160 with E1008A, I1009A and R1012L (i.e., p160 having an intact KD region and a mutated M2 region) were expressed as a myc-tagged protein in COS cells. The produced proteins were coprecipitated with 9E10 anti-myc antibody, and analyzed by the ligand overlay assay. The detailed procedure is as follows.

For transfection to cultured cells, full length p160 cDNA with each mutation (E1008A, I1009A and R1012L) was constructed. Each SphI-BalI fragment of pQE plasmid (Quiagen) DNA encoding M2-10 (E1008A), M2-10 (I1009A) and M2-10 (R1012L) was inserted into the SphI and BalI sites of pSK plasmid carrying full length p160 cDNA (see example 4). An XhoI-SmaI fragment was excised from the resultant plasmid and then inserted into the XhoI and SmaI sites of a pCMX-myc-p160 (see example 4). COS-7 cells (ATCC CRL 1651) were plated at a density of $1.2\times10^5$ cells per 6 cm dish. After culture for 1 day, the medium was removed, and the cells were transfected with 3 $\mu$g of pCMX-myc, pCMX-myc-p160 wild type or mutant plasmid DNA using lipofectamine as described example 4. Cells were lysed and immunoprecipitates with anti-myc antibody were subjected to the immunoblotting and ligand overlay assay as described in examples 1 and 4.

Figure 40:
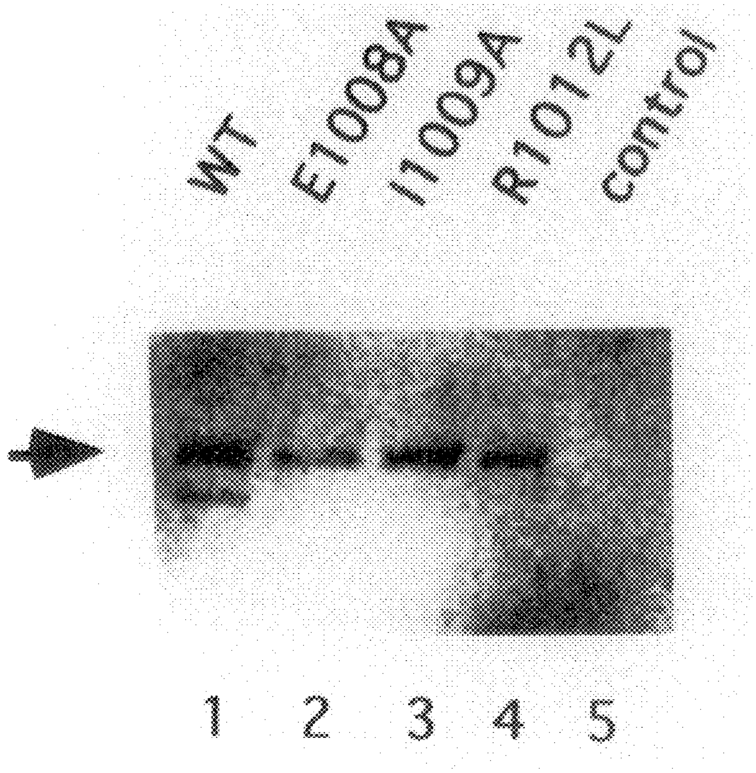
FIG. 40 is an electrophoretic photograph showing a result of immunoblotting, using anti-myc antibody, of immunoprecipitation of the mutated p160 expressed in COS-7 cells and anti-myc antibody.
Figure 41:
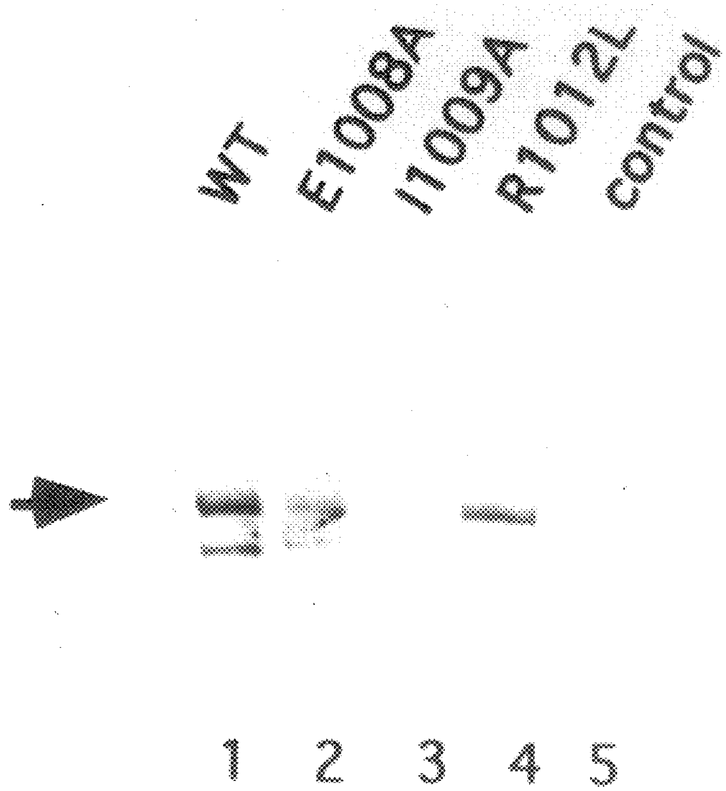
FIG. 41 is an electrophoretic photograph showing a result of ligand overlay assay, using $[^{35}S]GTP\gamma S$-Rho, of immunoprecipitation of the mutated p160 expressed in COS-7 cells and anti-myc antibody.

The result is shown in FIGS. 40 and 41. Each mutant (and wild type) of p160 was quantitatively recovered from the precipitate in the above procedure. Strong Rho-binding signals were observed with the wild type and the R1012L mutant. The signals were significantly reduced by the E1008A mutant, and disappeared with the I1009A mutant. These results indicated that the amino acid sequence 934-1015 in SEQ ID NO: 2 was the only Rho-binding domain in p160.

As described above, the minimum Rho-binding region was located on the amino acid sequence (the amino acid sequence 934-1015 in SEQ ID NO: 2) at the C-terminal of p160 $\alpha$-helix (examples 6–8). This region contained a leucine zipper-like motif (example 3). Also, residues essential for the Rho protein binding activity were identified in this region (examples 9 and 10). The amino acid sequence of this region is shown in FIG. 42 (SEQ ID NO:65).

What is claimed is:

1. An isolated protein comprising an amino acid sequence of SEQ ID NO: 2.

2. An isolated protein comprising a modified amino acid sequence of SEQ ID NO: 2 having activated Rho protein binding activity and protein kinase activity wherein the amino acid modification comprises at least one amino acid change selected from the group consisting of the substitution, deletion or both from position 1-71, substitution, deletion or both from position 344-933 and substitution, deletion or both from position 1016-1354.

3. A protein according to claim 2, wherein said modification comprises one or more deletions from a sequence selected from the group consisting of positions 1-71, 344-933, and 1016-1354.

4. A protein according to claim 2, wherein said modification comprises one or more deletions from a sequence selected from the group consisting of positions 1-71, 344-726, 344-846, 344-905, 344-919, 344-933, 1016-1354, 1022-1354, and 1025-1354.

5. A protein according to claim 2, wherein said substitution is selected from the group of substitutions consisting of K921M, R926A, and E930A.

6. An isolated protein comprising a modified amino acid sequence of SEQ ID NO: 2 having activated Rho protein binding activity and protein kinase activity, wherein the amino acid modification comprises at least one amino acid change selected from the group consisting of:

substitution, deletion, or both from position 1-71; substitution, deletion, or both from position 344-933; and substitution, deletion, or both from position 1016-1354, wherein the amino acid modification further comprises a substitution or deletion within a sequence region selected from the group consisting of the regions at positions 72-343 and 943-1015.

7. A protein according to claim 6, wherein said modification is a substitution selected from the group consisting of E943A, D951A, E960A, E989A, E995A, K999M, R1012L and K1013M.

8. A protein according to claim 7, wherein said substitution is R1012L.

9. An isolated protein comprising a modified amino acid sequence of SEQ ID NO: 2 having activated Rho protein binding activity and wherein the amino acid modification comprises at least one amino acid change selected from the group consisting of substitution, deletion or both from position 1-933 and/or position 1016-1354.

10. A protein according to claim 9, wherein said modification comprises a deletion of a sequence selected from the sequence group consisting of 1-71, 344-726, 344-846, 344-905, 344-919, 344-933, 1-933, 1016-1354, 1022-1354, and 1025-1354.

11. A protein according to claim 9, wherein said modification comprises a substitution selected from the group consisting of K921M, R926A, and B930A.

12. A protein according to claim 9, wherein said modified amino acid sequence lacks kinase activity.

13. A protein according to claim 12, wherein said modification comprises a deletion within sequence 72-343.

14. An isolated protein comprising a modified amino acid sequence of SEQ ID NO: 2 having activated Rho-binding activity and lacking kinase activity, wherein said modification comprises a deletion of amino acid change segment selected from the group consisting of 727-1024, 906-1024, 920-1024, 906-1015, 920-1015, and 906-1094.

15. A protein according to claim 9, wherein said modified amino acid sequence comprises an additional substitution selected from the group consisting of E943A, D951A, E960A, E989A, E995A, K999MK, R1012L and K1013M.

16. An isolated protein comprising a modified amino acid sequence of SEQ ID NO: 2 having protein kinase activity wherein the amino acid modification comprises at least one amino acid change selected from the group consisting of substitution from position 1-71, deletion from position 1-71, substitution from position 344-1354, and deletion from position 344-1354.

17. A protein according to claim 16, wherein said modified amino acid sequence comprises at least one deletion selected from the amino acid sequences located at position 1-71, position 344-1354, or from both.

18. A protein according to claim 16, wherein said modified amino acid sequence lacks activated Rho binding activity.

19. A protein according to claim 18, wherein said modification comprises an amino acid deletion or subtraction within position 934-945, position 1005-1015, or both.

20. A protein according to claim 16, wherein said modification comprises a deletion of at least one amino acid from a region selected from the group consisting of position 934-945 and position 1005-1015.

21. A protein according to claim 16, wherein said modification comprises at least one substitution selected from the group consisting of K934M, L941A, E1008A and I1009A.

22. A protein according to claim 18, wherein said modified amino acid sequence contains the wild-type sequence from position 72 to position 343 and comprises substitution E1008A and substitution I1009A.

23. A protein according to claim 14, further comprising at least one substitution selected from the group consisting of K921M, and R926A.

* * * * *

SEQUENCE LISTING (1) GENERAL INFORMATION:

(iii) NUMBER OF SEQUENCES: 68

(2) INFORMATION FOR SEQ ID NO:1:

(i) SEQUENCE CHARACTERISTICS:
(A) LENGTH: 4739 base pairs
(B) TYPE: nucleic acid
(C) STRANDEDNESS: single
(D) TOPOLOGY: linear (ix) FEATURE:
(A) NAME/KEY: CDS
(B) LOCATION: 448..4509

(xi) SEQUENCE DESCRIPTION: SEQ ID NO:1:

```
TCACCCGCCC TTTGCTTTCG CCTTTCCTCT TCTCCCTCCC TTGTTGCCCG GAGGAGTCTC     60

CACCCTGCTT CTCTTTCTCT ACCCGCTCCT GCCCATCTCG GGACGGGGAC CCCTCCATGG    120

CGACGGCGGC CGGGGCCCGC TAGACTGAAG CACCTCGCCG GAGCGACGAG GCTGGTGGCG    180

ACGGCGCTGT CGGCTGTCGT GAGGGGCTGC CGGGTGGGAT GCGACTTTGG GCGTCCGAGC    240

GGCTGTGGGT CGCTGTTGCC CCCGGCCCGG GGTCTGGAGA GCGGAGGTCC CCTCAGTGAG    300

GGGAAGACGG GGGAACCGGG CGCACCTGGT GACCCTGAGG TTCCGGCTCC TCCGCCCCGC    360

GGCTGCGAAC CCACCGCGGA GGAAGTTGGT TGAAATTGCT TTCCGCTGCT GGTGCTGGTA    420

AGAGGGCATT GTCACAGCAG CAGCAAC ATG TCG ACT GGG GAC AGT TTT GAG        471
                              Met Ser Thr Gly Asp Ser Phe Glu
                                1               5

ACT CGA TTT GAA AAA ATG GAC AAC CTG CTG CGG GAT CCC AAA TCG GAA      519
Thr Arg Phe Glu Lys Met Asp Asn Leu Leu Arg Asp Pro Lys Ser Glu
     10                  15                  20

GTG AAT TCG GAT TGT TTG CTG GAT GGA TTG GAT GCT TTG GTA TAT GAT      567
Val Asn Ser Asp Cys Leu Leu Asp Gly Leu Asp Ala Leu Val Tyr Asp
 25                  30                  35                  40

TTG GAT TTT CCT GCC TTA AGA AAA AAC AAA AAT ATT GAC AAC TTT TTA      615
Leu Asp Phe Pro Ala Leu Arg Lys Asn Lys Asn Ile Asp Asn Phe Leu
                 45                  50                  55

AGC AGA TAT AAA GAC ACA ATA AAT AAA ATC AGA GAT TTA CGA ATG AAA      663
Ser Arg Tyr Lys Asp Thr Ile Asn Lys Ile Arg Asp Leu Arg Met Lys
             60                  65                  70

GCT GAA GAT TAT GAA GTA GTG AAG GTG ATT GGT AGA GGT GCA TTT GGA      711
Ala Glu Asp Tyr Glu Val Val Lys Val Ile Gly Arg Gly Ala Phe Gly
         75                  80                  85

GAA GTT CAA TTG GTA AGG CAT AAA TCC ACC AGG AAG GTA TAT GCT ATG      759
Glu Val Gln Leu Val Arg His Lys Ser Thr Arg Lys Val Tyr Ala Met
     90                  95                 100

AAG CTT CTC AGC AAA TTT GAA ATG ATA AAG AGA TCT GAT TCT GCT TTT      807
Lys Leu Leu Ser Lys Phe Glu Met Ile Lys Arg Ser Asp Ser Ala Phe
105                 110                 115                 120

TTC TGG GAA GAA AGG GAC ATC ATG GCT TTT GCC AAC AGT CCT TGG GTT      855
Phe Trp Glu Glu Arg Asp Ile Met Ala Phe Ala Asn Ser Pro Trp Val
                125                 130                 135

GTT CAG CTT TTT TAT GCA TTC CAA GAT GAT CGT TAT CTC TAC ATG GTG      903
Val Gln Leu Phe Tyr Ala Phe Gln Asp Asp Arg Tyr Leu Tyr Met Val
            140                 145                 150

ATG GAA TAC ATG CCT GGT GGA GAT CTT GTA AAC TTA ATG AGC AAC TAT      951
Met Glu Tyr Met Pro Gly Gly Asp Leu Val Asn Leu Met Ser Asn Tyr
        155                 160                 165
```

-continued

```
GAT GTG CCT GAA AAA TGG GCA CGA TTC TAT ACT GCA GAA GTA GTT CTT      999
Asp Val Pro Glu Lys Trp Ala Arg Phe Tyr Thr Ala Glu Val Val Leu
    170                 175                 180

GCA TTG GAT GCA ATC CAT TCC ATG GGT TTT ATT CAC AGA GAT GTG AAG     1047
Ala Leu Asp Ala Ile His Ser Met Gly Phe Ile His Arg Asp Val Lys
185                 190                 195                 200

CCT GAT AAC ATG CTG CTG GAT AAA TCT GGA CAT TTG AAG TTA GCA GAT     1095
Pro Asp Asn Met Leu Leu Asp Lys Ser Gly His Leu Lys Leu Ala Asp
                205                 210                 215

TTT GGT ACT TGT ATG AAG ATG AAT AAG GAA GGC ATG GTA CGA TGT GAT     1143
Phe Gly Thr Cys Met Lys Met Asn Lys Glu Gly Met Val Arg Cys Asp
            220                 225                 230

ACA GCG GTT GGA ACA CCT GAT TAT ATT TCC CCT GAA GTA TTA AAA TCC     1191
Thr Ala Val Gly Thr Pro Asp Tyr Ile Ser Pro Glu Val Leu Lys Ser
        235                 240                 245

CAA GGT GGT GAT GGT TAT TAT GGA AGA GAA TGT GAC TGG TGG TCG GTT     1239
Gln Gly Gly Asp Gly Tyr Tyr Gly Arg Glu Cys Asp Trp Trp Ser Val
    250                 255                 260

GGG GTA TTT TTA TAC GAA ATG CTT GTA GGT GAT ACA CCT TTT TAT GCA     1287
Gly Val Phe Leu Tyr Glu Met Leu Val Gly Asp Thr Pro Phe Tyr Ala
265                 270                 275                 280

GAT TCT TTG GTT GGA ACT TAC AGT AAA ATT ATG AAC CAT AAA AAT TCA     1335
Asp Ser Leu Val Gly Thr Tyr Ser Lys Ile Met Asn His Lys Asn Ser
                285                 290                 295

CTT ACC TTT CCT GAT GAT AAT GAC ATA TCA AAA GAA GCA AAA AAC CTT     1383
Leu Thr Phe Pro Asp Asp Asn Asp Ile Ser Lys Glu Ala Lys Asn Leu
            300                 305                 310

ATT TGT GCC TTC CTT ACT GAC AGG GAA GTG AGG TTA GGG CGA AAT GGT     1431
Ile Cys Ala Phe Leu Thr Asp Arg Glu Val Arg Leu Gly Arg Asn Gly
        315                 320                 325

GTA GAA GAA ATC AAA CGA CAT CTC TTC TTC AAA AAT GAC CAG TGG GCT     1479
Val Glu Glu Ile Lys Arg His Leu Phe Phe Lys Asn Asp Gln Trp Ala
    330                 335                 340

TGG GAA ACG CTC CGA GAC ACT GTA GCA CCA GTT GTA CCC GAT TTA AGT     1527
Trp Glu Thr Leu Arg Asp Thr Val Ala Pro Val Val Pro Asp Leu Ser
345                 350                 355                 360

AGT GAC ATT GAT ACT AGT AAT TTT GAT GAC TTG GAA GAA GAT AAA GGA     1575
Ser Asp Ile Asp Thr Ser Asn Phe Asp Asp Leu Glu Glu Asp Lys Gly
                365                 370                 375

GAG GAA GAA ACA TTC CCT ATT CCT AAA GCT TTC GTT GGC AAT CAA CTA     1623
Glu Glu Glu Thr Phe Pro Ile Pro Lys Ala Phe Val Gly Asn Gln Leu
            380                 385                 390

CCT TTT GTA GGA TTT ACA TAT TAT AGC AAT CGT AGA TAC TTA TCT TCA     1671
Pro Phe Val Gly Phe Thr Tyr Tyr Ser Asn Arg Arg Tyr Leu Ser Ser
        395                 400                 405

GCA AAT CCT AAT GAT AAC AGA ACT AGC TCC AAT GCA GAT AAA AGC TTG     1719
Ala Asn Pro Asn Asp Asn Arg Thr Ser Ser Asn Ala Asp Lys Ser Leu
    410                 415                 420

CAG GAA AGT TTG CAA AAA ACA ATC TAT AAG CTG GAA GAA CAG CTG CAT     1767
Gln Glu Ser Leu Gln Lys Thr Ile Tyr Lys Leu Glu Glu Gln Leu His
425                 430                 435                 440

AAT GAA ATG CAG TTA AAA GAT GAA ATG GAG CAG AAG TGC AGA ACC TCA     1815
Asn Glu Met Gln Leu Lys Asp Glu Met Glu Gln Lys Cys Arg Thr Ser
                445                 450                 455

AAC ATA AAA CTA GAC AAG ATA ATG AAA GAA TTG GAT GAA GAG GGA AAT     1863
Asn Ile Lys Leu Asp Lys Ile Met Lys Glu Leu Asp Glu Glu Gly Asn
            460                 465                 470

CAA AGA AGA AAT CTA GAA TCT ACA GTG TCT CAG ATT GAG AAG GAG AAA     1911
Gln Arg Arg Asn Leu Glu Ser Thr Val Ser Gln Ile Glu Lys Glu Lys
        475                 480                 485
```

-continued

```
ATG TTG CTA CAG CAT AGA ATT AAT GAG TAC CAA AGA AAA GCT GAA CAG      1959
Met Leu Leu Gln His Arg Ile Asn Glu Tyr Gln Arg Lys Ala Glu Gln
    490                 495                 500

GAA AAT GAG AAG AGA AGA AAT GTA GAA AAT GAA GTT TCT ACA TTA AAG      2007
Glu Asn Glu Lys Arg Arg Asn Val Glu Asn Glu Val Ser Thr Leu Lys
505                 510                 515                 520

GAT CAG TTG GAA GAC TTA AAG AAA GTC AGT CAG AAT TCA CAG CTT GCT      2055
Asp Gln Leu Glu Asp Leu Lys Lys Val Ser Gln Asn Ser Gln Leu Ala
                525                 530                 535

AAT GAG AAG CTG TCC CAG TTA CAA AAG CAG CTA GAA GAA GCC AAT GAC      2103
Asn Glu Lys Leu Ser Gln Leu Gln Lys Gln Leu Glu Glu Ala Asn Asp
            540                 545                 550

TTA CTT AGG ACA GAA TCG GAC ACA GCT GTA AGA TTG AGG AAG AGT CAC      2151
Leu Leu Arg Thr Glu Ser Asp Thr Ala Val Arg Leu Arg Lys Ser His
        555                 560                 565

ACA GAG ATG AGC AAG TCA ATT AGT CAG TTA GAG TCC CTG AAC AGA GAG      2199
Thr Glu Met Ser Lys Ser Ile Ser Gln Leu Glu Ser Leu Asn Arg Glu
    570                 575                 580

TTG CAA GAG AGA AAT CGA ATT TTA GAG AAT TCT AAG TCA CAA ACA GAC      2247
Leu Gln Glu Arg Asn Arg Ile Leu Glu Asn Ser Lys Ser Gln Thr Asp
585                 590                 595                 600

AAA GAT TAT TAC CAG CTG CAA GCT ATA TTA GAA GCT GAA CGA AGA GAC      2295
Lys Asp Tyr Tyr Gln Leu Gln Ala Ile Leu Glu Ala Glu Arg Arg Asp
                605                 610                 615

AGA GGT CAT GAT TCT GAG ATG ATT GGA GAC CTT CAA GCT CGA ATT ACA      2343
Arg Gly His Asp Ser Glu Met Ile Gly Asp Leu Gln Ala Arg Ile Thr
            620                 625                 630

TCT TTA CAA GAG GAG GTG AAG CAT CTC AAA CAT AAT CTC GAA AAA GTG      2391
Ser Leu Gln Glu Glu Val Lys His Leu Lys His Asn Leu Glu Lys Val
        635                 640                 645

GAA GGA GAA AGA AAA GAG GCT CAA GAC ATG CTT AAT CAC TCA GAA AAG      2439
Glu Gly Glu Arg Lys Glu Ala Gln Asp Met Leu Asn His Ser Glu Lys
    650                 655                 660

GAA AAG AAT AAT TTA GAG ATA GAT TTA AAC TAC AAA CTT AAA TCA TTA      2487
Glu Lys Asn Asn Leu Glu Ile Asp Leu Asn Tyr Lys Leu Lys Ser Leu
665                 670                 675                 680

CAA CAA CGG TTA GAA CAA GAG GTA AAT GAA CAC AAA GTA ACC AAA GCT      2535
Gln Gln Arg Leu Glu Gln Glu Val Asn Glu His Lys Val Thr Lys Ala
                685                 690                 695

CGT TTA ACT GAC AAA CAT CAA TCT ATT GAA GAG GCA AAG TCT GTG GCA      2583
Arg Leu Thr Asp Lys His Gln Ser Ile Glu Glu Ala Lys Ser Val Ala
            700                 705                 710

ATG TGT GAG ATG GAA AAA AAG CTG AAA GAA GAA AGA GAA GCT CGA GAG      2631
Met Cys Glu Met Glu Lys Lys Leu Lys Glu Glu Arg Glu Ala Arg Glu
        715                 720                 725

AAG GCT GAA AAT CGG GTT GTT CAG ATT GAG AAA CAG TGT TCC ATG CTA      2679
Lys Ala Glu Asn Arg Val Val Gln Ile Glu Lys Gln Cys Ser Met Leu
    730                 735                 740

GAC GTT GAT CTG AAG CAA TCT CAG CAG AAA CTA GAA CAT TTG ACT GGA      2727
Asp Val Asp Leu Lys Gln Ser Gln Gln Lys Leu Glu His Leu Thr Gly
745                 750                 755                 760

AAT AAA GAA AGG ATG GAG GAT GAA GTT AAG AAT CTA ACC CTG CAA CTG      2775
Asn Lys Glu Arg Met Glu Asp Glu Val Lys Asn Leu Thr Leu Gln Leu
                765                 770                 775

GAG CAG GAA TCA AAT AAG CGG CTG TTG TTA CAA AAT GAA TTG AAG ACT      2823
Glu Gln Glu Ser Asn Lys Arg Leu Leu Leu Gln Asn Glu Leu Lys Thr
            780                 785                 790

CAA GCA TTT GAG GCA GAC AAT TTA AAA GGT TTA GAA AAG CAG ATG AAA      2871
Gln Ala Phe Glu Ala Asp Asn Leu Lys Gly Leu Glu Lys Gln Met Lys
        795                 800                 805
```

-continued

```
CAG GAA ATA AAT ACT TTA TTG GAA GCA AAG AGA TTA TTA GAA TTT GAG      2919
Gln Glu Ile Asn Thr Leu Leu Glu Ala Lys Arg Leu Leu Glu Phe Glu
    810                 815                 820

TTA GCT CAG CTT ACG AAA CAG TAT AGA GGA AAT GAA GGA CAG ATG CGG      2967
Leu Ala Gln Leu Thr Lys Gln Tyr Arg Gly Asn Glu Gly Gln Met Arg
825                 830                 835                 840

GAG CTA CAA GAT CAG CTT GAA GCT GAG CAA TAT TTC TCG ACA CTT TAT      3015
Glu Leu Gln Asp Gln Leu Glu Ala Glu Gln Tyr Phe Ser Thr Leu Tyr
                845                 850                 855

AAA ACC CAG GTA AAG GAA CTT AAA GAA GAA ATT GAA GAA AAA AAC AGA      3063
Lys Thr Gln Val Lys Glu Leu Lys Glu Glu Ile Glu Glu Lys Asn Arg
            860                 865                 870

GAA AAT TTA AAG AAA ATA CAG GAA CTA CAA AAT GAA AAA GAA ACT CTT      3111
Glu Asn Leu Lys Lys Ile Gln Glu Leu Gln Asn Glu Lys Glu Thr Leu
        875                 880                 885

GCT ACT CAG TTG GAT CTA GCA GAA ACA AAA GCT GAG TCT GAG CAG TTG      3159
Ala Thr Gln Leu Asp Leu Ala Glu Thr Lys Ala Glu Ser Glu Gln Leu
    890                 895                 900

GCG CGA GGC CTT CTG GAA GAA CAG TAT TTT GAA TTG ACG CAA GAA AGC      3207
Ala Arg Gly Leu Leu Glu Glu Gln Tyr Phe Glu Leu Thr Gln Glu Ser
905                 910                 915                 920

AAG AAA GCT GCT TCA AGA AAT AGA CAA GAG ATT ACA GAT AAA GAT CAC      3255
Lys Lys Ala Ala Ser Arg Asn Arg Gln Glu Ile Thr Asp Lys Asp His
                925                 930                 935

ACT GTT AGT CGG CTT GAA GAA GCA AAC AGC ATG CTA ACC AAA GAT ATT      3303
Thr Val Ser Arg Leu Glu Glu Ala Asn Ser Met Leu Thr Lys Asp Ile
            940                 945                 950

GAA ATA TTA AGA AGA GAG AAT GAA GAG CTA ACA GAG AAA ATG AAG AAG      3351
Glu Ile Leu Arg Arg Glu Asn Glu Glu Leu Thr Glu Lys Met Lys Lys
        955                 960                 965

GCA GAG GAA GAA TAT AAA CTG GAG AAG GAG GAG GAG ATC AGT AAT CTT      3399
Ala Glu Glu Glu Tyr Lys Leu Glu Lys Glu Glu Glu Ile Ser Asn Leu
    970                 975                 980

AAG GCT GCC TTT GAA AAG AAT ATC AAC ACT GAA CGA ACC CTT AAA ACA      3447
Lys Ala Ala Phe Glu Lys Asn Ile Asn Thr Glu Arg Thr Leu Lys Thr
985                 990                 995                 1000

CAG GCT GTT AAC AAA TTG GCA GAA ATA ATG AAT CGA AAA GAT TTT AAA      3495
Gln Ala Val Asn Lys Leu Ala Glu Ile Met Asn Arg Lys Asp Phe Lys
                1005                1010                1015

ATT GAT AGA AAG AAA GCT AAT ACA CAA GAT TTG AGA AAG AAA GAA AAG      3543
Ile Asp Arg Lys Lys Ala Asn Thr Gln Asp Leu Arg Lys Lys Glu Lys
            1020                1025                1030

GAA AAT CGA AAG CTG CAA CTG GAA CTC AAC CAA GAA AGA GAG AAA TTC      3591
Glu Asn Arg Lys Leu Gln Leu Glu Leu Asn Gln Glu Arg Glu Lys Phe
        1035                1040                1045

AAC CAG ATG GTA GTG AAA CAT CAG AAG GAA CTG AAT GAC ATG CAA GCG      3639
Asn Gln Met Val Val Lys His Gln Lys Glu Leu Asn Asp Met Gln Ala
    1050                1055                1060

CAA TTG GTA GAA GAA TGT GCA CAT AGG AAT GAG CTT CAG ATG CAG TTG      3687
Gln Leu Val Glu Glu Cys Ala His Arg Asn Glu Leu Gln Met Gln Leu
1065                1070                1075                1080

GCC AGC AAA GAG AGT GAT ATT GAG CAA TTG CGT GCT AAA CTT TTG GAC      3735
Ala Ser Lys Glu Ser Asp Ile Glu Gln Leu Arg Ala Lys Leu Leu Asp
                1085                1090                1095

CTC TCG GAT TCT ACA AGT GTT GCT AGT TTT CCT AGT GCT GAT GAA ACT      3783
Leu Ser Asp Ser Thr Ser Val Ala Ser Phe Pro Ser Ala Asp Glu Thr
            1100                1105                1110

GAT GGT AAC CTC CCA GAG TCA AGA ATT GAA GGT TGG CTT TCA GTA CCA      3831
Asp Gly Asn Leu Pro Glu Ser Arg Ile Glu Gly Trp Leu Ser Val Pro
        1115                1120                1125
```

-continued

```
AAT AGA GGA AAT ATC AAA CGA TAT GGC TGG AAG AAA CAG TAT GTT GTG      3879
Asn Arg Gly Asn Ile Lys Arg Tyr Gly Trp Lys Lys Gln Tyr Val Val
    1130                1135                1140

GTA AGC AGC AAA AAA ATT TTG TTC TAT AAT GAC GAA CAA GAT AAG GAG      3927
Val Ser Ser Lys Lys Ile Leu Phe Tyr Asn Asp Glu Gln Asp Lys Glu
1145                1150                1155                1160

CAA TCC AAT CCA TCT ATG GTA TTG GAC ATA GAT AAA CTG TTT CAC GTT      3975
Gln Ser Asn Pro Ser Met Val Leu Asp Ile Asp Lys Leu Phe His Val
                1165                1170                1175

AGA CCT GTA ACC CAA GGA GAT GTG TAT AGA GCT GAA ACT GAA GAA ATT      4023
Arg Pro Val Thr Gln Gly Asp Val Tyr Arg Ala Glu Thr Glu Glu Ile
            1180                1185                1190

CCT AAA ATA TTC CAG ATA CTA TAT GCA AAT GAA GGT GAA TGT AGA AAA      4071
Pro Lys Ile Phe Gln Ile Leu Tyr Ala Asn Glu Gly Glu Cys Arg Lys
        1195                1200                1205

GAT GTA GAG ATG GAA CCA GTA CAA CAA GCT GAA AAA ACT AAT TTC CAA      4119
Asp Val Glu Met Glu Pro Val Gln Gln Ala Glu Lys Thr Asn Phe Gln
    1210                1215                1220

AAT CAC AAA GGC CAT GAG TTT ATT CCT ACA CTC TAC CAC TTT CCT GCC      4167
Asn His Lys Gly His Glu Phe Ile Pro Thr Leu Tyr His Phe Pro Ala
1225                1230                1235                1240

AAT TGT GAT GCC TGT GCC AAA CCT CTC TGG CAT GTT TTT AAG CCA CCC      4215
Asn Cys Asp Ala Cys Ala Lys Pro Leu Trp His Val Phe Lys Pro Pro
                1245                1250                1255

CCT GCC CTA GAG TGT CGA AGA TGC CAT GTT AAG TGC CAC AGA GAT CAC      4263
Pro Ala Leu Glu Cys Arg Arg Cys His Val Lys Cys His Arg Asp His
            1260                1265                1270

TTA GAT AAG AAA GAG GAC TTA ATT TGT CCA TGT AAA GTA AGT TAT GAT      4311
Leu Asp Lys Lys Glu Asp Leu Ile Cys Pro Cys Lys Val Ser Tyr Asp
        1275                1280                1285

GTA ACA TCA GCA AGA GAT ATG CTG CTG TTA GCA TGT TCT CAG GAT GAA      4359
Val Thr Ser Ala Arg Asp Met Leu Leu Leu Ala Cys Ser Gln Asp Glu
    1290                1295                1300

CAA AAA AAA TGG GTA ACT CAT TTA GTA AAG AAA ATC CCT AAG AAT CCA      4407
Gln Lys Lys Trp Val Thr His Leu Val Lys Lys Ile Pro Lys Asn Pro
1305                1310                1315                1320

CCA TCT GGT TTT GTT CGT GCT TCC CCT CGA ACG CTT TCT ACA AGA TCC      4455
Pro Ser Gly Phe Val Arg Ala Ser Pro Arg Thr Leu Ser Thr Arg Ser
                1325                1330                1335

ACT GCA AAT CAG TCT TTC CGG AAA GTG GTC AAA AAT ACA TCT GGA AAA      4503
Thr Ala Asn Gln Ser Phe Arg Lys Val Val Lys Asn Thr Ser Gly Lys
            1340                1345                1350

ACT AGT TAACCATGTG ACTGAGTGCC CTGTGGAATC GTGTGGGATG CTACCTGATA       4559
Thr Ser

AACCAGGCTT CTTTAACCAT GCAGAAGCAG ACAGGCTGTT TCTTTGACAC AAATATCACA   4619

GGCTTCAGGG TTAAGATTGC TGTTTTTCTG TCCTTGCTTT GGCACAACAC ACTGAGGGTT   4679

TTTTTTATTG CGGGTTTGCC TACAGGTAGA TTAGATTAAT TATTACTATG TAATGCAAGT   4739
```

(2) INFORMATION FOR SEQ ID NO:2:

(i) SEQUENCE CHARACTERISTICS:
(A) LENGTH: 1354 amino acids
(B) TYPE: amino acid
(D) TOPOLOGY: linear (ii) MOLECULE TYPE: protein (xi) SEQUENCE DESCRIPTION: SEQ ID NO:2:

```
Met Ser Thr Gly Asp Ser Phe Glu Thr Arg Phe Glu Lys Met Asp Asn
  1               5                  10                  15
```

-continued

```
Leu Leu Arg Asp Pro Lys Ser Glu Val Asn Ser Asp Cys Leu Leu Asp
            20                  25                  30

Gly Leu Asp Ala Leu Val Tyr Asp Leu Asp Phe Pro Ala Leu Arg Lys
        35                  40                  45

Asn Lys Asn Ile Asp Asn Phe Leu Ser Arg Tyr Lys Asp Thr Ile Asn
    50                  55                  60

Lys Ile Arg Asp Leu Arg Met Lys Ala Glu Asp Tyr Glu Val Val Lys
65                  70                  75                  80

Val Ile Gly Arg Gly Ala Phe Gly Glu Val Gln Leu Val Arg His Lys
                85                  90                  95

Ser Thr Arg Lys Val Tyr Ala Met Lys Leu Leu Ser Lys Phe Glu Met
            100                 105                 110

Ile Lys Arg Ser Asp Ser Ala Phe Phe Trp Glu Glu Arg Asp Ile Met
        115                 120                 125

Ala Phe Ala Asn Ser Pro Trp Val Val Gln Leu Phe Tyr Ala Phe Gln
    130                 135                 140

Asp Asp Arg Tyr Leu Tyr Met Val Met Glu Tyr Met Pro Gly Gly Asp
145                 150                 155                 160

Leu Val Asn Leu Met Ser Asn Tyr Asp Val Pro Glu Lys Trp Ala Arg
                165                 170                 175

Phe Tyr Thr Ala Glu Val Val Leu Ala Leu Asp Ala Ile His Ser Met
            180                 185                 190

Gly Phe Ile His Arg Asp Val Lys Pro Asp Asn Met Leu Leu Asp Lys
        195                 200                 205

Ser Gly His Leu Lys Leu Ala Asp Phe Gly Thr Cys Met Lys Met Asn
    210                 215                 220

Lys Glu Gly Met Val Arg Cys Asp Thr Ala Val Gly Thr Pro Asp Tyr
225                 230                 235                 240

Ile Ser Pro Glu Val Leu Lys Ser Gln Gly Gly Asp Gly Tyr Tyr Gly
                245                 250                 255

Arg Glu Cys Asp Trp Trp Ser Val Gly Val Phe Leu Tyr Glu Met Leu
            260                 265                 270

Val Gly Asp Thr Pro Phe Tyr Ala Asp Ser Leu Val Gly Thr Tyr Ser
        275                 280                 285

Lys Ile Met Asn His Lys Asn Ser Leu Thr Phe Pro Asp Asp Asn Asp
    290                 295                 300

Ile Ser Lys Glu Ala Lys Asn Leu Ile Cys Ala Phe Leu Thr Asp Arg
305                 310                 315                 320

Glu Val Arg Leu Gly Arg Asn Gly Val Glu Glu Ile Lys Arg His Leu
                325                 330                 335

Phe Phe Lys Asn Asp Gln Trp Ala Trp Glu Thr Leu Arg Asp Thr Val
            340                 345                 350

Ala Pro Val Val Pro Asp Leu Ser Ser Asp Ile Asp Thr Ser Asn Phe
        355                 360                 365

Asp Asp Leu Glu Glu Asp Lys Gly Glu Glu Glu Thr Phe Pro Ile Pro
    370                 375                 380

Lys Ala Phe Val Gly Asn Gln Leu Pro Phe Val Gly Phe Thr Tyr Tyr
385                 390                 395                 400

Ser Asn Arg Arg Tyr Leu Ser Ser Ala Asn Pro Asn Asp Asn Arg Thr
                405                 410                 415

Ser Ser Asn Ala Asp Lys Ser Leu Gln Glu Ser Leu Gln Lys Thr Ile
            420                 425                 430

Tyr Lys Leu Glu Glu Gln Leu His Asn Glu Met Gln Leu Lys Asp Glu
        435                 440                 445
```

```
Met Glu Gln Lys Cys Arg Thr Ser Asn Ile Lys Leu Asp Lys Ile Met
    450                 455                 460

Lys Glu Leu Asp Glu Glu Gly Asn Gln Arg Arg Asn Leu Glu Ser Thr
465                 470                 475                 480

Val Ser Gln Ile Glu Lys Glu Lys Met Leu Leu Gln His Arg Ile Asn
                485                 490                 495

Glu Tyr Gln Arg Lys Ala Glu Gln Glu Asn Glu Lys Arg Arg Asn Val
            500                 505                 510

Glu Asn Glu Val Ser Thr Leu Lys Asp Gln Leu Glu Asp Leu Lys Lys
        515                 520                 525

Val Ser Gln Asn Ser Gln Leu Ala Asn Glu Lys Leu Ser Gln Leu Gln
    530                 535                 540

Lys Gln Leu Glu Glu Ala Asn Asp Leu Leu Arg Thr Glu Ser Asp Thr
545                 550                 555                 560

Ala Val Arg Leu Arg Lys Ser His Thr Glu Met Ser Lys Ser Ile Ser
                565                 570                 575

Gln Leu Glu Ser Leu Asn Arg Glu Leu Gln Glu Arg Asn Arg Ile Leu
            580                 585                 590

Glu Asn Ser Lys Ser Gln Thr Asp Lys Asp Tyr Tyr Gln Leu Gln Ala
        595                 600                 605

Ile Leu Glu Ala Glu Arg Arg Asp Arg Gly His Asp Ser Glu Met Ile
    610                 615                 620

Gly Asp Leu Gln Ala Arg Ile Thr Ser Leu Gln Glu Glu Val Lys His
625                 630                 635                 640

Leu Lys His Asn Leu Glu Lys Val Glu Gly Glu Arg Lys Glu Ala Gln
                645                 650                 655

Asp Met Leu Asn His Ser Glu Lys Glu Lys Asn Asn Leu Glu Ile Asp
            660                 665                 670

Leu Asn Tyr Lys Leu Lys Ser Leu Gln Gln Arg Leu Glu Gln Glu Val
        675                 680                 685

Asn Glu His Lys Val Thr Lys Ala Arg Leu Thr Asp Lys His Gln Ser
    690                 695                 700

Ile Glu Glu Ala Lys Ser Val Ala Met Cys Glu Met Glu Lys Lys Leu
705                 710                 715                 720

Lys Glu Glu Arg Glu Ala Arg Glu Lys Ala Glu Asn Arg Val Val Gln
                725                 730                 735

Ile Glu Lys Gln Cys Ser Met Leu Asp Val Asp Leu Lys Gln Ser Gln
            740                 745                 750

Gln Lys Leu Glu His Leu Thr Gly Asn Lys Glu Arg Met Glu Asp Glu
        755                 760                 765

Val Lys Asn Leu Thr Leu Gln Leu Glu Gln Glu Ser Asn Lys Arg Leu
    770                 775                 780

Leu Leu Gln Asn Glu Leu Lys Thr Gln Ala Phe Glu Ala Asp Asn Leu
785                 790                 795                 800

Lys Gly Leu Glu Lys Gln Met Lys Gln Glu Ile Asn Thr Leu Leu Glu
                805                 810                 815

Ala Lys Arg Leu Leu Glu Phe Glu Leu Ala Gln Leu Thr Lys Gln Tyr
            820                 825                 830

Arg Gly Asn Glu Gly Gln Met Arg Glu Leu Gln Asp Gln Leu Glu Ala
        835                 840                 845

Glu Gln Tyr Phe Ser Thr Leu Tyr Lys Thr Gln Val Lys Glu Leu Lys
    850                 855                 860

Glu Glu Ile Glu Glu Lys Asn Arg Glu Asn Leu Lys Lys Ile Gln Glu
```

-continued

```
865                 870                 875                 880

Leu Gln Asn Glu Lys Glu Thr Leu Ala Thr Gln Leu Asp Leu Ala Glu
                885                 890                 895

Thr Lys Ala Glu Ser Glu Gln Leu Ala Arg Gly Leu Leu Glu Glu Gln
            900                 905                 910

Tyr Phe Glu Leu Thr Gln Glu Ser Lys Lys Ala Ala Ser Arg Asn Arg
        915                 920                 925

Gln Glu Ile Thr Asp Lys Asp His Thr Val Ser Arg Leu Glu Glu Ala
    930                 935                 940

Asn Ser Met Leu Thr Lys Asp Ile Glu Ile Leu Arg Arg Glu Asn Glu
945                 950                 955                 960

Glu Leu Thr Glu Lys Met Lys Lys Ala Glu Glu Glu Tyr Lys Leu Glu
                965                 970                 975

Lys Glu Glu Glu Ile Ser Asn Leu Lys Ala Ala Phe Glu Lys Asn Ile
            980                 985                 990

Asn Thr Glu Arg Thr Leu Lys Thr Gln Ala Val Asn Lys Leu Ala Glu
        995                 1000                1005

Ile Met Asn Arg Lys Asp Phe Lys Ile Asp Arg Lys Lys Ala Asn Thr
    1010                1015                1020

Gln Asp Leu Arg Lys Lys Glu Lys Glu Asn Arg Lys Leu Gln Leu Glu
1025                1030                1035                1040

Leu Asn Gln Glu Arg Glu Lys Phe Asn Gln Met Val Val Lys His Gln
                1045                1050                1055

Lys Glu Leu Asn Asp Met Gln Ala Gln Leu Val Glu Glu Cys Ala His
            1060                1065                1070

Arg Asn Glu Leu Gln Met Gln Leu Ala Ser Lys Glu Ser Asp Ile Glu
        1075                1080                1085

Gln Leu Arg Ala Lys Leu Leu Asp Leu Ser Asp Ser Thr Ser Val Ala
    1090                1095                1100

Ser Phe Pro Ser Ala Asp Glu Thr Asp Gly Asn Leu Pro Glu Ser Arg
1105                1110                1115                1120

Ile Glu Gly Trp Leu Ser Val Pro Asn Arg Gly Asn Ile Lys Arg Tyr
                1125                1130                1135

Gly Trp Lys Lys Gln Tyr Val Val Val Ser Ser Lys Lys Ile Leu Phe
            1140                1145                1150

Tyr Asn Asp Glu Gln Asp Lys Glu Gln Ser Asn Pro Ser Met Val Leu
        1155                1160                1165

Asp Ile Asp Lys Leu Phe His Val Arg Pro Val Thr Gln Gly Asp Val
    1170                1175                1180

Tyr Arg Ala Glu Thr Glu Glu Ile Pro Lys Ile Phe Gln Ile Leu Tyr
1185                1190                1195                1200

Ala Asn Glu Gly Glu Cys Arg Lys Asp Val Glu Met Glu Pro Val Gln
                1205                1210                1215

Gln Ala Glu Lys Thr Asn Phe Gln Asn His Lys Gly His Glu Phe Ile
            1220                1225                1230

Pro Thr Leu Tyr His Phe Pro Ala Asn Cys Asp Ala Cys Ala Lys Pro
        1235                1240                1245

Leu Trp His Val Phe Lys Pro Pro Pro Ala Leu Glu Cys Arg Arg Cys
    1250                1255                1260

His Val Lys Cys His Arg Asp His Leu Asp Lys Lys Glu Asp Leu Ile
1265                1270                1275                1280

Cys Pro Cys Lys Val Ser Tyr Asp Val Thr Ser Ala Arg Asp Met Leu
                1285                1290                1295
```

-continued

```
Leu Leu Ala Cys Ser Gln Asp Glu Gln Lys Lys Trp Val Thr His Leu
            1300                1305                1310

Val Lys Lys Ile Pro Lys Asn Pro Pro Ser Gly Phe Val Arg Ala Ser
        1315                1320                1325

Pro Arg Thr Leu Ser Thr Arg Ser Thr Ala Asn Gln Ser Phe Arg Lys
    1330                1335                1340

Val Val Lys Asn Thr Ser Gly Lys Thr Ser
1345                1350
```

(2) INFORMATION FOR SEQ ID NO:3:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:3:

GGGGAGCTCA AGGTACCTCG AGTGGGGACA GTTTTGAG 38

(2) INFORMATION FOR SEQ ID NO:4:

(i) SEQUENCE CHARACTERISTICS:
(A) LENGTH: 30 base pairs
(B) TYPE: nucleic acid
(C) STRANDEDNESS: single
(D) TOPOLOGY: linear (xi) SEQUENCE DESCRIPTION: SEQ ID NO:4:

CGCCTGCAGG CTTTCATTCG TAAATCTCTG 30

(2) INFORMATION FOR SEQ ID NO:5:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:5:

GGGGAGCTCA AGGTACCTCG ACTGGGGACA GTTTTGAG 38

(2) INFORMATION FOR SEQ ID NO:6:

(i) SEQUENCE CHARACTERISTICS:
(A) LENGTH: 30 base pairs
(B) TYPE: nucleic acid
(C) STRANDEDNESS: single
(D) TOPOLOGY: linear (xi) SEQUENCE DESCRIPTION: SEQ ID NO:6:

CGCCTGCAGG CTTTCATTCG TAAATCTCTG 30

(2) INFORMATION FOR SEQ ID NO:7:

(i) SEQUENCE CHARACTERISTICS:
(A) LENGTH: 37 base pairs
(B) TYPE: nucleic acid
(C) STRANDEDNESS: single
(D) TOPOLOGY: linear (xi) SEQUENCE DESCRIPTION: SEQ ID NO:7:

GGGATCCCCG GTACCGAAGA TTATGAAGTA GTGAAGG 37

(2) INFORMATION FOR SEQ ID NO:8:

(i) SEQUENCE CHARACTERISTICS:
(A) LENGTH: 40 base pairs
(B) TYPE: nucleic acid
(C) STRANDEDNESS: single
(D) TOPOLOGY: linear (xi) SEQUENCE DESCRIPTION: SEQ ID NO:8:

TCAGCTAATT AGAGCTCTTT GATTTCTTCT ACACCATTTC 40

(2) INFORMATION FOR SEQ ID NO:9:

(i) SEQUENCE CHARACTERISTICS:
(A) LENGTH: 30 base pairs
(B) TYPE: nucleic acid
(C) STRANDEDNESS: single
(D) TOPOLOGY: linear (xi) SEQUENCE DESCRIPTION: SEQ ID NO:9:

GGGGAGCTCG ACATCTCTTC TTCAAAAATG 30

(2) INFORMATION FOR SEQ ID NO:10:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO:10:

CCTACAAAAG GTAGTTGA 18

(2) INFORMATION FOR SEQ ID NO:11:

(i) SEQUENCE CHARACTERISTICS:
(A) LENGTH: 33 base pairs
(B) TYPE: nucleic acid
(C) STRANDEDNESS: single
(D) TOPOLOGY: linear (xi) SEQUENCE DESCRIPTION: SEQ ID NO:11:

CGGGATCCCC GATAGAAAGA AAGCTAATAC ACA 33

(2) INFORMATION FOR SEQ ID NO:12:

(i) SEQUENCE CHARACTERISTICS:
(A) LENGTH: 30 base pairs
(B) TYPE: nucleic acid
(C) STRANDEDNESS: single
(D) TOPOLOGY: linear (xi) SEQUENCE DESCRIPTION: SEQ ID NO:12:

TAACCCGGGA AGTTTAGCAC GCAATTGCTC 30

(2) INFORMATION FOR SEQ ID NO:13:

(i) SEQUENCE CHARACTERISTICS:
(A) LENGTH: 32 base pairs
(B) TYPE: nucleic acid
(C) STRANDEDNESS: single
(D) TOPOLOGY: linear (xi) SEQUENCE DESCRIPTION: SEQ ID NO:13:

CCGGGATCCC CGAAGCTGAG CAATATTTCT CG 32

(2) INFORMATION FOR SEQ ID NO:14:

(i) SEQUENCE CHARACTERISTICS:
(A) LENGTH: 32 base pairs

-continued (B) TYPE: nucleic acid
(C) STRANDEDNESS: single
(D) TOPOLOGY: linear (xi) SEQUENCE DESCRIPTION: SEQ ID NO:14:

TAACCCGGGT GTGTATTAGC TTTCTTTCTA TC 32

(2) INFORMATION FOR SEQ ID NO:15:

(i) SEQUENCE CHARACTERISTICS:
(A) LENGTH: 35 base pairs
(B) TYPE: nucleic acid
(C) STRANDEDNESS: single
(D) TOPOLOGY: linear (xi) SEQUENCE DESCRIPTION: SEQ ID NO:15:

CGGGATCCCC GGGTACCGAG GCCTTCTGGA AGAAC 35

(2) INFORMATION FOR SEQ ID NO:16:

(i) SEQUENCE CHARACTERISTICS:
(A) LENGTH: 33 base pairs
(B) TYPE: nucleic acid
(C) STRANDEDNESS: single
(D) TOPOLOGY: linear (xi) SEQUENCE DESCRIPTION: SEQ ID NO:16:

CGGGATCCCC AAGAAAGCTG CTTCAAGAAA TAG 33

(2) INFORMATION FOR SEQ ID NO:17:

(i) SEQUENCE CHARACTERISTICS:
(A) LENGTH: 31 base pairs
(B) TYPE: nucleic acid
(C) STRANDEDNESS: single
(D) TOPOLOGY: linear (xi) SEQUENCE DESCRIPTION: SEQ ID NO:17:

CGGGATCCCC AAAGATCACA CTGTTAGTCG G 31

(2) INFORMATION FOR SEQ ID NO:18:

(i) SEQUENCE CHARACTERISTICS:
(A) LENGTH: 32 base pairs
(B) TYPE: nucleic acid
(C) STRANDEDNESS: single
(D) TOPOLOGY: linear (xi) SEQUENCE DESCRIPTION: SEQ ID NO:18:

GGGGATCCCC AGCATGCTAA CCAAAGATAT TG 32

(2) INFORMATION FOR SEQ ID NO:19:

(i) SEQUENCE CHARACTERISTICS:
(A) LENGTH: 29 base pairs
(B) TYPE: nucleic acid
(C) STRANDEDNESS: single
(D) TOPOLOGY: linear (xi) SEQUENCE DESCRIPTION: SEQ ID NO:19:

GGGGATCCCC AAACTGGAGA AGGAGGAGG 29

(2) INFORMATION FOR SEQ ID NO:20:

(i) SEQUENCE CHARACTERISTICS:
(A) LENGTH: 35 base pairs
(B) TYPE: nucleic acid
(C) STRANDEDNESS: single (D) TOPOLOGY: linear (xi) SEQUENCE DESCRIPTION: SEQ ID NO:20:

CGGGATCCCC GGGTACCGAG GCCTTCTGGA AGAAC 35

(2) INFORMATION FOR SEQ ID NO:21:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:21:

GCGAATTCGC GGCCGCTGTT AACAGCCTGT GTTTTAAG 38

(2) INFORMATION FOR SEQ ID NO:22:

(i) SEQUENCE CHARACTERISTICS:
(A) LENGTH: 31 base pairs
(B) TYPE: nucleic acid
(C) STRANDEDNESS: single
(D) TOPOLOGY: linear (xi) SEQUENCE DESCRIPTION: SEQ ID NO:22:

CGGGATCCCC GAAGCTGAGC AATATTTCTC G 31

(2) INFORMATION FOR SEQ ID NO:23:

(i) SEQUENCE CHARACTERISTICS:
(A) LENGTH: 30 base pairs
(B) TYPE: nucleic acid
(C) STRANDEDNESS: single
(D) TOPOLOGY: linear (xi) SEQUENCE DESCRIPTION: SEQ ID NO:23:

TAACCCGGGA AGTTTAGCAC GCAATTGCTC 30

(2) INFORMATION FOR SEQ ID NO:24:

(i) SEQUENCE CHARACTERISTICS:
(A) LENGTH: 35 base pairs
(B) TYPE: nucleic acid
(C) STRANDEDNESS: single
(D) TOPOLOGY: linear (xi) SEQUENCE DESCRIPTION: SEQ ID NO:24:

CGGGATCCCC GGGTACCGAG GCCTTCTGGA AGAAC 35

(2) INFORMATION FOR SEQ ID NO:25:

(i) SEQUENCE CHARACTERISTICS:
(A) LENGTH: 34 base pairs
(B) TYPE: nucleic acid
(C) STRANDEDNESS: single
(D) TOPOLOGY: linear (xi) SEQUENCE DESCRIPTION: SEQ ID NO:25:

TCTGCTAGCA GCTTTCATGC TTTCTTGCGT CAAT 34

(2) INFORMATION FOR SEQ ID NO:26:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:26:

CCCGGATCCC TGCTAGCAGA AATAGACAAG AGATTA 36

(2) INFORMATION FOR SEQ ID NO:27:

(i) SEQUENCE CHARACTERISTICS:
(A) LENGTH: 32 base pairs
(B) TYPE: nucleic acid
(C) STRANDEDNESS: single
(D) TOPOLOGY: linear (xi) SEQUENCE DESCRIPTION: SEQ ID NO:27:

TAACCCGGGT GTGTATTAGC TTTCTTTCTA TC 32

(2) INFORMATION FOR SEQ ID NO:28:

(i) SEQUENCE CHARACTERISTICS:
(A) LENGTH: 35 base pairs
(B) TYPE: nucleic acid
(C) STRANDEDNESS: single
(D) TOPOLOGY: linear (xi) SEQUENCE DESCRIPTION: SEQ ID NO:28:

CGGGATCCCC GGGTACCGAG GCCTTCTGGA AGAAC 35

(2) INFORMATION FOR SEQ ID NO:29:

(i) SEQUENCE CHARACTERISTICS:
(A) LENGTH: 23 base pairs
(B) TYPE: nucleic acid
(C) STRANDEDNESS: single
(D) TOPOLOGY: linear (xi) SEQUENCE DESCRIPTION: SEQ ID NO:29:

TCTGCTAGCA GCTTTCTTGC TTT 23

(2) INFORMATION FOR SEQ ID NO:30:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:30:

CCCGGATCCC TGCTAGCGCA AATAGACAAG AGATTACA 38

(2) INFORMATION FOR SEQ ID NO:31:

(i) SEQUENCE CHARACTERISTICS:
(A) LENGTH: 32 base pairs
(B) TYPE: nucleic acid
(C) STRANDEDNESS: single
(D) TOPOLOGY: linear (xi) SEQUENCE DESCRIPTION: SEQ ID NO:31:

TAACCCGGGT GTGTATTAGC TTTCTTTCTA TC 32

(2) INFORMATION FOR SEQ ID NO:32:

(i) SEQUENCE CHARACTERISTICS:
(A) LENGTH: 51 base pairs
(B) TYPE: nucleic acid
(C) STRANDEDNESS: single
(D) TOPOLOGY: linear (xi) SEQUENCE DESCRIPTION: SEQ ID NO:32:

CCCGGATCCC TGCTAGCAGA AATAGACAAG CTAATACAGA TAAAGATCAC A 51

(2) INFORMATION FOR SEQ ID NO:33:

(i) SEQUENCE CHARACTERISTICS:
(A) LENGTH: 32 base pairs
(B) TYPE: nucleic acid
(C) STRANDEDNESS: single
(D) TOPOLOGY: linear (xi) SEQUENCE DESCRIPTION: SEQ ID NO:33:

TAACCCGGGT GTGTATTAGC TTTCTTTCTA TC 32

(2) INFORMATION FOR SEQ ID NO:34:

(i) SEQUENCE CHARACTERISTICS:
(A) LENGTH: 35 base pairs
(B) TYPE: nucleic acid
(C) STRANDEDNESS: single
(D) TOPOLOGY: linear (xi) SEQUENCE DESCRIPTION: SEQ ID NO:34:

CGGGATCCCC GGGTACCGAG GCCTTCTGGA AGAAC 35

(2) INFORMATION FOR SEQ ID NO:35:

(i) SEQUENCE CHARACTERISTICS:
(A) LENGTH: 64 base pairs
(B) TYPE: nucleic acid
(C) STRANDEDNESS: single
(D) TOPOLOGY: linear (xi) SEQUENCE DESCRIPTION: SEQ ID NO:35:

TTAGCATGAT GTTTGCTTCT TCAAGTCGAC TAACAGTGTG ATCCATATCT GTAATCTCTT 60

GTCT 64

(2) INFORMATION FOR SEQ ID NO:36:

(i) SEQUENCE CHARACTERISTICS:
(A) LENGTH: 35 base pairs
(B) TYPE: nucleic acid
(C) STRANDEDNESS: single
(D) TOPOLOGY: linear (xi) SEQUENCE DESCRIPTION: SEQ ID NO:36:

CGGGATCCCC GGGTACCGAG GCCTTCTGGA AGAAC 35

(2) INFORMATION FOR SEQ ID NO:37:

(i) SEQUENCE CHARACTERISTICS:
(A) LENGTH: 41 base pairs
(B) TYPE: nucleic acid
(C) STRANDEDNESS: single
(D) TOPOLOGY: linear (xi) SEQUENCE DESCRIPTION: SEQ ID NO:37:

TTAGCATGAT GTTTGCTTCT ACGGCCCGAC TAACAGTGTG A 41

(2) INFORMATION FOR SEQ ID NO:38:

(i) SEQUENCE CHARACTERISTICS:
(A) LENGTH: 35 base pairs
(B) TYPE: nucleic acid
(C) STRANDEDNESS: single
(D) TOPOLOGY: linear (xi) SEQUENCE DESCRIPTION: SEQ ID NO:38:

CGGGATCCCC GGGTACCGAG GCCTTCTGGA AGAAC 35

(2) INFORMATION FOR SEQ ID NO:39:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:39:

TTAGCATGAT GTTTGCGGCC TCAAGCCGAC TAACAG 36

(2) INFORMATION FOR SEQ ID NO:40:

(i) SEQUENCE CHARACTERISTICS:
(A) LENGTH: 51 base pairs
(B) TYPE: nucleic acid
(C) STRANDEDNESS: single
(D) TOPOLOGY: linear (xi) SEQUENCE DESCRIPTION: SEQ ID NO:40:

CAGCATGCTA ACCAAGGCCA TTGAAATATT AAGAAGAGGA TAAAGATCAC A 51

(2) INFORMATION FOR SEQ ID NO:41:

(i) SEQUENCE CHARACTERISTICS:
(A) LENGTH: 32 base pairs
(B) TYPE: nucleic acid
(C) STRANDEDNESS: single
(D) TOPOLOGY: linear (xi) SEQUENCE DESCRIPTION: SEQ ID NO:41:

TAACCCGGGT GTGTATTAGC TTTCTTTCTA TC 32

(2) INFORMATION FOR SEQ ID NO:42:

(i) SEQUENCE CHARACTERISTICS:
(A) LENGTH: 63 base pairs
(B) TYPE: nucleic acid
(C) STRANDEDNESS: single
(D) TOPOLOGY: linear (xi) SEQUENCE DESCRIPTION: SEQ ID NO:42:

CAGCATGCTA ACCAAAGATA TTGAGATATT AAGAAGAGAG AATGCAGAGC TAACAGAGAA 60

AAT 63

(2) INFORMATION FOR SEQ ID NO:43:

(i) SEQUENCE CHARACTERISTICS:
(A) LENGTH: 32 base pairs
(B) TYPE: nucleic acid
(C) STRANDEDNESS: single
(D) TOPOLOGY: linear (xi) SEQUENCE DESCRIPTION: SEQ ID NO:43:

TAACCCGGGT GTGTATTAGC TTTCTTTCTA TC 32

(2) INFORMATION FOR SEQ ID NO:44:

(i) SEQUENCE CHARACTERISTICS:
(A) LENGTH: 32 base pairs
(B) TYPE: nucleic acid
(C) STRANDEDNESS: single
(D) TOPOLOGY: linear (xi) SEQUENCE DESCRIPTION: SEQ ID NO:44:

-continued

GGGGATCCCC AGCATGCTAA CCAAAGATAT TG 32

(2) INFORMATION FOR SEQ ID NO:45:

(i) SEQUENCE CHARACTERISTICS:
(A) LENGTH: 65 base pairs
(B) TYPE: nucleic acid
(C) STRANDEDNESS: single
(D) TOPOLOGY: linear (xi) SEQUENCE DESCRIPTION: SEQ ID NO:45:

TTGTTAACAG CCTGTGTTTT AAGGGTACGT TCAGTGTTGA TATTCTTTGC AAAGGCAGCC 60

TTAAG 65

(2) INFORMATION FOR SEQ ID NO:46:

(i) SEQUENCE CHARACTERISTICS:
(A) LENGTH: 35 base pairs
(B) TYPE: nucleic acid
(C) STRANDEDNESS: single
(D) TOPOLOGY: linear (xi) SEQUENCE DESCRIPTION: SEQ ID NO:46:

CGGGATCCCC GGGTACCGAG GCCTTCTGGA AGAAC 35

(2) INFORMATION FOR SEQ ID NO:47:

(i) SEQUENCE CHARACTERISTICS:
(A) LENGTH: 50 base pairs
(B) TYPE: nucleic acid
(C) STRANDEDNESS: single
(D) TOPOLOGY: linear (xi) SEQUENCE DESCRIPTION: SEQ ID NO:47:

CTGTTAACAG CCTGTGTTTT AAGGGTACGC TGAGTGTTGA TATTCTTTTC 50

(2) INFORMATION FOR SEQ ID NO:48:

(i) SEQUENCE CHARACTERISTICS:
(A) LENGTH: 35 base pairs
(B) TYPE: nucleic acid
(C) STRANDEDNESS: single
(D) TOPOLOGY: linear (xi) SEQUENCE DESCRIPTION: SEQ ID NO:48:

CGGGATCCCC GGGTACCGAG GCCTTCTGGA AGAAC 35

(2) INFORMATION FOR SEQ ID NO:49:

(i) SEQUENCE CHARACTERISTICS:
(A) LENGTH: 39 base pairs
(B) TYPE: nucleic acid
(C) STRANDEDNESS: single
(D) TOPOLOGY: linear (xi) SEQUENCE DESCRIPTION: SEQ ID NO:49:

CTGTTAACGG CCTGTGTCAT AAGGGTTCGT TCAGTGTTG 39

(2) INFORMATION FOR SEQ ID NO:50:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:50:

CTGTTAACAA GCTTGCAGCA ATAATGAATC GAAAAGAT 38

(2) INFORMATION FOR SEQ ID NO:51:

(i) SEQUENCE CHARACTERISTICS:
(A) LENGTH: 30 base pairs
(B) TYPE: nucleic acid
(C) STRANDEDNESS: single
(D) TOPOLOGY: linear (xi) SEQUENCE DESCRIPTION: SEQ ID NO:51:

TAACCCGGGA AGTTTAGCAC GCAATTGCTC 30

(2) INFORMATION FOR SEQ ID NO:52:

(i) SEQUENCE CHARACTERISTICS:
(A) LENGTH: 44 base pairs
(B) TYPE: nucleic acid
(C) STRANDEDNESS: single
(D) TOPOLOGY: linear (xi) SEQUENCE DESCRIPTION: SEQ ID NO:52:

CTGTTAACAA ATTGGCAGAG GCCATGAATC GAAAAGATTT TAAA 44

(2) INFORMATION FOR SEQ ID NO:53:

(i) SEQUENCE CHARACTERISTICS:
(A) LENGTH: 30 base pairs
(B) TYPE: nucleic acid
(C) STRANDEDNESS: single
(D) TOPOLOGY: linear (xi) SEQUENCE DESCRIPTION: SEQ ID NO:53:

TAACCCGGGA AGTTTAGCAC GCAATTGCTC 30

(2) INFORMATION FOR SEQ ID NO:54:

(i) SEQUENCE CHARACTERISTICS:
(A) LENGTH: 52 base pairs
(B) TYPE: nucleic acid
(C) STRANDEDNESS: single
(D) TOPOLOGY: linear (xi) SEQUENCE DESCRIPTION: SEQ ID NO:54:

CTGTTAACAA ATTGGCAGAA ATCATGAATC TAAAAGATTT TAAAATTGAT AG 52

(2) INFORMATION FOR SEQ ID NO:55:

(i) SEQUENCE CHARACTERISTICS:
(A) LENGTH: 30 base pairs
(B) TYPE: nucleic acid
(C) STRANDEDNESS: single
(D) TOPOLOGY: linear (xi) SEQUENCE DESCRIPTION: SEQ ID NO:55:

TAACCCGGGA AGTTTAGCAC GCAATTGCTC 30

(2) INFORMATION FOR SEQ ID NO:56:

(i) SEQUENCE CHARACTERISTICS:
(A) LENGTH: 56 base pairs
(B) TYPE: nucleic acid
(C) STRANDEDNESS: single
(D) TOPOLOGY: linear (xi) SEQUENCE DESCRIPTION: SEQ ID NO:56:

CTGTTAACAA ATTGGCAGAA ATAATGAACC GGATGGATTT TAAAATTGAT AGAAAG 56

(2) INFORMATION FOR SEQ ID NO:57:

(i) SEQUENCE CHARACTERISTICS:
(A) LENGTH: 30 base pairs
(B) TYPE: nucleic acid
(C) STRANDEDNESS: single
(D) TOPOLOGY: linear (xi) SEQUENCE DESCRIPTION: SEQ ID NO:57:

TAACCCGGGA AGTTTAGCAC GCAATTGCTC 30

(2) INFORMATION FOR SEQ ID NO:58:

(i) SEQUENCE CHARACTERISTICS:
(A) LENGTH: 420 amino acids
(B) TYPE: amino acid
(C) STRANDEDNESS: single
(D) TOPOLOGY: linear (xi) SEQUENCE DESCRIPTION: SEQ ID NO:58:

```
Met Ser Thr Gly Asp Ser Phe Glu Ile Arg Phe Glu Lys Met Asp Asn
1               5                   10                  15

Leu Leu Arg Asp Pro Lys Ser Glu Val Asn Ser Asp Cys Leu Leu Asp
            20                  25                  30

Gly Leu Asp Ala Leu Val Tyr Asp Leu Asp Phe Pro Ala Leu Arg Lys
        35                  40                  45

Asn Lys Asn Ile Asp Asn Phe Leu Ser Arg Tyr Lys Asp Thr Ile Asn
    50                  55                  60

Lys Ile Arg Asp Leu Arg Met Lys Ala Glu Asp Tyr Glu Val Val Lys
65                  70                  75                  80

Val Ile Gly Arg Gly Ala Phe Gly Glu Val Gln Leu Val Arg His Lys
                85                  90                  95

Ser Thr Arg Lys Val Tyr Ala Met Lys Leu Leu Ser Lys Phe Glu Met
            100                 105                 110

Ile Lys Arg Ser Asp Ser Ala Phe Phe Trp Glu Glu Arg Asp Ile Met
        115                 120                 125

Ala Phe Ala Asn Ser Pro Trp Val Val Gln Leu Phe Tyr Ala Phe Gln
    130                 135                 140

Asp Asp Arg Tyr Leu Tyr Met Val Met Glu Tyr Met Pro Gly Gly Asp
145                 150                 155                 160

Leu Val Asn Leu Met Ser Asn Tyr Asp Val Pro Glu Lys Trp Ala Arg
                165                 170                 175

Phe Tyr Ile Ala Glu Val Val Leu Ala Leu Asp Ala Ile His Ser Met
            180                 185                 190

Gly Phe Ile His Arg Asp Val Lys Pro Asp Asn Met Leu Leu Asp Lys
        195                 200                 205

Ser Gly His Leu Lys Leu Ala Asp Phe Gly Ile Cys Met Lys Met Asn
    210                 215                 220

Lys Glu Gly Met Val Arg Cys Asp Thr Ala Val Gly Thr Pro Asp Tyr
225                 230                 235                 240

Ile Ser Pro Glu Val Leu Lys Ser Gln Gly Gly Asp Gly Tyr Tyr Gly
                245                 250                 255

Arg Glu Cys Asp Trp Trp Ser Val Gly Val Phe Leu Tyr Glu Met Leu
            260                 265                 270

Val Gly Asp Thr Pro Phe Tyr Ala Asp Ser Leu Val Gly Thr Tyr Ser
        275                 280                 285

Lys Ile Met Asn His Lys Asn Ser Leu Thr Phe Pro Asp Asp Asn Asp
    290                 295                 300
```

```
Ile Ser Lys Glu Ala Lys Asn Leu Ile Cys Ala Phe Leu Thr Asp Arg
305                 310                 315                 320

Glu Val Arg Leu Gly Arg Asn Gly Val Glu Glu Ile Lys Arg His Leu
                325                 330                 335

Phe Phe Lys Asn Asp Gln Trp Ala Trp Glu Thr Leu Arg Asp Ile Val
            340                 345                 350

Ala Pro Val Val Pro Asp Leu Ser Ser Asp Ile Asp Thr Ser Asn Phe
        355                 360                 365

Asp Asp Leu Glu Glu Asp Lys Gly Glu Glu Glu Thr Phe Pro Ile Pro
    370                 375                 380

Lys Ala Phe Val Gly Asn Gln Leu Pro Phe Val Gly Phe Thr Tyr Tyr
385                 390                 395                 400

Ser Asn Arg Arg Tyr Leu Ser Ser Ala Asn Pro Asn Asp Asn Arg Thr
                405                 410                 415

Ser Ser Asn Ala
            420
```

(2) INFORMATION FOR SEQ ID NO:59:

(i) SEQUENCE CHARACTERISTICS:
(A) LENGTH: 420 amino acids
(B) TYPE: amino acid
(C) STRANDEDNESS: single
(D) TOPOLOGY: linear (xi) SEQUENCE DESCRIPTION: SEQ ID NO:59:

```
Met Ser Ala Glu Val Arg Leu Arg Arg Leu Gln Gln Leu Val Ile Asp
1               5                   10                  15

Pro Gly Phe Leu Gly Leu Glu Pro Leu Leu Asp Leu Leu Leu Gly Val
            20                  25                  30

His Gln Glu Leu Gly Ala Ser Glu Leu Ala Gln Asp Lys Tyr Val Ala
        35                  40                  45

Asp Glu Leu Gln Trp Ala Glu Pro Ile Val Val Arg Leu Lys Glu Val
    50                  55                  60

Arg Leu Gln Arg Asp Asp Phe Glu Ile Leu Lys Val Ile Gly Arg Gly
65                  70                  75                  80

Ala Phe Ser Glu Val Ala Val Val Lys Met Lys Gln Thr Gly Gln Val
                85                  90                  95

Tyr Ala Met Lys Ile Met Asn Lys Trp Asp Met Leu Lys Arg Gly Glu
            100                 105                 110

Val Ser Cys Phe Arg Glu Glu Arg Asp Val Leu Val Asn Gly Asp Arg
        115                 120                 125

Arg Trp Ile Thr Gln Leu His Phe Ala Phe Gln Asp Glu Asn Tyr Leu
    130                 135                 140

Tyr Leu Val Met Glu Tyr Tyr Val Gly Gly Asp Leu Leu Thr Leu Leu
145                 150                 155                 160

Ser Lys Phe Gly Glu Arg Ile Pro Ala Glu Met Ala Arg Phe Tyr Leu
                165                 170                 175

Ala Glu Ile Val Met Ala Ile Asp Ser Val His Arg Leu Gly Tyr Val
            180                 185                 190

His Arg Asp Ile Lys Pro Asp Asn Ile Leu Leu Asp Arg Cys Gly His
        195                 200                 205

Ile Arg Leu Ala Asp Phe Gly Ser Cys Leu Lys Leu Arg Ala Asp Gly
    210                 215                 220

Ile Val Arg Ser Leu Val Ala Val Gly Thr Pro Asp Tyr Leu Ser Pro
225                 230                 235                 240
```

```
Glu Ile Leu Gln Ala Val Gly Gly Gly Pro Gly Thr Gly Ser Tyr Gly
                245                 250                 255

Pro Glu Cys Asp Trp Trp Ala Leu Gly Val Phe Ala Tyr Glu Met Phe
            260                 265                 270

Tyr Gly Cys Thr Pro Phe Tyr Ala Asp Ser Thr Ala Glu Thr Tyr Gly
        275                 280                 285

Lys Ile Val His Tyr Lys Glu His Leu Ser Leu Pro Leu Val Asp Glu
    290                 295                 300

Gly Val Pro Glu Glu Ala Arg Asp Phe Ile Gln Arg Leu Leu Cys Pro
305                 310                 315                 320

Pro Glu Ile Arg Leu Gly Arg Gly Gly Ala Gly Asp Phe Arg Thr His
                325                 330                 335

Pro Phe Phe Phe Gly Leu Asp Trp Asp Gly Leu Arg Asp Ser Val Pro
            340                 345                 350

Pro Phe Thr Pro Asp Phe Glu Gly Ala Thr Asp Thr Cys Asn Phe Asp
        355                 360                 365

Leu Val Glu Asp Gly Leu Thr Ala Met Glu Thr Leu Ser Asp Ile Arg
    370                 375                 380

Glu Gly Ala Pro Leu Gly Val His Leu Pro Phe Val Gly Tyr Ser Tyr
385                 390                 395                 400

Ser Cys Met Ala Leu Arg Asp Ser Glu Val Pro Gly Pro Thr Pro Met
                405                 410                 415

Glu Leu Glu Ala
            420
```

(2) INFORMATION FOR SEQ ID NO:60:

(i) SEQUENCE CHARACTERISTICS:
(A) LENGTH: 137 amino acids
(B) TYPE: amino acid
(C) STRANDEDNESS: single
(D) TOPOLOGY: linear (xi) SEQUENCE DESCRIPTION: SEQ ID NO:60:

```
Asp Gly Asn Leu Pro Glu Ser Arg Ile Glu Gly Trp Leu Ser Val Pro
1               5                   10                  15

Asn Arg Gly Asn Ile Lys Arg Tyr Gly Trp Lys Lys Gln Tyr Val Val
            20                  25                  30

Val Ser Ser Lys Lys Ile Leu Phe Tyr Asn Asp Glu Gln Asp Lys Glu
        35                  40                  45

Gln Ser Asn Pro Ser Met Val Leu Asp Ile Asp Lys Leu Phe His Val
    50                  55                  60

Arg Pro Val Thr Gln Gly Asp Val Tyr Arg Ala Glu Thr Glu Glu Ile
65                  70                  75                  80

Pro Lys Ile Phe Gln Ile Leu Tyr Ala Asn Glu Gly Glu Cys Arg Lys
                85                  90                  95

Asp Val Cys Pro Cys Lys Val Ser Tyr Asp Val Thr Ser Ala Arg Asp
            100                 105                 110

Met Leu Leu Leu Ala Cys Ser Gln Asp Glu Gln Lys Lys Trp Val Thr
        115                 120                 125

His Leu Val Lys Lys Ile Pro Lys Asn
    130                 135
```

(2) INFORMATION FOR SEQ ID NO:61:

(i) SEQUENCE CHARACTERISTICS:
(A) LENGTH: 111 amino acids (B) TYPE: amino acid
(C) STRANDEDNESS: single
(D) TOPOLOGY: linear (xi) SEQUENCE DESCRIPTION: SEQ ID NO:61:

```
Asp Ala Phe Tyr Lys Asn Ile Val Lys Lys Gly Tyr Leu Leu Lys Lys
1               5                   10                  15

Gly Lys Gly Lys Arg Trp Lys Asn Leu Tyr Phe Ile Leu Glu Gly Ser
            20                  25                  30

Asp Ala Gln Leu Ile Tyr Phe Glu Ser Glu Lys Arg Ala Thr Lys Pro
        35                  40                  45

Lys Gly Leu Ile Asp Leu Ser Val Cys Ser Val Tyr Val Val His Asp
    50                  55                  60

Ser Leu Phe Gly Arg Pro Asn Cys Phe Gln Ile Val Val Gln His Phe
65                  70                  75                  80

Ser Glu Glu His Tyr Ile Phe Tyr Phe Ala Gly Glu Thr Pro Glu Gln
                85                  90                  95

Ala Glu Asp Trp Met Lys Gly Leu Gln Ala Phe Cys Asn Leu Arg
            100                 105                 110
```

(2) INFORMATION FOR SEQ ID NO:62:

(i) SEQUENCE CHARACTERISTICS:
(A) LENGTH: 110 amino acids
(B) TYPE: amino acid
(C) STRANDEDNESS: single
(D) TOPOLOGY: linear (xi) SEQUENCE DESCRIPTION: SEQ ID NO:62:

```
Leu Ala Asn Tyr Gly Arg Pro Lys Ile Asp Gly Glu Leu Lys Ile Thr
1               5                   10                  15

Ser Val Glu Arg Arg Ser Lys Thr Asp Arg Tyr Ala Phe Leu Leu Asp
            20                  25                  30

Lys Ala Leu Leu Ile Cys Lys Arg Arg Gly Asp Ser Tyr Asp Leu Lys
        35                  40                  45

Ala Ser Val Asn Leu His Ser Phe Gln Val Arg Asp Asp Ser Ser Gly
    50                  55                  60

Glu Arg Asp Asn Lys Lys Trp Ser His Met Phe Leu Leu Ile Glu Asp
65                  70                  75                  80

Gln Gly Ala Gln Gly Tyr Glu Leu Phe Phe Lys Thr Arg Glu Leu Lys
                85                  90                  95

Lys Lys Trp Met Glu Gln Phe Glu Met Ala Ile Ser Asn Ile
            100                 105                 110
```

(2) INFORMATION FOR SEQ ID NO:63:

(i) SEQUENCE CHARACTERISTICS:
(A) LENGTH: 53 amino acids
(B) TYPE: amino acid
(C) STRANDEDNESS: single
(D) TOPOLOGY: linear (xi) SEQUENCE DESCRIPTION: SEQ ID NO:63:

```
His Glu Phe Ile Pro Thr Leu Tyr His Phe Pro Ala Asn Cys Asp Ala
1               5                   10                  15

Cys Ala Lys Pro Leu Trp His Val Phe Lys Pro Pro Pro Ala Leu Glu
            20                  25                  30

Cys Arg Arg Cys His Val Lys Cys His Arg Asp His Leu Asp Lys Lys
        35                  40                  45

Glu Asp Leu Ile Cys
```

50

(2) INFORMATION FOR SEQ ID NO:64:

(i) SEQUENCE CHARACTERISTICS:
(A) LENGTH: 50 amino acids
(B) TYPE: amino acid
(C) STRANDEDNESS: single
(D) TOPOLOGY: linear (xi) SEQUENCE DESCRIPTION: SEQ ID NO:64:

```
His Glu Phe Thr Ala Thr Phe Phe Gly Gln Pro Thr Pro Cys Ser Val
1               5                   10                  15

Cys Lys Glu Phe Val Trp Gly Leu Asn Lys Gln Gly Tyr Lys Cys Arg
            20                  25                  30

Gln Cys Asn Ala Ala Ile His Lys Lys Cys Ile Asp Lys Ile Ile Gly
        35                  40                  45

Arg Cys
    50
```

(2) INFORMATION FOR SEQ ID NO:65:

(i) SEQUENCE CHARACTERISTICS:
(A) LENGTH: 96 amino acids
(B) TYPE: amino acid
(C) STRANDEDNESS: single
(D) TOPOLOGY: linear (xi) SEQUENCE DESCRIPTION: SEQ ID NO:65:

```
Ser Lys Lys Ala Ala Ser Arg Asn Arg Gln Glu Ile Thr Asp Lys Asp
1               5                   10                  15

His Thr Val Ser Arg Leu Glu Glu Ala Asn Ser Met Leu Thr Lys Asp
            20                  25                  30

Ile Glu Ile Leu Arg Arg Glu Asn Glu Glu Leu Thr Glu Lys Met Lys
        35                  40                  45

Lys Ala Glu Glu Glu Tyr Lys Leu Glu Lys Glu Glu Glu Ile Ser Asn
    50                  55                  60

Leu Lys Ala Ala Phe Glu Lys Asn Ile Asn Thr Glu Arg Thr Leu Lys
65                  70                  75                  80

Thr Gln Ala Val Asn Lys Leu Ala Glu Ile Met Asn Arg Lys Asp Phe
                85                  90                  95
```

(2) INFORMATION FOR SEQ ID NO:66:

(i) SEQUENCE CHARACTERISTICS:
(A) LENGTH: 119 amino acids
(B) TYPE: amino acid
(C) STRANDEDNESS: single
(D) TOPOLOGY: linear (xi) SEQUENCE DESCRIPTION: SEQ ID NO:66:

```
Ile Lys Glu Met Met Ala Arg His Lys Gln Glu Leu Thr Glu Lys Asp
1               5                   10                  15

Ala Thr Ile Ala Ser Leu Glu Glu Thr Asn Arg Thr Leu Thr Ser Asp
            20                  25                  30

Val Ala Asn Leu Ala Asn Glu Lys Glu Glu Leu Asn Asn Lys Leu Lys
        35                  40                  45

Asp Thr Gln Glu Gln Leu Ser Lys Leu Lys Asp Glu Glu Ile Ser Ala
    50                  55                  60

Ala Ala Ile Lys Ala Gln Phe Glu Lys Gln Leu Leu Thr Glu Arg Thr
65                  70                  75                  80
```

-continued

```
Leu Lys Thr Gln Ala Val Asn Lys Leu Ala Glu Ile Met Asn Arg Lys
            85                  90                  95

Glu Pro Val Lys Arg Gly Ser Asp Thr Asp Val Arg Arg Lys Glu Lys
        100                 105                 110

Glu Asn Arg Lys Leu His Met
        115


(2) INFORMATION FOR SEQ ID NO:67:

     (i) SEQUENCE CHARACTERISTICS:
          (A) LENGTH: 27 base pairs
          (B) TYPE: nucleic acid
          (C) STRANDEDNESS: single
          (D) TOPOLOGY: linear

    (xi) SEQUENCE DESCRIPTION: SEQ ID NO:67:

GGGATCCGTC GACCTGCAGC CAAGCTT                                          27


(2) INFORMATION FOR SEQ ID NO:68:

     (i) SEQUENCE CHARACTERISTICS:
          (A) LENGTH: 60 base pairs
          (B) TYPE: nucleic acid
          (C) STRANDEDNESS: single
          (D) TOPOLOGY: linear

    (xi) SEQUENCE DESCRIPTION: SEQ ID NO:68:

GGGATCCCCG GGTACCGAGC TCAATTGCGG CCGCTAGATA GATAGAAGCG AGCTCGAATT      60
```